US009074179B2

(12) United States Patent
Zitomer

(10) Patent No.: US 9,074,179 B2
(45) Date of Patent: Jul. 7, 2015

(54) BIOAUGMENTATION OF ANAEROBIC DIGESTER SYSTEMS

(75) Inventor: Daniel Zitomer, Shorewood, WI (US)

(73) Assignee: Marquette University, Milwaukee, WI (US)

( * ) Notice: Subject to any disclaimer, the term of this patent is extended or adjusted under 35 U.S.C. 154(b) by 362 days.

(21) Appl. No.: 13/079,524

(22) Filed: Apr. 4, 2011

(65) Prior Publication Data

US 2011/0244541 A1 Oct. 6, 2011

Related U.S. Application Data

(60) Provisional application No. 61/341,705, filed on Apr. 2, 2010, provisional application No. 61/396,337, filed on May 26, 2010, provisional application No. 61/396,339, filed on May 26, 2010, provisional application No. 61/396,340, filed on May 26, 2010.

(51) Int. Cl.
*C12P 5/02* (2006.01)
*C12N 1/00* (2006.01)
*C12N 1/04* (2006.01)

(52) U.S. Cl.
CPC ... *C12N 1/04* (2013.01); *C12P 5/02* (2013.01); *Y02E 50/343* (2013.01)

(58) Field of Classification Search
CPC ..... Y02E 50/343; Y02E 50/10; Y02E 60/527; Y02E 50/13; Y02E 50/30; C12P 5/023; C12P 39/00; C12P 7/04; C12P 7/065; C12P 7/08; C12P 7/52; C12M 21/04; C12M 43/02; C12N 1/20; C12N 13/00; C12N 1/22
See application file for complete search history.

(56) References Cited

U.S. PATENT DOCUMENTS

| | | | |
|---|---|---|---|
| 5,783,081 | A | 7/1998 | Gaddy |
| 2009/0107913 | A1 | 4/2009 | Johnson |

FOREIGN PATENT DOCUMENTS

| | | |
|---|---|---|
| JP | 2003260435 | 9/2003 |
| JP | 2005125149 | 5/2005 |
| KR | 1020060064271 | 6/2006 |
| KR | 1020080089825 | 10/2008 |

OTHER PUBLICATIONS

Ahn et al. The effect of calcium on the anaerobic digestion treating swine wastewater, Biochemical Engineering Journal vol. 30, Issue 1, May 1, 2006, pp. 33-38.*
Daniel Zitomer (Stoichiometry of combined aerobic and methanogenic COD transformation, Water Research, 1998b, 32(3): 669-676).*
Tale et al., "Bioaugmentation of overloaded anaerobic digesters restores function and archaeal community," Water Research, 2015, 70:138-147.
Abeysinghe et al., "The effectiveness of bioaugmentation in nitrifying systems stressed by a washout condition and cold temperature", Water Environment Research, Mar./Apr. 2002, 74(2):187.
Angelidaki et al., "Anaerobic Biodegradation, Activity and Inhibition (ABAI)", Task Group Meeting. Prague, Czech Republic, Oct. 9-10, 2007.
Angelidaki et al., "Methods for increasing the biogas potential from the recalcitrant organic matter contained in manure", Water Science and Technology, 2000, 41(3):189-194.
Castro et al., "Preservation methods for the storage of anaerobic sludges", Biotechnology Letters, 2002, 24:329-333.
Charest et al., "Removal of phenolic compounds from a petrochemical effluent with a methanogenic consortium", Can. J. Microbiol., 1999, 45:235-241.
Chouari et al., "Novel predominant archaeal and bacterial gropus revealed by molecular analysis of an anaerobic sludge digester", Environmental Microbiology, 2005, 7(8):1104-1115.
Coates et al., "Simple method for the measurement of the hydrogenotrophic methanogenic activity of anaerobic sludges", Journal of Microbiological Methods, 1996, 26:237-246.
Cole et al., "The ribosomal database project (RDP-II): introducting myRDP space and quality controlled public data", Nucleic Acids Research, 2007, 35:D169-D172.
Colleran et al., "Use of methanogenic activity tests to characterize anaerobic sludges, screen for anaerobic biodegradability and determine toxicity thresholds against individual anaerobic trophic groups and species", Wat. Sci. Tech., 1992, 25(7):31-40.
Earl et al., "Analysis of methanogen diversity in a hypereutrophic lake using PCT-RFLP analysis of mcr sequences", Microbial Ecology, 2003, 46:270-278.
El Fantroussi et al., "Is bioaugmentation a feasible strategy for pollutant removal and site remediation", Current Opinion in Microbiology, 2005, 8:268-275.
Guiot et al., "Strategies for augmenting the pentachlorophenol degradation potential of UASB anaerobic granules", Water Science and Technology, 2002, 45(10):35-41.
Guiot et al., "Immobilization strategies for bioaugmentation of anaerobic reactors treating phenolic compounds", Water Science and Technology, 2000, 42(5-6):245-250.
Head et al., "Bioaugmentation with nitrifying bacteria acclimated to different temperatures", Journal of Environmental Engineering, Jul. 2005, 131(7):1046-1051.
Iino et al., "Improvement of the L-drying procedure to keep anaerobic conditions for long-term preservation of methanogens in a culture collection", Microbiol. Cult. Coll., Dec. 2006, 22(2):99-104.
Kadam et al., "Granulation technology for bioproducts", Informa Healthcare, May 14, 2010.
Kolukirik et al., "Changes in acetoclastic methanogenic activity and archaeal composition in a full-scale UASB reactor treating an alcohol distillery effluent", 2004, 53-58.
Leclerc et al., "Diversity of the archaeal community in 44 anaerobic digesters as determined by single strand conformation polymorphism analysis and 16S rDNA sequencing", Environmental Microbiology, 2004, 6(8):809-819.

(Continued)

*Primary Examiner* — Iqbal H Chowdhury
(74) *Attorney, Agent, or Firm* — Andrus Intellectual Property Law, LLP

(57) ABSTRACT

Disclosed herein are methods for improving performance of an anaerobic digester system. The methods typically include adding a culture comprising hydrogenotrophic methanogens to the system, otherwise referred to as bioaugmentation.

20 Claims, 26 Drawing Sheets

(56) References Cited

OTHER PUBLICATIONS

Lueders et al., "Molecular analyses of methyl-coenzyme M reductase alpha-subunit (mcrA) genes in rice field soil and enrichment cultures reveal the methanogenic phenotype of a novel archaeal lineage", Environmental Microbiology, 2001, 3(3):194-204.
Malik et al., "A simplified liquid-drying method for the preservation of microorganisms sensitive to freezing and freeze-drying", Journal of Microbiological Methods, 1990, 12:125-132.
McCarty et al., "Anaerobic wastewater treatment", Environ. Sci. Technol., 1986, 20(12):1200.
Mladenovska et al., "Bioaugmentation of a mesophilic biogas reactor by anaerobic xylanolytic- and cellulolytic bateria", Proceedings of the Ninth World Congress on Anaerobic Digestion, Antwepen, Belgium, 2001, 183-188.
Morgan et al., "Preservation of micro-organisms by drying: A review", Journal of Microbiological Methods, 2006, 66:183-193.
Nercessian et al., "Phylogenetic analysis of peat bog methanogen populations", FEMS Microbiology Letters, 1999, 173:425-429.
Nielsen et al., "Bioaugmentation of a two-stage thermophilic anaerobic digestion concept for improvement of the methane yield from cattle manure", Biotechnology and Bioengineering, Aug. 15, 2007, 97(6):1638.
O'Flaherty et al., "Effect of sulphate addition on volatile fatty acid and ethanol degradation in an anaerobic hybrid reactor II: microbial interactions and toxic effects", Bioresource Technology, 1999, 68:109-120.
Ohkuma et al., "Phylogeny of symbiotic methanogens in the gut of the termite", FEMS Microbiology Letters, 1995, 134:45-50.
Owen et al., "Bioassay for monitoring biochemical methane potential and anaerobic toxicity", Water Research, 1979, 13:485-492.
Rastogi et al., "Investigation of methanogen population structure in biogas reactor by molecular characterization of methyl-coenzyme", Bioresource Technology, 2008, 99:5317-5326.
Rittmann et al., "Bioaugmentation: A coming of age", Water Quality International, 1994, 1:12-16.
Sakane et al., "Viabilities of dried cultures of various bacteria after preservation for over 20 years and their prediction by the accelerated storage test", Microbiol. Cult. Coll. Jun. 1997, 13(1):1-7.
Saravanane et al., "Bioaugmentation and anaerobic treatment of pharmaceutical effluent in fluidized bed reactor", J. Environ. Sci. Health, 2001, A36(5):779-791.
Saravanane et al., "Bioaugumentation and treatment of cephalexin drug-based pharmaceutical effluent in an upflow anaerobic fluidized bed system", Bioresource Technology, 2001, 76:279-281.
Satoh et al., "Evaluation of the impact of bioaugmentation and biostimulation by in situ hybridization and microelectrode", Water Research, 2003, 37:2206-2216.
Singer et al., "Perspectives and vision for strain selection in bioaugmentation", Trends in Biotechnology, Feb. 2005, 23(2):74-77.
Simione et al., "ATCC preservation methods: freezing and freeze-drying", American Type Culture Collection, Second Edition, 1991.
Smith et al., "Factors governing methane fluctuations following shock loading of digesters", Research Journal of the Water POllution Control Federation, Jan.-Feb. 1990, 62(1):58-64.
Sorensen et al., "Measurements of the specific methanogenic activity of anaerobic digester biomass", Appl Microbiol Biotechnol, 1993, 40:427-431.
Staab et al., "Viability of lyophilized anaerobes in two media", Cryobiology, 1987, 24:174-178.
Stephenson et al., "Bioaugmentation for enhancing biological wastewater treatment", Biotech Adv, 1992, 10:549-559.
Tawfiki et al., "Simultaneous removal of phenol, ortho- and para-cresol by mixed anaerobic consortia", Can. J. Microbio., 1999, 45:318-325.
Tawfiki et al., "Effects of bioaugmentation strategies in UASB reactors with a methanogenic consortium for removal of phenolic compounds", Biotechnology and Bioengineering, 2000, 67(4):417-423.
Van Limbergen et al., "Bioaugmentation in activated sludge: current features and future perspectives", Appl Microbiol Biotechnol, 1998, 50:16-23.
Zitomer et al., "Feasibility and benefits of methanogenesis under oxygen-limited conditions", Waster Management, 1998, 18:107-116.
International Search Report and Written Opinion for PCT/US2011/031099 dated Dec. 21, 2011.
International Search Report and Written Opinion for PCT/US2011/031077 dated Dec. 22, 2011.
Ahring et al., "Introduction of a De Novo Bioremediation Ability, Aryl Reductive Dechlorination, into Anaerobic Granular Sludge by Inoculation of Sludge with *Desulfomonile tiedjei*", Applied and Environmental Microbiology, Nov. 1992, 58(11):3677-3682.
Altschul et al., "Gapped BLAST and PSI-BLAST: a new generation of protein database search programs", Nucleic Acids Research, 1997, 25(17):3389-3402.
Berner et al., "Effect of protective agents on the viability of *Lactococcus lactis* subjected to freeze-thawing and freeze-drying", Scientia Pharmaceutica, 2006, 74:137-149.
Bidle et al., "A phylogenetic analysis of microbial communities associated with methane hydrate containing marine fluids and sediments in the Cascadia margin (ODP site 892B)", FEMS Microbiology Letters, 1999, 17:101-108.
Cirne et al., "Effects of bioaugmentation by an anaerobic lipolytic bacterium on anaerobic digestion of lipid-rich waste", Journal of Chemical Technology and Biotechnology, 2006, 81:1745-1752.
Cole et al., "The Ribosomal Database Project (RDP-II): sequences and tools for high-throughput rRNA analysis", Nucleic Acids Research, 2005, 33:D294-D2%.
Cole et al., "The Ribosomal Database Project (RDP-II): introducing myRDP space and quality controlled public data", Nucleic Acids Research, 2007, 35:D169-D172.
Delong, "Archaea in coastal marine environments", PNAS, Jun. 1992, 89:5685-5689.
Dhillon et al., "Methanogen Diversity Evidenced by Molecular Characterization of Methyl Coenzyme M Reductase A (mcrA) Genes in Hydrothermal Sediments of the Guaymas Basin", Applied and Environmental Microbiology, Aug. 2005, 71(8):4592-4601.
Duran et al., "Bioaugmenting anaerobic digestion of biosolids with selected strains of *Bacillus, Pseudomonas,* and *Actinomycetes* species for increased methanogenesis and odor control", Appl Microbiol Biotechnol, 2006, 73:960-966.
Fernandez et al., "Flexible Community Structure Correlates with Stable Community Function in Methanogenic Bioreactor Communities Perturbed by Glucose", Applied and Environmental Microbiology, Sep. 2000, 66(9):4058-4067.
Galand et al., "Depth related diversity of methanogen Archaea in Finnish oligotrophic fen", FEMS Microbiology, Ecology, 2002, 42:441-449.
Grotenhuis et al., "Bacteriological Compositions and Structure of Granular Sludge Adapted to Different Substrates", Applied and Environmental Microbiology, Jul. 1991, 57(7):1942-1949.
Hales et al., "Isolation and Identification of Methanogen-Specific DNA from Blanket Bog Peat by PCR Amplification and Sequence Analysis", Applied and Environmental Microbiology, Feb. 1996, 62(2):668-675.
Hashsham et al., "Parallel Processing of Substrate Correlates with Greater Functional Stability in Methanogenic Bioreactor Communities Perturbed by Glucose", Applied and Environmental Microbiology, Sep. 2000, 66(9):4050-4057.
Horber et al., "Improved Dechlorinating Performance of Upflow Anaerobic Sludge Blanket Reactors by Incorporation of Dehalospirillum multivorans into Granular Sludge", Applied and Environmental Microbiology, May 1998, 64(5):1860-1863.
Huang et al., "Characterization of methanogenic Archaea in the leachate of a closed municipal solid waste landfill", FEMS Microbiology Ecology, 2003, 46:171-177.
Hubalek, "Protectants used in the cryopreservation of microorganisms", Cryobiology, 2003, 46:205-229.
Juottonen et al., "Detection of methanogenic Archae in peat: comparison of PCR primers targeting the mcrA gene", Research in Microbiology, 2006, 157:914-921.
Lange et al., "A comprehensive study into the molecular methodology and molecular biology of methanogenic Archaea", FEMS Microbiology Reviews, 2001, 25:553-571.

(56) References Cited

OTHER PUBLICATIONS

Lenz et al., "Bioaugmentation of UASB reactors with immobilized *Sulfurospirillum barnesii* for simultaneous selenate and nitrate removal", Appl Microbiol Biotechnol, 2009, 83:377-388.

Lloyd et al., "Micro-ecology of peat: minimally invasive analysis using confocal laser scanning microscopy, membrane inlet mass spectrometry and PCR amplification of methanogen-specific gene sequences", FEMS Microbiology Ecology, 1998, 25:179-188.

Luton et al., "The mcrA gene as an alternative to 16S rRNA in the phylogenetic analysis of methanogen populations in landfill", Microbiology, 2002, 148:3521-3530.

Macario et al., "Quantitative Immunologic Analysis of the Methanogenic Flora of Digestors Reveals a Considerable Diversity", Applied and Environmental Microbiology, Jan. 1988, 54(1):79-86.

McHugh et al., "Methanogenic population structure in a variety of anaerobic bioreactors", FEMS Microbiology Letters, 2003, 219:297-304.

Raskin et al., "Characterization of microbial communities in anaerobic bioreactors using molecular probes", Antonie van Leeuwenhoek, 1995, 68:297-308.

Schauer-Gimenez et al., "Bioaugmentation for Improved Recovery of Anaerobic Digesters After Toxicant Exposure", Water Research, Jun. 2010, 44(12):3555-3564.

Schloss et al., "Introducing DOTUR, a Computer Program for Defining Operational Taxonomic Units and Estimating Species Richness", Applied and Environmental Microbiology, Mar. 2005, 71(3):1501-1506.

Sekiguchi et al., "Phylogenetic diversity of mesophilic and thermophilic granular sludges determined by 16S rRNA gene analysis", Microbiology, 1998, 144:2655-2665.

Steinberg et al., "Phylogenetic Comparison of the Methanogenic Communities from an Acidic, Oligotrophic Fen and an Anaerobic Digester Treating Municipal Wastewater Sludge", Applied and Environmental Microbiology, Nov. 2008, 74(21):6663-6671.

Tale et al., "Bioaugmentation for Anaerobic Digester Recovery After Organic Overload", Water Environment Federation Technical Exposition and Conference (WEFTEC 2010), New Orleans, LA, 14 pp.

Tartakovsky et al., "Biodegradation of Pentachlorophenol in a Continuous Anaerobic Reactor Augmented with Desulfitobacterium frappieri PCP-1", Applied and Environmental Microbiology, Oct. 1999, 65(10):4357-4362.

Thauer, "Biochemistry of methanogenesis: a tribute to Marjory Stephenson", Microbiology, 1998, 144:2377-2406.

Ufnar et al., "Development of a Swine-Specific Fecal Pollution Marker Based on Host Differences in Methanogen mcrA Genes", Applied and Environmental Microbiology, Aug. 2007, 73(16):5209-5217.

Wilms et al., "Methane and sulfate profiiles within the subsurface of a tidal flat are reflected by the distribution of sulfate-reducing bacteria and methanogenic archaea", FEMS Microbiol Ecol, 2007, 59:611-621.

Wittebolle et al., "Initial community evenness favours functionality under selective stress", Nature, Apr. 2, 2009, 458:623-626.

Woese et al., "Phylogenetic Structure of the Prokaryotic Domain: The Primary Kingdoms", PNAS, 1977, 74:5088-5090.

Zitomer et al., "Metal Stimulation and Municipal Digester Thermophilic/Mesophilic Activity", Journal of Environmental Engineering, Jan. 2008, 134(1):42-47.

* cited by examiner

BIOAUGMENTATION OF ANAEROBIC DIGESTER SYSTEMS

CROSS-REFERENCE TO RELATED APPLICATIONS

The present application claims the benefit under 35 U.S.C. §119(e) to U.S. Provisional Application Nos. 61/341,705, filed on Apr. 2, 2010; 61/396,337, filed on May 26, 2010; 61/396,339, filed on May 26, 2010; and 61/396,340, filed on May 26, 2010; the contents of which are incorporated herein by reference in their entireties

BACKGROUND

The field of the invention relates to methods of improving performance of anaerobic digester systems, otherwise referred to as "bioaugmentation." In particular, the field of the invention relates to bioaugmentation of anaerobic digester systems in order to improve performance parameters related to production of methane, reduction in effluent chemical oxygen demand (COD) or recovery from organic overload.

Methane is a commercially valuable fuel, as well as synthetic precursor, and can be obtained via microbial fermentation processes. In addition, proper methane production is required for stabilization of municipal, industrial and agricultural wastes via anaerobic digestion. Many euryarchaeotal microorganisms can use hydrogen and carbon dioxide to produce methane.

Anaerobic digester systems are used to treat wastes and produce renewable energy. In the process, select microorganisms are contacted with the waste and convert it to biogas that contains methane. The methane can be used as a renewable fuel.

Anaerobic digestion is a multistep process with different microbial communities working in syntrophy. If the syntrophy is disrupted by organic overload or other changes, then the entire process may slow or stop, causing costly delays at agricultural, industrial, and municipal treatment plants. Most notably, efficient metabolism of hydrogen ($H_2$) and propionic acid is required. Propionate and $H_2$ accumulation have been seen as an indicator of process imbalance (McCarty and Smith, 1986).

Propionate accumulation is an indicator of process imbalance in organically overloaded anaerobic digesters. Following the overload, methane production can take months to recover. Upset of anaerobic digesters due to an organic overloading is a common problem in the field, and practical methods to reduce recovery time would be beneficial and of commercial value.

Practical methods to reduce recovery time of upset digesters would be beneficial and commercially valuable. One potential method is "bioaugmentation," the addition of specific, active microbes to enhance performance. Regarding anaerobic digestion, no published reports of full-scale applications were found; however, reports of laboratory studies describe bioaugmentation to improve degradation of specific chemicals, digester startup, recovery of stressed digesters, and odor reduction (e.g., Saravanane et al., 2001).

Oxygen ($O_2$) toxicity tolerance of anaerobic cultures used for bioaugmentation is of particular importance. Methanogenic cultures that are resistant to $O_2$ toxicity may be better choices as bioaugmentation cultures since they may contain unique, beneficial microbial communities or be more easily freeze-dried, stored and transported in an air atmosphere.

Currently, very little attention is paid to the exact microorganisms used during anaerobic (or aerobic) digestion. Likewise, little attention is paid to the digester microbial community structure, and the relationship between community structure and digester performance. When a digester is started, it is common practice to obtain starter culture from the most near-by operating digester system and the exact microbes present are not determined. Regarding performance, some digester systems may not produce as much biogas as possible, and other digesters may loose biogas production due to changes in feed waste composition, temperature, or other factors. As such, methods for enhancing performance of anaerobic digester systems are desirable including methods of bioaugmentation.

SUMMARY

Disclosed herein are methods for improving performance of an anaerobic digester system. The methods typically include adding a culture comprising hydrogenotrophic methanogens to the system, otherwise referred to as bioaugmentation. The culture optionally may include fermenting microorganisms, such as microorganisms that ferment propionate or butyrate.

In some embodiments, the methods include methods of increasing methane production in an anaerobic digester system by adding a culture comprising hydrogenotrophic methanogens to the system. Suitable hydrogenotrophic methanogens may include, but are not limited to, hydrogenotrophic methanogens belonging to the order Methanomicrobales or to the order Methanobacteriales, such as *Methanospirillum hungatei, Methanobacterium heijingense, Methanolinea tarda* or related hydrogenotrophic methanogens. In some embodiments, *Methanospirillim hungatei, Methanobacterium beijingense, Methanolinea tarda* or related hydrogenotrophic methanogens represent at least about 95% of hydrogenotrophic methanogens belonging to the order Methanomicrobiales or to the order Methanobacteriales in the culture.

Suitable cultures may comprise components of wastewater sludge. In some embodiments, prior to being added to the anaerobic digester system, the culture is treated, enriched, or selected. For example, prior to being added to the anaerobic digester system, the culture may be grown in the presence of oxygen. In other embodiments, prior to being added to the anaerobic digester system, the culture may be grown in the presence of an organic acid or a salt thereof. The culture typically comprises hydrogenotrophic methanogens and preferably comprises microorganisms that are capable of metabolizing propionate, butyrate, or other organic acids.

The culture may be added to the anaerobic digester system at a suitable rate as measured by volatile suspended solids (VSS)/L-day. The culture may be added to the anaerobic digester system for any suitable period of time (e.g., days, weeks, or months). In some embodiments, prior to adding the culture, partial pressure of hydrogen in the anaerobic digester system is at least $10^{-6}$ atm (e.g., in the head space) and the culture is added to the system for a period of time that is sufficient to reduce the partial pressure of hydrogen in the system to less than $10^{-6}$ atm. In other embodiments, prior to adding the culture, the anaerobic digester system has a pH of no more than 6.6, and the culture is added to the system for a period of time that is sufficient to raise the pH above 6.6. In further embodiments, prior to adding the culture, the anaerobic digester system has a propionic acid concentration of at least 500 mg/L, and the culture is added to the system for a period of time that is sufficient to reduce the propionic acid concentration below 500 mg/L. In even further embodiments, prior to adding the culture, the system has a soluble chemical oxygen demand (SCOD) of at least 1000 mg/L, and the culture is added to the system for a period of time that is sufficient to reduce the SCOD to less than 1000 mg/L.

DETAILED DESCRIPTION

Figure 1:
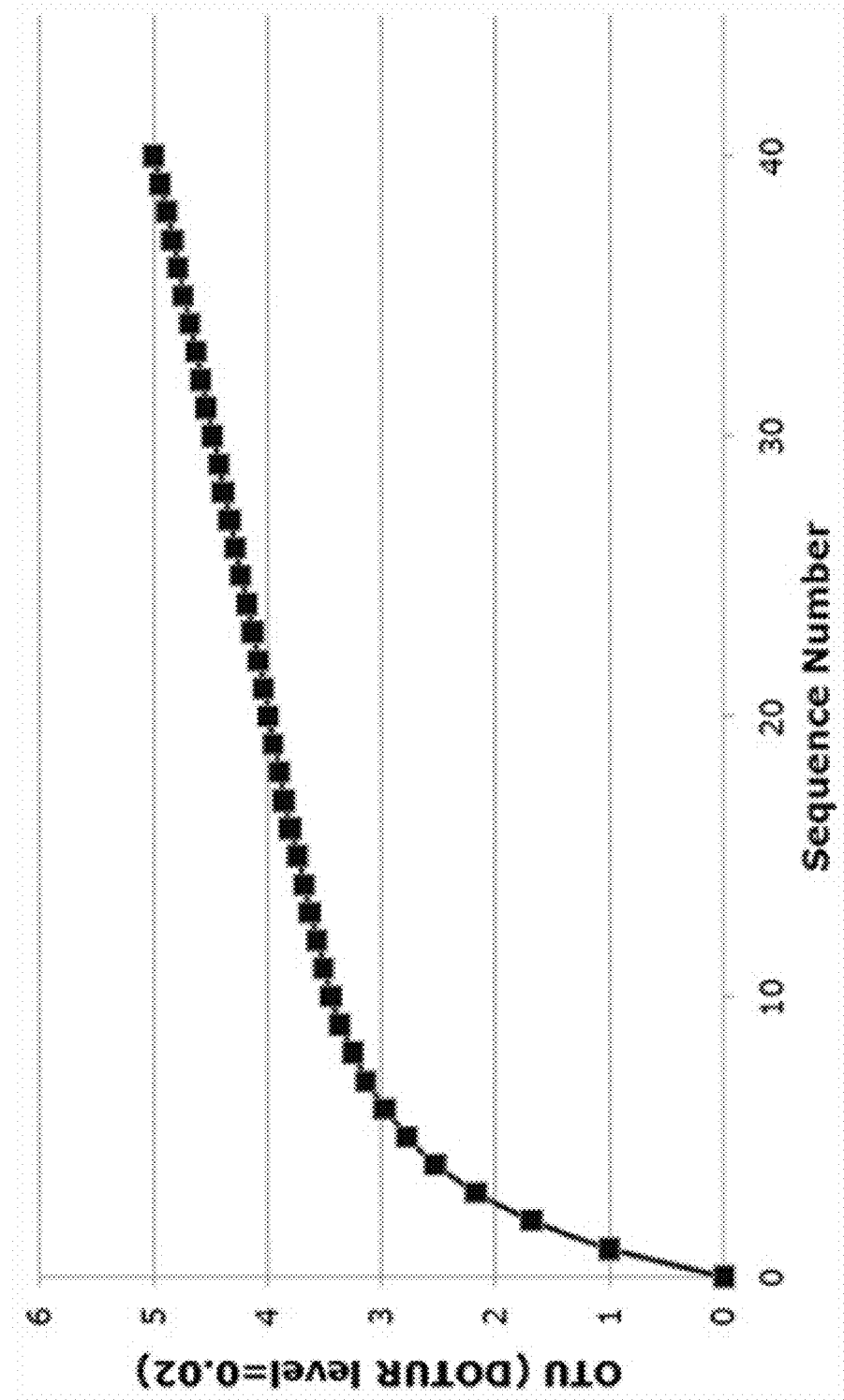
FIG. 1 illustrates a rarefaction curve of archael clone library of a bioaugmentation culture.

The disclosed subject matter further may be described utilizing terms as defined below.

Unless otherwise specified or indicated by context, the terms "a", "an", and "the" mean "one or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising."

As contemplated herein, cultures comprising methanogens may be utilized to bioaugment anaerobic digester systems. (See, e.g., Schauer-Gimenez et al., "Bioaugmentation for Improved Recovery of Anaerobic Digesters After Toxicant Exposure," *Wat. Res.* 44 (2010), pp. 3555-3564; Tale et al., "Bioaugmentation Can Improve Anaerobic Digester Performance after Organic Overload," (2010) in proceedings of International Water Association (IWA) 12th. World Congress on Anaerobic Digestion, Guadalajara, Mexico, October 31st-November 4th, 5 pp; and Tale et al., "Bioaugmentation for Anaerobic Digester Recovery After Organic Overload," Water Environment Federation Technical Exposition and Conference (WEFTEC 2010), New Orleans, La., 14 pp); the contents of which are incorporated herein by reference in their entireties). Anaerobic digestion is a series of processes in which microorganisms break down biodegradable material in the absence of oxygen. Anaerobic digestion is used for agricultural, industrial, or municipal purposes to manage waste and/or to release energy. The digestion process begins with bacterial hydrolysis of input materials in order to break down insoluble organic polymers such as carbohydrates and proteins into sugars and amino acids. Acidogenic bacteria then convert the sugars and amino acids into carbon dioxide, hydrogen, ammonia, and organic acids. Acetogenic bacteria then convert these resulting organic acids into acetic acid, and produce additional ammonia, hydrogen, and carbon dioxide. Finally, methanogens convert products to methane and carbon dioxide.

As used herein, the term "methanogen" is intended to include single-celled microorganisms belonging to the domain Archaea such as those Archaea typically present in anaerobic digester systems. Methanogens (or methanogenic Archaea) are responsible for methane production in anaerobic digester systems and include the following genera: *Methanobacterium*, *Methanobacillus*, *Methanococcus*, *Methanosaeta*, and *Methanosarcina*. Microorganisms belonging to these genera may be identified by techniques involving the extraction and analysis of the 16S rRNA gene.

Methanogens utilize a limited number of substrates to generate methane, including carbon dioxide ($CO_2$)-type substrates (e.g., $CO_2$, formate, and carbon monoxide), methyl substrates (e.g., methanol, methylamine, dimethylamine, trimethylamine, methylmercaptan, and dimethyl sulfide), and acetate.

In anaerobic digester systems, the two primary substrates that are utilized by methanogens are acetate and hydrogen. Methane ($CH_4$) can be generated in anaerobic digesters through transformation of either acetate or hydrogen by acetotrophic methanogens or hydrogenotrophic methanogens, respectively. Acetotrophic methanogens reduce acetate directly to $CH_4$ and $CO_2$. *Methanosarcina* and *Methanosaeta* (formerly known as *Methanothrix*), both belonging to the order Methanosarcinales, are the only reported acetotrophic methanogen genera.

The reduction of $CO_2$ using $H_2$ as the electron donor is another method for the generation of $CH_4$ via the equation: $4H_2+CO_2 \rightarrow CH_4+2H_2O$. The majority of the methanogens can utilize $H_2$ and $CO_2$ to produce $CH_4$, including members from the orders Methanobacteriales, Methanococcales, Methanomicrobiales, and Methanopyrales. Some of the genera in the order Methanobacteriales include *Methanobacterium* (e.g., *Methanobacterium beijingense*), Methanobrevibacter, Methanosphaera, Methanothermus, and Methanothermobacter. Methanococcales are cocci that can be regular or irregular in shape. Genera in this order include Methanococcus, Methanothermococcus, Methanocaldococcus, and Methanotorris. The order Methanomicrobiales includes a diverse assemblage of methanogens. Genera in this order include *Methanomicrobium*, *Methanogenium*, *Methanospirillum* (e.g., *Methanospirillum hungatei*), *Methanoplanus*, *Methanocorpusculum*, *Methanoculleus*, *Methanofollis*, *Methanolinea* (e.g, *Methanolinea tarda*) and *Methanolacinia*.

The bioaugmentation cultures utilized in the methods contemplated herein may comprise methanogens that are related to the aforementioned methanogens. A methanogen that is related to another methanogen may be defined as a methanogen having a gene which has substantial sequence identity to the corresponding gene in the other methanogen. For example, a methanogen that is related to one of the aforementioned methanogens may have a 16S rRNA gene that exhibits at least about 85%, 90%, 95%, 96%, 97%, 98%, or 99% sequence identity to the 16S rRNA gene of one of the aforementioned methanogens (e.g., as determined by aligning the 16S rRNA genes using the Basic Local Alignment Search Tool (BLAST) available from the National Center for Biotechnology Information (NCBI) at its website). The nucleotide sequences of the 16S rRNA genes for *Methanospirillum hungatei, Methanobacterium beijingense*, and *Methanolinea tarda* have been reported. (See SEQ ED NOS:1, 2, and 3, respectively). Alternatively, a methanogen that is related to one of the aforementioned methanogens may have an mcrA gene that exhibits at least about 85%, 90%, 95%, 96%, 97%, 98%, or 99% sequence identity to the mcrA gene of one of the aforementioned methanogens. Methyl coenzyme-M reductase (MCR) is the terminal enzyme complex in the biological methane generation pathway and catalyzes the reduction of the methyl group bound to coenzyme-M, thereby releasing methane. This enzyme complex is thought to be unique to and ubiquitous in methanogens which makes it a suitable marker for the detection and characterization of methanogens. The MCR operon exists in two forms, MCRI and MCRII. The MCRI form is thought to be present in all methanogens, while the MCRII form has been found to be present only in the members of the orders Methatnobacteriales and Methanococcales. Researchers have selected the mcrA gene, which encodes one protein of the MCRI complex, as a suitable marker for the development of PCR-based detection and characterization of methanogens. The nucleotide sequences of the mcrA genes for *Methanospirillum hungatei, Methanobacterium beijingense*, and *Methanolinea tarda* have been reported. (See SEQ ID NOS:4, 5, and 6, respectively).

As examples, a methanogen that is related to *Methanospirillum hungatei* may have a 16S rRNA gene or an mcrA gene which has at least about 85%, 90%, 95%, 96%, 97%, 98%, or 99% sequence identity to the corresponding gene in *Methanospirillum hungatei* (i.e., SEQ ID NO:1 and 4, respectively). A methanogen that is related to *Methanolinea tarda* may have a 16S rRNA gene or an mcrA gene which has at least about 85%, 90%, 95%, 96%, 97%, 98%, or 99% sequence identity to the corresponding gene in *Methanolinea tarda* (i.e., SEQ ID NO:2 and 5, respectively). A methanogen that is related to *Methanobacterium beijingense* may have a 16S rRNA gene or an mcrA gene which has at least about 85%, 90%, 95%, 96%, 97%, 98%, or 99% sequence identity to the corresponding gene in *Methanobacterium beijingense* (i.e., SEQ ID NO:3 and 6, respectively).

Bioaugmentation cultures utilized in the methods contemplated herein may comprise or consist of one or more of the foregoing described methanogens. In some embodiments, bioaugmentation cultures utilized in the methods contemplated herein comprise a substantially homogenous population of one of the foregoing described methanogens. In other embodiments, cultures utilized in the methods contemplated herein comprise a heterogenous population of more than one of the foregoing described methanogens. Contemplated populations of methanogens may be enriched in or depleted of one or more of the foregoing methanogens. For example, in a culture comprising a population of methanogens, one or more of the foregoing methanogens may represent at least about 1%, 2%, 3%, 5%, 10%, 25%, 50%, 75%, 90%, 95%, 96%, 97%, 98%, or 99% of total methanogens in the population. Alternatively, in a culture comprising a population of methanogens, one or more of the foregoing methanogens may represent no more than about 1%, 2%, 3%, 5%, 10%, 25%, 50%, 75%, 90%, 95%, 96%, 97%, 98%, or 99% of total methanogens in the population.

Cultures used in the methods disclosed herein may be obtained from sources which include, but are not limited to, wastewater treatment plants, for example, biomass obtained from wastewater treatment plants such as sludge. As discussed above, cultures utilized in the methods contemplated herein may comprise or consist of a heterogenous population of microorganisms including methanogens. Alternatively, cultures utilized in the methods contemplated herein may comprise or consist of a homogenous population of microorganism. Methods of isolating a single microorganism from a heterogenous population of microorganisms are known in the art.

Bioaugmentation cultures utilized in the methods contemplated herein may be subjected to treatment, selection, or enrichment prior to being added to an anaerobic digester system. In some embodiments, the cultures are grown in the presence of oxygen prior to being added to an anaerobic digester system. For example, the cultures may be grown in the presence of oxygen given at a daily dose of at least about 2.5 mg/L-day (or at a dose of at least about 2.5 mg/L-day, 5 mg/L-day, 10 mg/L-day, 15 mg/L-day, 20 mg/L-day, 25 mg/L-day, 30 mg/L-day, 35 mg/L-day, 40 mg/L-day, 45 mg/L-day, 50 mg/L-day, 55 mg/L-day, 60 mg/L-day, 65 mg/L-day, 70 mg/L-day, 75 mg/L-day, 80 mg/L-day, 85 mg/L-day, 90 mg/L-day, 95 mg/L-day, 100 mg/L-day, 105 mg/L-day, 110 mg/L-day, 115 mg/L-day, 120 mg/L-day, 125 mg/L-day, 130 mg/L-day, 135 mg/L-day, 140 mg/L-day, 145 mg/L-day, 150 mg/L-day, 155 mg/L-day, 160 mg/L-day, 165 mg/L-day, 170 mg/L-day, 175 mg/L-day, 180 mg/L-day, 185 mg/L-day, 190 mg/L-day, 195 mg/L-day, 200 mg/L-day, 205 mg/L-day, 210 mg/L-day, 215 mg/L-day, 220 mg/L-day, 225 mg/L-day, 230 mg/L-day, 235 mg/L-day, 240 mg/L-day, 245 mg/L-day, or 250 mg/L-day. The cultures may be grown in the presence of the dose of oxygen for a suitable period of time, such as at least about 1, 2, 3, 4, 5, 6, 7, 8, 9, 10, 15, 20, or 25 days.

In other embodiments, bioaugmentation cultures utilized in the methods contemplated herein may be grown in the presence of a selected substrate prior to being added to an anaerobic digester system. For example, cultures subjected to the drying methods contemplated herein may be grown in the presence of an organic acid or a salt thereof. Suitable organic acids or salts thereof may include carboxylic acids or salts thereof having at least three carbon atoms. Typically, the carboxylic acids are volatile carboxylic acids. Suitable carboxylic acids or salts thereof may include, but are not limited to propionic acid or propionate salts (e.g., calcium propionate), butyric acid or butyrate salts. For example, cultures utilized in the methods contemplated herein may be grown in the presence of an organic acid or a salt thereof given at a daily dose of at least about 0.01 g/L-day (or at a daily dose of at least about 0.02 g/L-day, 0.03 g/L-day, 0.04 g/L-day, 0.05 g/L-day, 0.06 g/L-day, 0.07 g/L-day, 0.08 g/L-day, 0.09 g/L-day, 0.10 g/L-day, 0.11 g/L-day, 0.12 g/L-day, 0.13 g/L-day, 0.14 g/L-day, 0.15 g/L-day, 0.16 g/L-day, 0.17 g/L-day, 0.18 g/L-day, 0.19 g/L-day, 0.20 g/L-day, 0.21 g/L-day, 0.22 g/L-day, 0.23 g/L-day, 0.24 g/L-day, 0.25 g/L-day, 0.30 g/L-day, 0.35 g/L-day, 0.40 g/L-day, 0.45 g/L-day, or 0.50 g/L-day). The cultures may be grown in the presence of the dose of the organic acid or the salt thereof for a suitable period of time, such as at least about 1, 2, 3, 4, 5, 6, 7, 8, 9, 10, 15, 20, or 25 days.

Optionally, the bioaugmentation cultures utilized in the methods contemplated herein may be dried prior to being added to an anaerobic digester system. For example, a bioaugmentation culture comprising one or more methanogens may be dried by exposure to air, which should be understood to comprise oxygen (e.g., at a concentration of about 21% by volume). In the presently disclosed methods, a bioaugmentation culture comprising one or more methanogens may be dried to prepare a dry composition having a relatively low moisture content. For example, relative moisture content (RMC) of the dried bioaugmentation compositions prepared by the disclosed methods typically are less than about 20%, 15%, 10%, 9%, 8%, 7%, 6%, or 5% by mass.

Optionally, prior to being added to the anaerobic digester system, the bioaugmentation culture comprising one or methanogens may be air-dried (e.g., where the culture is exposed to ambient conditions such as a room temperature of about 15-25° C. (preferably about 20° C.) and standard atmospheric pressure), heat-dried (e.g., where the culture is heated to a temperature of at least about 30° C., 40° C., 50° C., 60° C., 70° C., 80° C., 90° C., 100° C., 110° C., 120° C., or 130° C., or to temperature within a range of about 80-130° C., 90-120° C., or 100-110° C., for example, for a period of time of at least about 1 hour, 2 hours, 4 hours, 8 hours, 1 day, 2 days, 3 days, 1 week, 2 weeks, or 3 weeks), freeze-dried (e.g., via freezing the culture at a temperature of less than about −20° C., −30° C., −40° C., −50° C., −100° C., or −200° C., subsequently raising the temperature to at least about −10° C., −15° C., −20° C., −25° C., −30° C., −35° C., −40° C., −45° C., −50° C., or −100° C. and subjecting the frozen culture to a vacuum of at least about 1, 2, 3, 4, 5, 10, 15, 20, 25, or 50 pascals, which may be a vacuum sufficient to cause sublimation), spray-dried, or a combination thereof. The steps for drying the bioaugmentation culture may include a combination of one or more of heating, freezing, and/or exposures to a vacuum as described above.

Optionally, a cryoprotectant may be added to a liquid bioaugmentation culture prior to the liquid bioaugmentation culture being subjected to the disclosed drying methods. Suitable cryoprotectants may include carbohydrates such as sugars (e.g., glucose) and may be added at a suitable concentration to the liquid culture (e.g., to at least about 1%, 2%, 5%, 10%, or 20% by mass). Cryoprotectants are known in the art. (See Morgan et al., 2006; and Hubalek, 2003, the contents of which are incorporated by reference in their entireties).

The bioaugmentation cultures subjected to the drying methods contemplated herein may comprise or consist of one or more of the foregoing described methanogens and exhibit specific methanogenic activity (SMA). After the cultures are dried and reconstituted with an aqueous solution, preferably the reconstituted cultures have an SMA (e.g., as measured against $H_2$:$CO_2$) that is at least about 10 ml $CH_4$/hr-g VSS (alternatively reported as $CH_4$/g VSS-h), or more preferably at least about 20, 30, 40, 50, 60, 70, 80, 90, 100, 125, 150, 175, 200, 225, or 250 ml $CH_4$/hr-g VSS. After the cultures are dried and reconstituted with an aqueous solution, preferably the reconstituted cultures have an SMA that is substantially similar to the SMA for the original culture prior to drying. In some embodiments, the reconstituted cultures have an SMA that is at least about 20%, 30%, 40%, 50%, 60%, 70%, 80%, 90%, or 95% of the SMA for the original culture prior to drying.

The methods disclosed herein may be utilized to reduce recovery time for an anaerobic digester system after upset, such as organic overload (e.g., such as propionate), temperature change, or toxicant exposure (e.g., such as oxygen). By bioaugmenting the anaerobic digester system with a methanogenic propionate-degrading culture, recovery time for resumed production of maximum methane by the anaerobic digester system is reduced.

In the disclosed methods, a culture comprising methanogens is added to an anaerobic digester system at a suitable rate as measured by volatile suspended solids (VSS)/L-day. Suitable rates may include rates of at least about 0.1 mgVSS/L-day, 0.2 mgVSS/L-day, 0.5 mgVSS/L-day, 1 mgVSS/L-day, 2 mgVSS/L-day, 5 mgVSS/L-day, 10 mgVSS/L-day, 20 mgVSS/L-day, 30 mgVSS/L-day, 40 mgVSS/L-day, 50 mgVSS/L-day, 60 mgVSS/L-day, 70 mgVSS/L-day, 80 mgVSS/L-day, 90 mgVSS/L-day, or 100 mgVSS/L-day. The culture may be added for a sufficient period of time to improve one or more performance parameters of the anaerobic digester system. In some embodiments, prior to adding the culture, partial pressure of hydrogen in the anaerobic digester system is at least $10^{-4}$ atm, $10^{-5}$ atm, or $10^{-6}$ atm (e.g., in the head space) and optionally the culture is added to the system for a period of time that is sufficient to reduce the partial pressure of hydrogen in the system to less than $10^{-4}$ atm, $10^{-5}$ atm, or $10^{-6}$ atm, respectively, preferably to less than at least $10^{-4}$ atm. In other embodiments, prior to adding the culture, the anaerobic digester system has a pH of no more than 6.8, 6.7, or 6.6, and optionally the culture is added to the system for a period of time that is sufficient to raise the pH above 6.8, 6.7, or 6.6, respectively. In further embodiments, prior to adding the culture, the anaerobic digester system has a propionic acid concentration of at least 500 mg/L, 600 mg/L, 700 mg/L, 800 mg/L, 900 mg/L, or 1000 mg/L, and optionally the culture is added to the system for a period of time that is sufficient to reduce the propionic acid concentration below 500 mg/L, 600 mg/L, 700 mg/L, 800 mg/L, 900 mg/L, or 1000 mg/L, respectively. In even further embodiments, prior to adding the culture, the system has a soluble chemical oxygen demand (SCOD) of at least 1000 mg/L, 2000 mg/L, 3000 mg/L, 4000 mg/L, or 5000 mg/L, and optionally the culture is added to the system for a period of time that is sufficient to reduce the SCOD to less than 1000 mg/L, 2000 mg/L, 3000 mg/L, 4000 mg/L, or 5000 mg/L, respectively. In even further embodiments, prior to adding the culture, the system may have a $CH_4$ production rate that is no more than about 20, 15, or 10 mL/day, and optionally the culture is added to the system for a period of time that is sufficient to increase the $CH_4$ production rate to at least about 15, 20, 25, 30, 35, 40, 45, or 50 mL/day.

ILLUSTRATIVE EMBODIMENTS

The following embodiments are illustrative and not intended to limit the claimed subject matter.

Embodiment 1

A method of increasing methane production in an anaerobic digester system, the method comprising adding a culture comprising hydrogenotrophic methanogens to the system.

Embodiment 2

The method of embodiment 1, wherein the hydrogenotrophic methanogens belong to the order Methanomicrobiales or to the order Methanobacteriales.

Embodiment 3

The method of embodiment 2, wherein the hydrogenotrophic methanogens comprise *Meihanospirillum hungatei*, or a related hydrogenotrophic methanogen.

Embodiment 4

The method of embodiment 3, wherein *Methanospirilhum hungatei* or the related hydrogenotrophic methanogen represent at least about 95% of hydrogenotrophic methanogens belonging to the order Methanomicrobiales in the culture.

Embodiment 5

The method of embodiment 2, wherein the hydrogenotrophic methanogens comprise *Methanobacterium beijingense* or a related hydrogenotrophic methanogen.

Embodiment 6

The method of embodiment 2, wherein the hydrogenotrophic methanogens comprise *Methanolinea tarda* or a related hydrogenotrophic methanogen.

Embodiment 7

The method of any of embodiments 1-6, wherein the culture comprises wastewater sludge.

Embodiment 8

The method of any of embodiments 1-7, wherein prior to being added to the system, the culture was grown in the presence of oxygen.

Embodiment 9

The method of any of embodiments 1-8, wherein prior to being added to the system, the culture was grown in the presence of an organic acid or a salt thereof.

Embodiment 10

The method of embodiment 9, wherein the organic acid is a straight chain or branched carboxylic acid having at least three carbon atoms.

Embodiment 11

The method of any of embodiments 1-10, wherein the culture optionally comprises syntrophic fatty acid oxidizing microorganism (e.g., microorganisms that are capable of metabolizing propionate).

Embodiment 12

The method of any of embodiments 1-11, wherein the culture is added to the system at a rate of at least about 0.1 mg volatile suspended solids (VSS)/L-day (or 0.2, 0.5, 1, 2, 5, 10, 20, 30, 40, 50, 60, 70, 80, 90, or 100 VSS/L-day).

Embodiment 13

The method of any of embodiments 1-12, wherein prior to adding the culture, partial pressure of hydrogen in the system is at least $10^{-6}$ atm (or at least $10^{-5}$ atm or at least $10^{-4}$ atm).

Embodiment 14

The method of embodiment 13, wherein the culture is added to the system for a period of time that is sufficient to reduce the partial pressure of hydrogen in the system to less than $10^{-6}$ atm (or less than $10^{-5}$ atm or less than $10^{-4}$ atm).

Embodiment 15

The method of any of embodiments 1-14, wherein prior to adding the culture, the system has a pH of no more than 6.8, 6.7, or 6.6.

Embodiment 16

The method of embodiment 15, wherein the culture is added to the system for a period of time that is sufficient to raise the pH above 6.6, 6.7, or 6.8.

Embodiment 17

The method of any of embodiments 1-15, wherein prior to adding the culture, the system has a propionic acid concentration of at least 500 mg/L, 600 mg/L, 700 mg/L, 800 mg/L, 900 mg/L, or 1000 mg/L.

Embodiment 18

The method of embodiment 17, wherein the culture is added to the system for a period of time that is sufficient to reduce propionic acid concentration below 500 mg/L, 600 mg/L, 700 mg/L, 800 mg/L, 900 mg/L, or 1000 mg/L.

Embodiment 19

The method of any of embodiments 1-18, wherein prior to adding the culture, the system has a soluble chemical oxygen demand (SCOD) of at least 1000 mg/L, 2000 mg/L, 3000 mg/L, 4000 mg/L, or 5000 mg/L.

Embodiment 20

The method of embodiment 20, wherein the culture is added to the system for a period of time that is sufficient to reduce the SCOD to less than 1000 mg/L, 2000 mg/L, 3000 mg/L, 4000 mg/L, or 5000 mg/L.

Embodiment 21

The method of any of embodiments 1-20, wherein prior to adding the culture, the system may have a $CH_4$ production rate that is no more than about 20, 15, or 10 mL/day.

Embodiment 22

The method of embodiment 21, wherein the culture is added to the system for a period of time that is sufficient to increase the $CH_4$ production rate to at least about 15, 20, 25, 30, 35, 40, 45, or 50 mL/day.

EXAMPLES

The following examples are illustrative and are not intended to limit the claimed subject matter.

Example 1

Reference is made to Schauer-Gimenez et al., "Bioaugmentation for improved recovery of anaerobic digesters after toxicant exposure," Water Research 44 (2010) 3555-3564, available on-line Apr. 7, 2010, the content of which is incorporated herein by reference in its entirety.

Abstract

Bioaugmentation was investigated as a method to decrease the recovery period of anaerobic digesters exposed to a transient toxic event. Two sets of laboratory-scale digesters (SRT=10 days, OLR=2 g COD/L-day), started with inoculum from a digester stabilizing synthetic municipal wastewater solids (MW) and synthetic industrial wastewater (WW), respectively, were transiently exposed to the model toxicant, oxygen. Bioaugmented digesters received 1.2 mg VSS/L-day of an $H_2$-utilizing culture for which the archaeal community was analyzed. Soon after oxygen exposure, the bioaugmented digesters produced 25-60% more methane than non-bioaugmented controls (p<0.05). One set of digesters produced lingering high propionate concentrations, and bioaugmentation resulted insignificantly shorter recovery periods. The second set of digesters did not display lingering propionate, and bioaugmented digesters recovered at the same time as non-bioaugmented controls. The difference in the effect of bioaugmentation on recovery may be due to differences between microbial communities of the digester inocula originally employed. In conclusion, bioaugmentation with an $H_2$-utilizing culture is a potential tool to decrease the recovery period, decrease propionate concentration, and increase biogas production of some anaerobic digesters after a toxic event. Digesters already containing rapidly adaptable microbial communities may not benefit from bioaugmentation, whereas other digesters with poorly adaptable microbial communities may benefit greatly.

Introduction

Bioaugmentation is the practice of adding specific microorganisms to a system to enhance a desired activity (Rittmann and Whiteman, 1994; Hairston et al., 1997; Deflaun and Steffan, 2002). In wastewater treatment, bioaugmentation has most frequently been applied to aerobic systems to increase the population of nitrifying bacteria after upsets from uncontrolled biomass loss, fluctuations in pH, toxic events, or temperature decrease (Rittmann and Whiteman, 1994; Abeysinghe et al., 2002; Satoh et al., 2003; Head and Oleszkiewicz, 2005). Bioaugmentation has also been used for other aerobic and anoxic applications (Hairston et al., 1997; Van Limbergen et al., 1998) and for soil and groundwater bioremediation (Deflaun and Steffen, 2002; Singer et al., 2005).

For anaerobic processes, bioaugmentation has been investigated at laboratory scale to improve start-up of new digesters (Saravanane et al., 2001a; Saravanane et al., 2001b), odor reduction (Duran et al., 2006; Tepe et al., 2008), and recovery after organic overload (Lynch et al., 1987). Also, anaerobic degradation rates of phenol and cresol (Charest et al., 1999; Tawfiki Hajji et al., 1999; Ouiot et al., 2000; Tawfiki Hajji et al., 2000), pentachlorophenol (Tartakovsky et al., 1999; Ouiot et al., 2002), 3-chlorobenzoate (Ahring et al., 1992), tetrachloroethylene (Horber et al., 1998) and fat, oil and grease (Cirne et al., 2006) have been increased using bioaugmentation. Anaerobic bioaugmentation with cellulose degraders increased methane production rates from hemicellulose by 30% (Angelidaki and Ahring, 2000) and cattle manure by as much as 93%; however, the significant increase in methane yield was only sustained for a limited time after inoculation (Mladenovska et al., 2001; Nielsen et al., 2007). The short improvement period highlights current challenges such as washout and out competition by indigenous organisms associated with bioaugmentation approaches (El Fantroussi and Agathos, 2005).

Bioaugmentation for rapid recovery of anaerobic digesters exposed to transient toxicants has not been reported to our knowledge. However, it may be advantageous to develop bioaugmentation as a recovery tool to address transient toxicity that can occur in full scale. Production and distribution of individual bioaugmentation cultures, each enriched to degrade a specific substrate, would be time consuming. It may be more practical to target a key, ubiquitous intermediate that accumulates during toxic events. In this regard, hydrogen ($H_2$) is a reasonable target intermediate since its degradation is often a rate-limiting step in methane production from many complex substrates. The $H_2$ concentration in anaerobic systems must be very low (<50 mM) for conversion of propionate and other intermediates to methane to be thermodynamically spontaneous (McCarty and Smith, 1986). Therefore, more rapid $H_2$ utilization can result in more complete conversion of propionate and other substrates to methane.

In this study, bioaugmentation using an $H_2$-utilizing culture was tested to determine if the approach would decrease the recovery time of anaerobic digesters exposed to a transient toxic event. A limited amount of the model toxicant, oxygen ($O_2$), was added to different digesters for a short period, and recovery of bioaugmented and non-bioaugmented digesters was compared.

Materials and Methods

Anaerobic Digesters

Two sets of anaerobic digesters were operated. Sets differed based upon the source of the initial inoculum employed. One set (MS systems) was inoculated with biomass from a bench-scale mesophilic anaerobic digester fed synthetic municipal sludge (Natural Choice Dog Food, NutroProducts, Inc., City of Industry, Calif.) with a 10-day solids retention time (SRT). The other set (WW systems) was inoculated with biomass from a bench-scale mesophilic anaerobic digester fed synthetic industrial wastewater (Instant Nonfat Dry Milk, Roundy's, Inc., Milwaukee, Wis.) with a 15-day SRT.

All digesters were 160-mL serum bottles containing 50 mL of active volume and operated at an SRT of 10 days and organic loading rate of 2 g COD/L-day. Five ml/day of effluent was removed and replaced with 5 mL/day of synthetic wastewater composed of nonfat dry milk (Roundy's Instant Nonfat Dry Milk) in basal nutrient medium. After one week, all digesters were exposed to the model toxicant, $O_2$, by injecting 10 ml/day of air (approximately 1 atm, 20° C.) into each system for seven days. Bioaugmented digesters received 1.2 mg of volatile suspended solids (VSS) per liter of digester per day (mg VSS/L-day) of an enrichment culture described below. Control digesters received an abiotic version of the enrichment culture that had been inactivated by autoclaving.

Culture Used for Bioaugmentation

The methanogenic culture used for bioaugmentation was developed using biomass from a mesophilic municipal anaerobic digester (South Shore Wastewater Treatment Plant, Milwaukee, Wis.) treating primary sludge and was enriched by feeding $H_2$, carbon dioxide ($CO_2$), and glucose in the basal medium as well as limited $O_2$ over three months. Two liters of biomass were maintained in a 2.5-L glass reactor continuously stirred with a magnetic stir bar and in a temperature controlled room (35±2° C.). The culture was sparged daily with gas (1:1 v/v $H_2:CO_2$) for approximately 20 s and sealed with a rubber stopper. The $CO_2$ content was greater than that of the stoichiometric amount (i.e., 4:1 v/v $H_2:CO_2$) so as to maintain the culture pH near 7. A glass tube was inserted through the stopper and connected to a 5-L Tedlar bag that was emptied daily and refilled with the $H_2:CO_2$ mixture. The liquid effluent (133 mL) was removed once per day to maintain an SRT and hydraulic retention time (HRT) of 15 days. Effluent was replaced with 133 mL of basal medium containing 84 mg glucose. Approximately 80 mg $O_2$/day was added by injecting 280 mL of ambient air (approximately 1 atm, 20° C.) directly into the vessel headspace with a plastic syringe. This mass of $O_2$ satisfied very little (i.e., 6%) of the $H_2$ oxygen demand. Therefore, the culture dissolved oxygen concentration was expected to be zero, and the presence of strict anaerobes (e.g., methanogens) was anticipated.

Basal Nutrient Medium

Basal nutrient medium contained the following [mg/L]: $NH_2Cl$ [400]; $MgSO_2.6H_2O$ [250]; KCl [400]; $CaCl_2.2H_2O$ [120]; $(NH_4)_2HPO_4$ [80]; $FeCl_2.6H_2O$ [55]; $CoCl_2.6H_2O$ [10]; K1 [10]; the trace metal salts ($MnCl_2.4H_2O$, $NH_4VO_3$ $CuCl_2.2H_2O$, $Zn(C_2H_3O_2)_2.2H_2O$, $AlCl_2.6H_2O$, $NaMoO_4.2H_2O$, $H_3BO_3$, $NiCl_2.6H_2O$, $NaWO_4.2H_2O$, and $Na_2SeO_2$) [each at 0.5]; yeast extract [100]; $NaHCO_2$ [5000]; and resazurin [1].

Specific Methanogenic Activity (SMA) Assays

Methanogenic activity assays were conducted in triplicate at 35° C., 250 rpm using an incubator shaker (model C25KC, New Brunswick Scientific, Edison, N.J.). Published protocols for the substrates calcium acetate (Angelidaki et al., 2007) as well as $H_2:CO_2$ (Coates et al., 1996) were used. All assays were performed under anaerobic conditions in 160 mL serum bottles with 25 mL of enrichment culture having 100-400 mg/L VSS. Culture samples were collected from reactors on three consecutive days and composited for testing. The VSS concentration was determined at the beginning and end of activity tests and the average of the two values was employed for specific activity calculations.

For acetate activity assays, the substrate was added to serum bottle contents to achieve 10 g/L of calcium acetate. Bottles were then sparged with $O_2$-free gas (7:3 v/v $N_2:CO_2$), closed with red butyl rubber septa and incubated. For hydrogenotrophic activity assays, serum bottles were sparged with gas (4:1 v/v $H_2:CO_2$) and closed with solid Balch-type butyl rubber stoppers (Geo-Microbial Technologies, Inc., Ochelata, Okla.) and aluminum-crimped seals. Immediately thereafter, 100 mL of the $H_2:CO_2$ gas blend at ambient pressure and temperature was injected through the stopper using a syringe and 23-gauge needle; then the bottles were incubated. Blanks were prepared similarly, but no substrate was added. These bottles were sparged with $H_2$-free gas (7:3 v/v $N_2:CO_2$) and sealed. Bottle headspace volume was measured at ambient pressure (approximately 1 atm) for 1-5 days. Volume was measured by inserting the needle of a glass syringe with wetted barrel. Syringe content was re-injected into the serum bottle after volume measurement. Headspace $CH_4$ content was measured using gas chromatography (GC).

For activity, maximum methane production rate (mL $CH_4$/h) was determined by linear regression of the initial, linear portion of a plot of cumulative methane production versus time. SMA values (mL $CH_4$/g VSS-h) were calculated by dividing maximum methane production rate values by average VSS mass. For hydrogenotrophic activity, maximum methane production rate (mL $CH_4$/h) was determined as described by others (Coates et al., 1996). Briefly, the decrease in headspace volume observed at any time was corrected by adding the volume of additional gas measured in blanks. The sum was divided by four based upon the stoichiometry of hydrogenotrophic methanogenesis (i.e., for every 4 mol of $H_2$ and 1 mol of $CO_2$ consumed, 1 mol of $CH_4$ is produced) to yield the cumulative volume of methane produced. Maximum methane production rates and SMA values against $H_2:CO_2$ were then determined by linear regression as described for acetate activity.

Analytical Methods

Samples for propionate and soluble COD (SCOD) concentration analysis were centrifuged at 14,000×9 for 10 min (Galaxy 14D centrifuge, VWR International, West Chester, Pa.) and filtered using a 0.45 pm filter (Whatman International Ltd., Maidstone, England). Propionate was measured in filtrate using a GC (Series 600, GOW-MAC Instrument Co., Bethlehem, Mass.) equipped with a flame ionized detector (FID) and a packed stainless steel column 6'×¼" (Alltech Associates, Inc., Deerfield, Ill.). Helium was used as the carrier gas at a flow of 50±1 ml/min. The temperature of the injector and detector was 200° C. and the oven temperature was 150° C. The supernatant was stored in 4-mL vials with a minimal amount of phosphoric acid to acidify the sample to a pH of <2. SCOD was measured in filtrate by standard methods (APHA et al., 1998). The biogas quantity produced in digesters was measured daily using a glass syringe with a wetted glass barrel. The headspace gas composition ($CH_4$, $CO_2$ and $N_2$ concentrations) was determined using a GC equipped with a thermal conductivity detector (TCD) and a packed column (CTR I column, Alltech Associates, Inc., Deerfield, Ill.). Helium was used as the carrier gas at a flow of 30±2 ml/min with injector and detector temperatures of 120° C. and oven temperature of 38° C. The pH was measured using a bench-top pH meter (Orion Model 720A, Thermo Fisher Scientific, Inc., Waltham, Mass.) and a general-purpose pH electrode (Orion, Thermo Fisher Scientific, Inc., Waltham, Mass.).

Statistical Analyses

All statistical analyses were completed using the "t-test: two sample assuming unequal variances" function in Microsoft Excel (Excel, 2004 for Mac, Version 11.5.5). Each set of replicates was analyzed in order to obtain mean and variance values for the t-test function.

Archaeal Community Analysis

DNA extraction. DNA was extracted from the bioaugmentation culture by removing and centrifuging (IEC Centra-4B, International Equipment Company) a 50-mL volume for 10 min at 2500×g. The supernatant was then decanted and a 0.75-mL thickened biomass sample was used for DNA extraction (PowerSoil™ DNA Isolation Sample Kit, MoBio Laboratories, Carlsbad, Calif.). The standard protocol provided in the kit was followed with one exception; the Alternative Lysis Method was used (a 1 min vortex followed by a 10 min incubation at 70° C., after adding Solution C1). The presence of DNA was confirmed and estimates of its concentration were made using gel electrophoresis (1% agarose) stained with ethidium bromide (0.8 µl/mL) (Sambrook and Russell, 2001). A DNA ladder containing 40-ng/µl Lambda DNA, HindIII cut and in some cases 30-ng/µl phi X174, HaeIII cut was used as a marker.

Polymerase Chain Reaction.

A fragment of the 16S rRNA genes was amplified with ArchF (5'-TTCCGGTTGATCCYGCCGGA-3' (SEQ ID NO:7)) and ArchR (5'-YCCGGCGTTGAMTCCAATT-3' (SEQ ID NO:8)) (DeLong, 1992) using either a Biometra Tpersonal (Biometra, Goettingen, Germany) or Bio-Rad PTC200 DNA Engine Cycler thermal cycler (Bio-Rad, Hercules, Calif.). All PCR amplification mixtures (100 µL) contained EconoTaq® PLUS 2× Master Mix (Lucigen Corporation, Middleton, Wis.) and 0.1 µM of each primers. The amplification method parameters were as follows: 94° C. for 2 min, 94° C. for 30 s, 55° C. for 30 s, 72° C. for 2 min for 34 cycles and 72° C. for 13 min.

Cloning.

The 16S rRNA gene amplified products were cloned into One Shot® Mach1™-T1® Chemically Competent *Escherichia coli* cells using the TOPO TA Cloning® Kit for Sequencing according to the manufacturer's instructions Invitrogen, Carlsbad, Calif.). Bacteria were inoculated to S-Gal™/KanamyciniLuria-Bertani Broth Agar Blend (Sigma-Aldrich, St. Louis, Mo.) plates containing 50 mg/mL ampicillin and incubated at 37° C. for one day. Colonies were picked using light/dark screening and directly amplified with PCR using PucF (5'-GGAATTGTGAGCGGATAACA-3' (SEQ ID NO:9)) and PucR (5'-GGCGATTAAGTTGGGTAACG-3' (SEQ ID NO:10)) primers. The PCR thermal cycling parameters were as follows: 94° C. for 2 min, 94° C. for 30 s, 55° C. for 30 s, 72° C. for 1 min for 30 cycles, and 72° C. for 9 min. The presence of amplified PCR products was confirmed using agarose gel electrophoresis as previously described.

PCR Purification, Sequencing and Phylogenetic Analysis.

Samples were cleaned using the UltraClean™ PCR Clean-Up™ kit according to manufacturers' instructions (MoBio Laboratories, Carlsbad, Calif. PCR products of 50 archaeal clones from the bioaugmentation culture were sequenced (University of Chicago Cancer Research Center DNA Sequencing Facility, Chicago, Ill.). The forward and reverse sequences were analyzed using FinchTV (Geospira Inc., Seattle, Wash.) and Vector NTI (Invitrogen, Carlsbad, Calif.) and consensus sequences were assembled. Vector sequences were removed using the Basic local Alignment Search Tool (BLAST) to match vector sequences in the UniVec Database with the sample sequences in a manner identical to VecScreen (Altschul et al., 1997). Chimera detection analysis was performed using Chimera Check, version 2.7 (Cole et al., 2005) of the Ribosomal Database Project (RDP) and sequences determined to be chimeras were removed from further analysis. The complete consensus sequences were submitted to BLAST to identify similar 16S rRNA gene sequences (Altschul et al., 1997). The consensus and select reference sequences were aligned using the RDP (Cole et al., 2007). A distance matrix based on the Kimura 2-parameter algorithm was constructed using the Phylogeny Inference Package (PHYLIP) dnadist program (Felsenstein, 2005). Bootstrap analyses were performed to generate 100 bootstrap samples. Neighbor joining, maximum parsimony and maximum likelihood trees were created using PHYLIP. Consensus trees were generated with PHYLIP's consense program, using the extended majority rule. Resulting trees were visualized using FigTree v1.1.2 (Rambaut, 2008), compared and were similar. The neighbor-joining tree was presented in the text. The Fitch-Margoliash algorithm was used to add the distances to the bootstrapped trees. The SeqMatch program on the RDP website was used (Cole et al., 2007) to identify the taxonomic classifications if the 16S rRNA gene sequence similarity to known microorganisms was less than 95%. To examine the richness of the archaeal community in the bioaugmentation culture, rarefaction analysis, Chao1 richness estimates and Shannon indices were constructed using DOTUR (Schloss and Handelsman, 2005). Operational taxonomic units (OTUs) were defined as sequence groups in which sequences differed by 2% or less.

Nucleotide sequence accession numbers. Sequences from the clone library described above were deposited in the GenBank database under accession numbers GU196151-GU196192.

Results

Bioaugmentation Culture Archaeal Community Analysis

Figure 2:
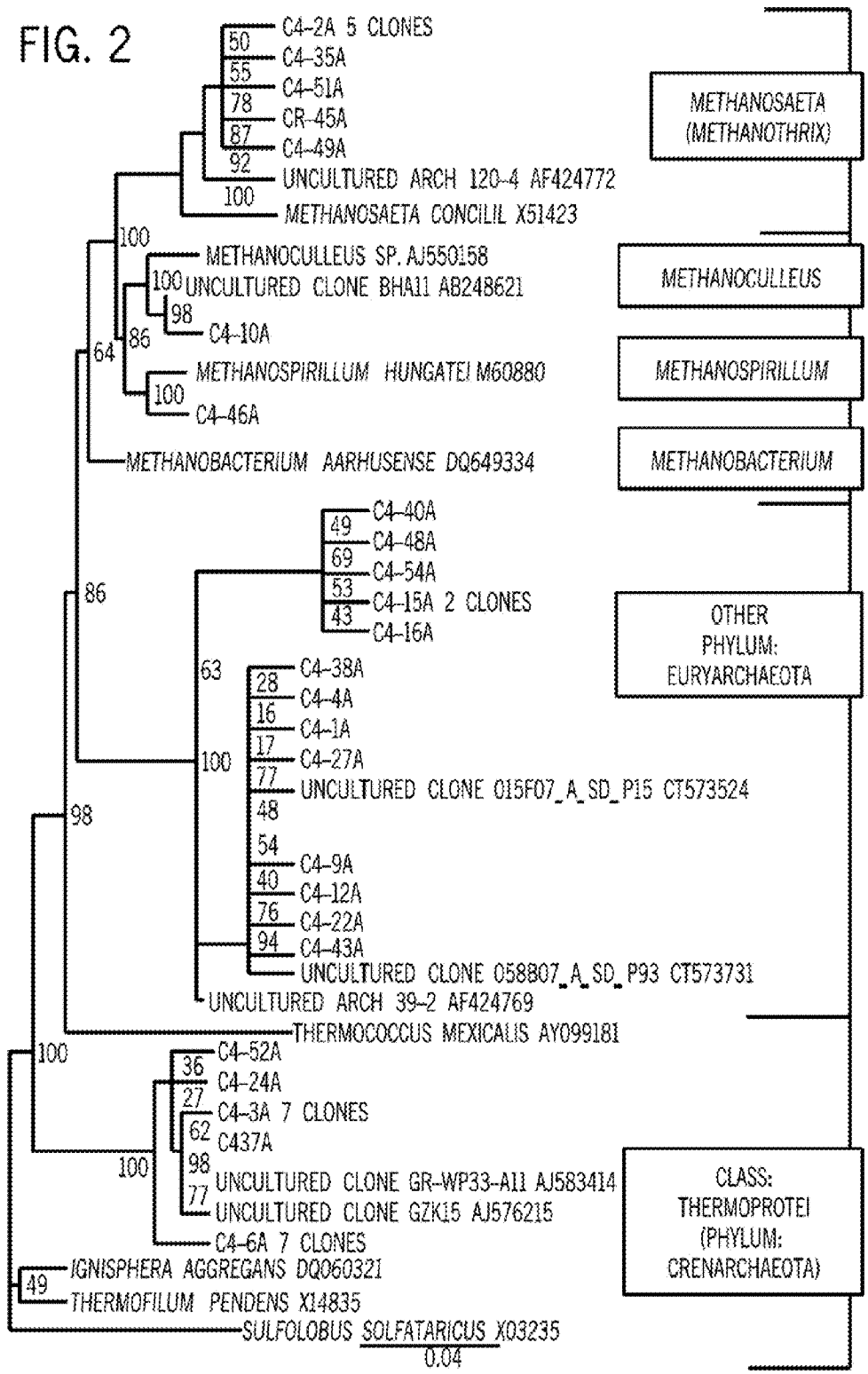
FIG. 2 illustrates a phylogenetic analysis of a bioaugmentation culture archaeal clone library. Calculations were based on the neighbor-joining algorithm (bootstrap number –100). Numbers at nodes represent bootstrap values. The scale bar represents the number of nucleotide changes per sequence position. The tree was rooted to the organism *Sulfolobus solfataricus* (X03235).

An archaeal clone library was constructed for the bioaugmentation culture. Of the 50 sequences, 8 were chimeric and removed from further analysis. The rarefaction curve (see FIG. 1) indicated that the archaeal coverage was 83% (Chao1 richness estimates). Also, the Shannon indices showed that the archaeal clone library was not very heterogeneous (1.25). Phylogenetic analysis of Archaea in the bioaugmentation culture (see FIG. 2) showed sequences that were related to three methanogenic genera (*Methanosaeta, Methanoculleus,* and *Methanospirllum*). Nine sequences grouped in the genus-*Methanosaeta* (96% sequence similarity) and accounted for 21% of the Archaean sequences sampled. According to the SMA assay results, the activity against acetate was relatively low (SMA ~0.25±0.07 mL $CH_4/gVSS$-h) even though *Methanosaeta* was found in high relative abundance.

Because $H_2$ and $CO_2$ were fed to the bioaugmentation culture, it was anticipated that most of the methanogen 16S rRNA gene sequences would relate to $H_2$ utilizers. But only one sequence (C4-46A) was closely related to the $H_2$-utilizer *Methanospirillum hungatei* (98% sequence similarity, GenBank accession number: M60880) and only one sequence ($C_{4-10}A$) was closely related to the $H_2$-utilizer *Methanoculleus* sp. dm2 (97% sequence similarity, GenBank accession number: A)550158). Although these sequences accounted for only 5% of the clone library, the average SMA value against $H_2$ was relatively high (47±30 mL $CH_4$/g VSS-h). It is possible that the unknown Archaean sequences discussed below that made up 74% of the community were related to $H_2$ utilizers.

A number of unknown Archaean sequences were found. For example, 14 sequences could only be classified as Euryarchaeota (33% of the community) and were most similar to an uncultured clone sequenced from a municipal mesophilic anaerobic digester (99% similarity) (Chouari et al., 2(05). In addition, 17 sequences could only be placed in the phylum Crenarchaeota, class Thermoprotei (41% of the community) (see FIG. 2). These sequences were most similar to an uncultured clone sequence from leachate in a municipal solid waste landfill (98% similarity) (Huang et al., 2003).

Bioaugmented Digester Performance.

Figure 3:
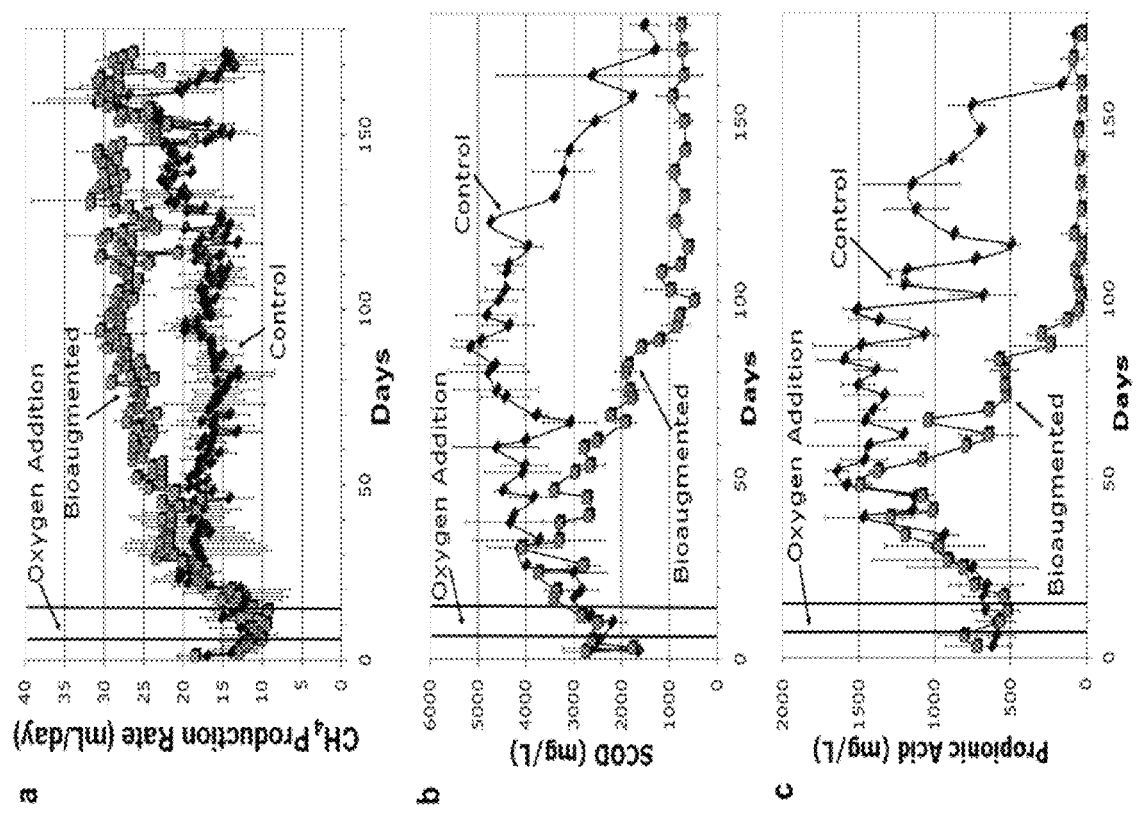
FIG. 3 illustrates results of bioaugmented and control MS digesters: (a) methane production; (b) SCOD; (c) effluent propionic acid. Error bars represent standard deviation of duplicate digesters.
Figure 4:
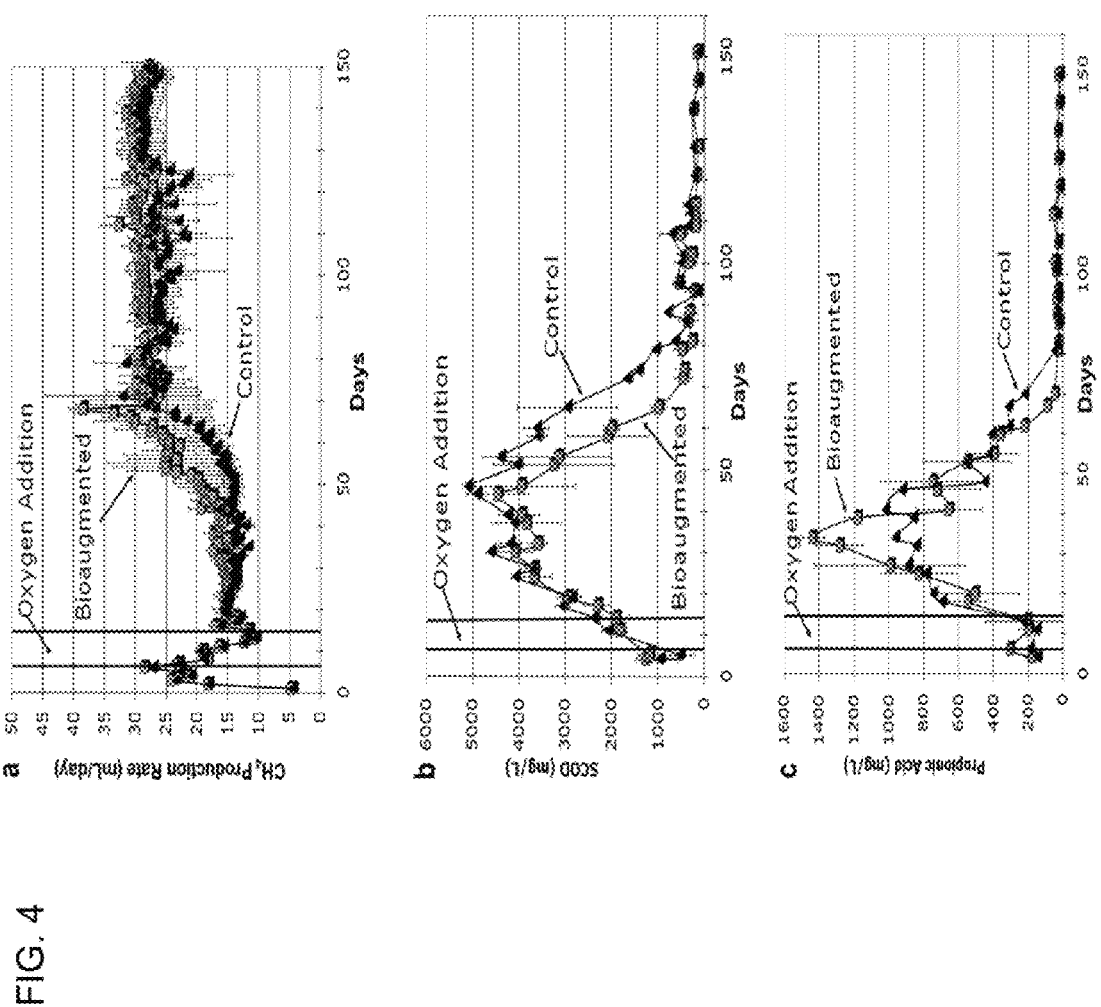
FIG. 4 illustrates results of bioaugmented and control digesters treating synthetic wastewater (WW): (a) methane production; (b) SCOD; (c) propionic acid. Error bars represent standard deviation of four replicate digesters.

Average $CH_4$ production rates for bioaugmented and control digesters were similar before and during air addition (see FIGS. 3a and 4a). After air addition, however, the bioaugmented digesters produced significantly more $CH_4$ than the respective controls ($p<0.05$). The higher $CH_4$ production rate for bioaugmented digesters was evident on Days 25-170 for MS systems (see FIG. 3a) and Days 45-70 for WW systems (see FIG. 4a). For MS systems, the average bioaugmented $CH_4$ production rate was approximately 60% greater than that of the non-bioaugmented controls during this period. For WW systems, the bioaugmented $CH_4$ production rate was approximately 25% greater. It should be noted that the apparent decrease in $CH_4$ production rate on Day 148 for the MS systems was due to leaking septa. These septa were replaced and the measured average $CH_4$ production increased in both bioaugmented and control digesters from Day 155 to 161 (27±3 mL $CH_4$/day the control and 28±2 mL $CH_4$/day in the bioaugmented digesters). For both MS and WW systems, the average pH of all digesters was approximately 7.20 before air addition. The pH then decreased during and immediately after air addition with the lowest average pH values of 6.60 observed between Days 16 and 18 and between Days 39 and 49 for MS and WW systems, respectively. Subsequently, digester pH values increased to 7 or greater.

Effluent SCOD.

The average effluent SCOD from all digesters significantly increased after air addition, peaking at approximately 5000 mg/L (see FIGS. 3b and 4b). Subsequently, the average SCOD decreased below 2000 mg/L, with the decrease more rapid in bioaugmented systems as compared to controls (see FIGS. 3b and 4b).

For MS systems, the average SCOD decreased in the bioaugmented digesters from 4000 mg/L (Day 30) to 600 mg/L during a 2.5-month period, and remained relatively low and constant for the remainder of the investigation (see FIG. 3b). In contrast, the average effluent SCOD of the non-bioaugmented digesters remained greater than 2000 mg/L for over five months, as can be seen in FIG. 3b. In addition, effluent SCOD from the non-bioaugmented digesters was significantly higher than that of the bioaugmented digesters at the conclusion of the investigation (1540±290 mg/L versus 780±210 mg/L, respectively).

For WW systems, the high SCOD concentrations persisted during a recovery period of only three months in contrast to the five-month recovery for MS systems (see FIG. 4b). After Day 120, both bioaugmented and control digesters exhibited low average SCOD concentrations of 200 mg/L in WW systems (see FIG. 4b).

Effluent Propionate.

Effluent propionate concentrations from all digesters increased from less than 600 to greater than 1000 mg/L during the four week period after air was added, then began to decrease (see FIGS. 3c and 4c). For MS systems, propionic acid in bioaugmented digesters eventually decreased to 60±40 mg/L (Day 97), but lingered in control digesters and did not decrease until Day 124 (see FIG. 3c). For WW systems, on the other hand, bioaugmented and control digesters exhibited similar effluent propionate concentrations over time (see FIG. 4c).

Recovery Periods.

Figure 5:
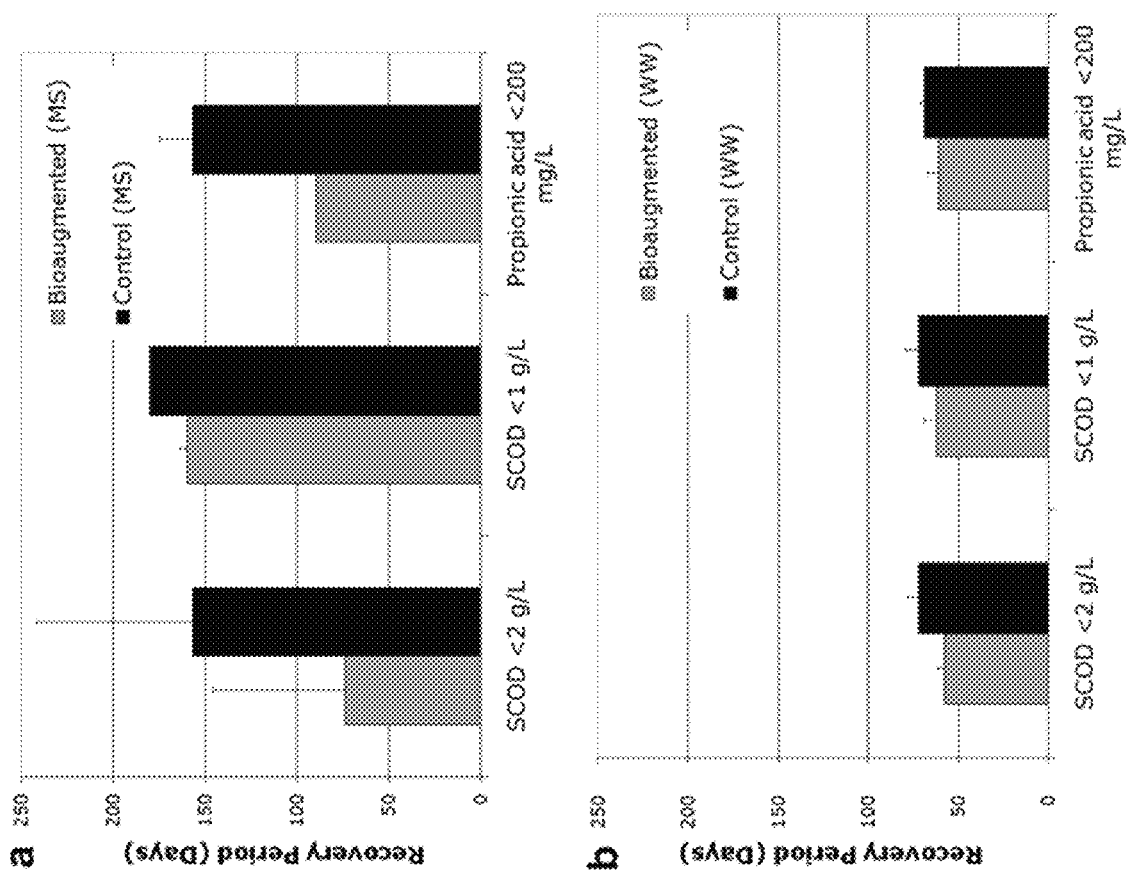
FIG. 5 illustrates a comparison of bioaugmented and control system recovery periods. Average bioaugmented and control digester recovery periods for MS systems fed synthetic municipal wastewater sludge (MS) (a); and WW systems (b). Recovery periods for MS control and bioaugmented systems were different, whereas that for WW systems were not ($p<0.05$). Error bars represent standard deviation.
Figure 6:
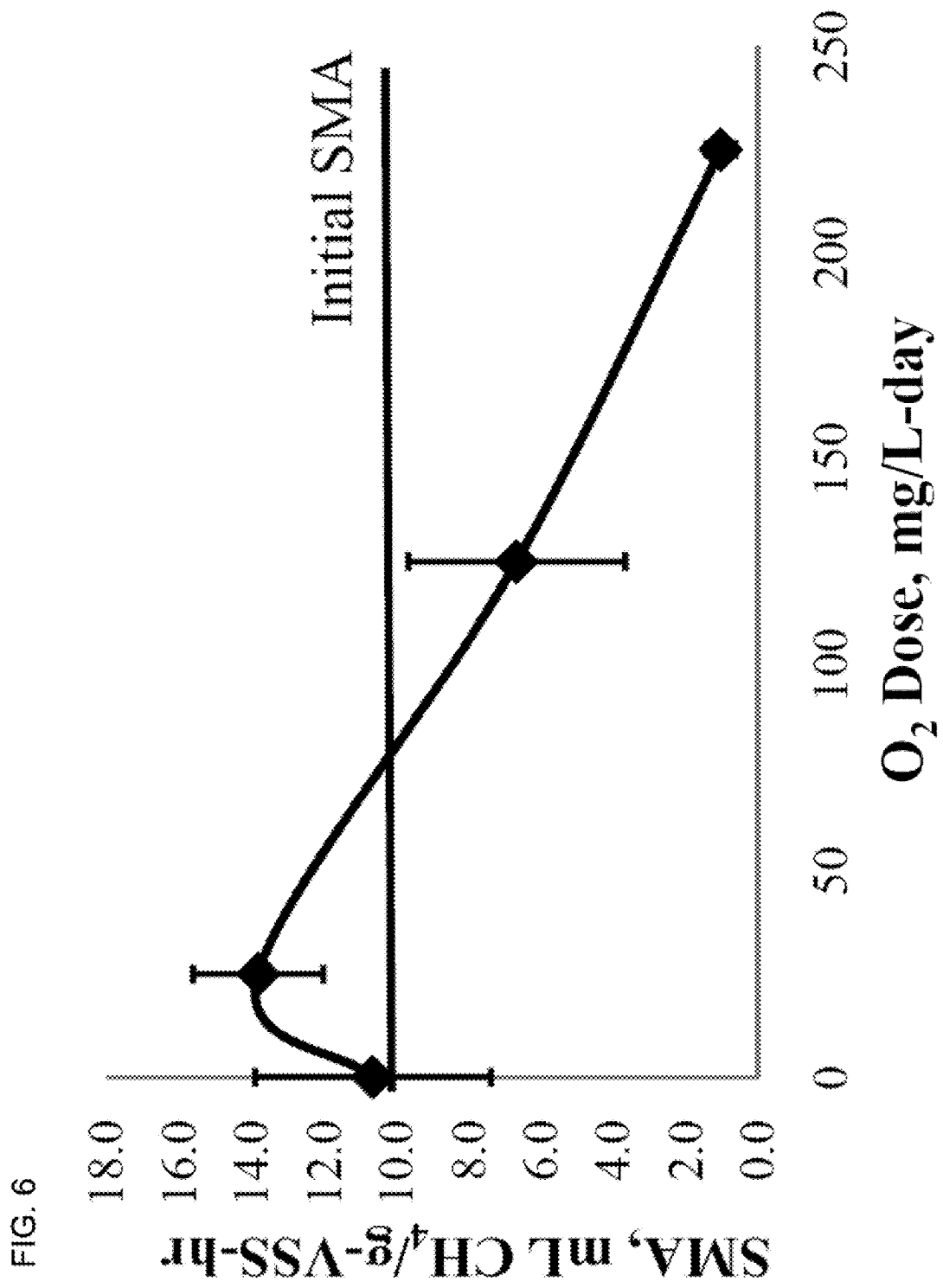
FIG. 6 illustrates the effect of oxygen on SMA against propionate after enrichment. Error bars represent standard deviations among three (3) replicates.

For comparison, recovery periods were defined as the time required after air addition for the average effluent concentration of SCOD or propionate to decrease below specified threshold concentrations. After the recovery period, no subsequent increase above the threshold concentration was observed. For SCOD, threshold concentrations of 1 g/L and 2 g/L were chosen. For propionate, a threshold concentration of 200 mg/L was employed. The recovery periods were significantly shorter for bioaugmented digesters in comparison to controls for MS systems ($p<0.05$), but were not shorter for WW systems (see FIG. 5). MS bioaugmented digesters achieved an SCOD concentration below 2 g/L over 80 days (i.e., 8 SRTs) before the controls (see FIG. 5); in addition, the propionic acid concentrations in bioaugmented digesters declined below 200 mg/L approximately 70 days before that of the controls (Day 90±0 versus Day 157±18). In contrast, the WW bioaugmented and non-bioaugmented digesters both recovered approximately 2 months after oxygen exposure.

Discussion

Sequences most similar to those of $H_2$-utilizing methanogens (*Methanosaeta, Methanoculleus*, and *Methanospirillum*) were found in the bioaugmentation culture, as expected. Sequences grouped in the genus *Methanosaeta* were also found, and accounted for 21% of the Archaean sequences sampled. These acetoclastic methanogens have also been found in other anaerobic treatment systems (Macario and de Macario, 1988; Grotenhuis et al., 1991; Raskin et al., 1995; Griffin et al., 1998; Sekiguchi et al., 1998; McHugh et al., 2003; Leclerc et al., 2004). Glucose in the feed to the bioaugmentation culture ostensibly resulted in the presence of acetoclastic methanogens in the $H_2$-rich environment. Fernandez et al. (2000) found that *Methanosaeta* accounted for approximately 20% of the total methanogen community in some anaerobic digesters fed glucose as the sole carbon source. A large majority of the clones (i.e., 74%) were unknown Archaean sequences. For example, 33% of the sequences could only be classified as Euryarchaeota and were most similar to an uncultured clone sequenced from a municipal mesophilic anaerobic digester (99% similarity) (Chouari et al., 2005). In addition, 41% of the clones could only be placed in the phylum Crenarchaeota, class Thermoprotei. These sequences were most similar to an uncultured clone sequence from leachate in a municipal solid waste landfill (98% similarity) (Huang et al., 2003). The unknown Archaean sequences could not be further classified taxonomically and it is difficult to suggest what role they play in the microbial community. However, the Euryarchaeota could be methanogens.

Bioaugmentation of anaerobic processes has been reported to improve degradation of specific organics, start-up of new digesters, odor reduction, and recovery of organically overloaded systems at laboratory scale. When we perturbed two different anaerobic digester sets (MS and WW) by exposing them to air, bioaugmentation with a methanogenic, $H_2$-utilizing culture resulted in higher methane production rates. In addition, SCOD concentrations decreased more rapidly in bioaugmented versus non-bioaugmented digesters. O'Flaherty et al. (1999) and O'Flaherty and Colleran (1999) also found that bioaugmentation increased the COD removal rate in anaerobic systems when toxicity was exerted; adding sulfate-acclimated biomass resulted in a 58% increase in steady-state COD removal for a laboratory anaerobic hybrid reactor treating high sulfate wastewater (concentration of 4 g/L; COD:sulfate ratio of 3:1).

When effluent propionate concentrations and recovery periods were compared, bioaugmentation outcomes varied. Bioaugmentation resulted in significantly shorter recovery periods for MS systems, for which non-bioaugmented controls continued to produce chronically high, lingering propionate concentrations after the toxic event. In contrast, non-bioaugmented WW systems did not accumulate lingering high propionate concentrations, and bioaugmentation did not result in significantly shorter recovery. The addition of $H_2$ utilizers ostensibly reduced digester $H_2$ concentration, resulting in more complete propionate degradation in MS systems. The contradiction in MS and WW results may be due to differences in microbial communities for the two digester inocula (MS and WW) employed. Others reported that recovery periods of anaerobic digesters subjected to organic overload differed based upon the microbial communities initially present (Hashsham et al., 2000; Fernandez et al., 2000). Microbial communities in which the number of individual members is approximately the same (i.e., high evenness) have been shown to accomplish higher substrate conversion when exposed to high-salts stress as compared to communities in which a few organisms dominate the population (i.e., low evenness) (Wittebolle et al., 2009). It is possible that the MS system microbial community could rapidly adapt after the toxic event to degrade propionate whereas the WW system could not.

Therefore, the microbial community structure (i.e., richness, evenness, etc.) within an existing biological system is just as important as the community structure of any culture added when bioaugmentation is practiced. Digester microbial communities before bioaugmentation were not analyzed herein. In one review of laboratory and full-scale aerobic literature, 30% of the reports showed no benefit when bioaugmentation was practiced (Stephenson and Stephenson, 1992). One reason for the unsuccessful applications may be because biological systems with rapidly adaptable microbial communities will not benefit from bioaugmentation, whereas systems with low microbial diversity or evenness may benefit greatly.

Conclusions

Bioaugmentation with an $H_2$-utilizing culture is a potential tool to decrease the recovery period and increase biogas production of some anaerobic digesters after a toxic event. Bioaugmentation resulted in decreased recovery times for digesters that tended to produce chronically high, lingering propionate concentrations after air exposure. In contrast, recovery time was not significantly shortened for digesters that did not produce lingering propionate. This contradiction may be due to differences between microbial communities of the two digester inocula employed. Digesters already containing rapidly adaptable microbial communities may not benefit from bioaugmentation, whereas other digesters with poorly adaptable microbial communities may benefit greatly. Analysis of microbial communities in both bioaugmentation cultures and digester biomass is suggested to develop bioaugmentation applications. In the future, the community structures of various digesters as well as bioaugmentation cultures should be determined and their response to bioaugmentation during toxicity events or periods of elevated propionate should be compared.

References for Example 1

Abeysinghe, D. H., De Silva, D. G. V., Stahl, D. A., Rittmann, B. E., 2002. The effectiveness of bioaugmentation in nitrifying systems stressed by a washout condition and cold temperatures. Water Environment Research 74 (2), 187-1.99.

Ahring. B. K., Christiansen, N., Mathrani, I., Hendriksen, H. V., Macario, A. J. L., Conway de Macario, E., 1992. Introduction of a de novo bioremediation ability, aryl reductive dechlorination, into anaerobic granular sludge by inoculation of sludge with *Desulfomonile tiedjei*. Applied and Environmental Microbiology 58 (11), 3677-3682.

Altschul, S. F., Madden, T. L., Schaffer, A. A., Zhang,)., Zhang, Z., Miller, W., Lipman, D.)., 1997. Gapped BLAST and PSI-BLAST: a new generation of protein database search programs. Nucleic Acids Research 25, 3389-3402.

American Public Health Association (APHA), American Waterworks Association (AWWA), Water Environment Federation (WEF)., 1998. Standard Methods for the Examination of Water and Wastewater, 20th ed. McGraw-Hill Companies, Inc., New York, N.Y.

Angelidaki, L, et al., Oct. 9-10, 2007. Anaerobic Biodegradation, Activity and Inhibition (ABAI). Task Group Meeting. Prague, Czech Republic.

Angelidaki, L, Ahring, B. K., 2000. Methods for increasing the biogas potential from the recalcitrant organic matter contained in manure. Water Science and Technology 41 (3), 189-194.

Charest, A., et al., 1999. Removal of phenolic compounds from a petrochemical effluent with a methanogenic consortium. Canadian journal of Microbiology 45 (3), 235-241.

Chouari, R., et al., 2005. Novel predominant archaeal and bacterial groups revealed by molecular analysis of an anaerobic sludge digester. Environmental Microbiology 7 (8), 1104-1115.

Cirne, D. G., Bjornsson, L., Alves, M., Mattiasson, B., 2006. Effects of bioaugmentation by an anaerobic lipolytic bacterium on anaerobic digestion of lipid-rich waste journal of Chemical Technology and Biotechnology 81, 1745-1752.

Coates, J. D., Coughlan, M. F., Colleran, E., 1996. Simple method for the measurement of the hydrogenotrophic methanogenic activity of anaerobic sludges. Journal of Microbiological Methods 26, 237-246.

Cole, J. R., Chai, B., Farris, R. J., Wang, Q., Kulam-Syed Mohideen,

A. S., McCarrell, D. M., Bandela, A. M., Cardenas, E., Garrity, G. M., Tiedje, J. M., 2007. The ribosomal database project (RDP-II: introducing myRDP space and quality controlled public data. Nucleic Acids Research 35 (Database Issue), D169-D172.

Cole, J. R., Cha~B., Farris, R. J., Wang, Q., Kulam, S A, McGarrell, D. M., Garrity, G. M., Tiedje, J. M., 2005. The ribosomal database project (RDP-1D: sequences and tools for high-throughput rRNA analysis. Nucleic Acids Research 33 (Database Issue), D294, D2%.

Deflaun, M. F., Steffan, R. J., 2002. Bioaugrnentation. In: Bitton, G. (Ed.), Encyclopedia of Environmental Microbiology vol. 1. Wiley-Interscience, New York. N.Y., pp. 434-442.

DeLong. E. F., 1992. Archaea in costal marine environments. Proceedings of the National Academy of Sciences 89, 5685-5689.

Duran, M., Tepe, N., Yurtsever, D., Punzi, V. L., Bruno, C., Mehta, R. }., 2006. Bioaugmenting anaerobic digestion of biosolids with selected strains of *Bacillus, Pseudomonas*, and *Aetinomycetes* species for increased methanogenesis and odor control Applied Microbiology and Biotechnology 73, 960-966.

El Fantroussi, S., Agathos, S. N., 2005. Is bioaugmentation a feasible strategy for pollutant removal and site remediation? Current Opinion in Microbiology 8 (3), 268-275.

Felsenstein, J., 2005. PHYLIP (Phylogeny Inference Package) Version 3.6. Distributed by the author. Department of Genome Sciences, University of Washington, Seattle.

Fernandez, A S., Hashsharn, S A, Dollhopf, S. L., Raskin, L., Glagoleva, O., Dazzo, F. B., Hickey, R. F., Criddle, C. S., Tiedje, J. M., 2000. Flexible community structure correlates with stable community function in methanogenic bioreactor communities perturbed by glucose. Applied and Environmental Microbiology 66 (9), 405B-4067.

Griffin, M. E., McMahon, K. D., Mackie, R. I., Raskin, L., 1998. Methanogenic population dynamics during start-up of anaerobic digesters treating municipal solid waste and biosolids. Biotechnology and Bioengineering 57 (3), 342-355.

Grotenhuis, J. T. C., Smit, M., Plugge, C. M., Yuansheng. X., vanLammeren, A. A. M., Starns, A J. M., Zehnder, A J. B., 1991. Bacteriological composition and structure of granular sludge adapted to different substrates. Applied and Environmental Microbiology 57 (7), 1942-1949.

Guiot, S. R., Tartakovsky. 8., Lanthier, M., Levesque, M. j., Manuel, M. F., Beaudet, R., Greer, C. W., Villemur, R. t 2002. Strategies for augmenting the pentachlorophenol degradation potential of UASB anaerobic granules. Water Science and Technology 45 (10), 35-41.

Guiot, S. R., Tawfiki-Hajji, K., Lepine, F., 2000. Immobilization strategies for bioaugmentation of anaerobic reactors treating phenolic compounds. Water Science and Technology 42 (5-6), 245-250.

Hashsham, S A, Fernandez, A.5., Dollhopf, S. L., Dazzo, F. B., Hickey, R. F., Tiedje, J. M., Criddle, E. S., 2000. Parallel processing of substrate correlates with greater functional stability in methanogenic bioreactor communities perturbed by glucose. Applied and Environmental Microbiology 66 (9), 4050-4057.

Head, M. A., Oleszkiewicz, M. A., 2005. Bioaugmentation with nitrifying bacteria acclimated to different temperatures. Journal of Environmental Engineering 131 (7), 1046-1051.

Horber, C., Christiansen, N., Arvin, E., Ahring, B. K., 1998. Improved dechlorinating performance of upflow anaerobic sludge blanket reactors by incorporation of *Dehalospirillum mutiviorans* into granular sludge. Applied and Environmental Microbiology 64 (5), 1860-1863.

Huang, L., Chen, Y., Zhou, H., Luo, S., Lan, C., Qu, L., 2003. Characterization of methanogenic Archaea in the leachate of a closed municipal solid waste landfill. FEMS Microbiology Ecology 46, 171-177.

Leclerc, M., Delgenes, J., Codon, J., 2004. Diversity of the archaeal community in 44 anaerobic digesters as determined by single strand conformation polymorphism analysis and 16S rDNA sequencing. Environmental Microbiology 6 (8), 809-819.

Lynch, N., Daniels, L., Parkin, G. F., 1987. Bioaugmentation of stressed anaerobic filters with methanogenic enrichment cultures. In: Proceedings of the 42nd Industrial Waste Conference. Purdue University, West Lafayette, Ind., pp. 285-296.

Macario, A. J. L., de Macano, E. C., 1988. Quantitative immunologic analysis of the methanogenic flora of digestors reveals a considerable diversity. Applied and Environmental Microbiology 54 (1), 79-86.

McCarty, P. L., Smith, D. P., 1986. Anaerobic wastewater treatment. Environmental Science and Technology 20 (12), 1200-1206.

McHugh, S., Carton, M., Mahony, T, O'Flaherty, V, 2003. Methanogenic population structure in a variety of anaerobic bioreactors. FEMS Microbiology Letters 219, 297-304.

Mladenovska, Z., lshoy, T., Mandiralioglu, A., Westernann, P., Ahring, B., 2001. Bioaugmentation of a mesophilic biogas reactor by anaerobic xylanolytic- and cellulolytic bacteria. In: Proceedings of the Ninth World Congress on Anaerobic Digestion, Antwepen, Belgium, pp. 183-188.

Nielsen, H. B., Mladenovska, Z., Ahring, B. K., 2007. Bioaugmentation of a two-stage thermophilic (68° C./55° C.) anaerobic digestion concept for improvement of the methane yield from cattle manure. Biotechnology and Bioengineering 97 (6), 1638-1643.

O'Flaherty, V., Colleran, E., 1999. Effect of sulphate addition on volatile fatty acid and ethanol degradation in an anaerobic hybrid reactor. I: process disturbance and remediation. Bioresource Technology 68, 101-107.

O'Flaherty, V., Colohan, S., Mulkerrins, D., Colleran, E., 1999. Effect of sulphate addition on volatile fatty acid and ethanol degradation in an anaerobic hybrid reactor. II: microbial interactions and toxic effects. Bioresource Technology 68, 109-120.

Rambaut, A., 2008. FigTree: Tree Figure Drawing Tool. Version 1.1.2. Institute of Evolutionary Biology. University of Edinburgh.

Raskin, 1., Zheng, D., Griffin, M. E., Stroot, P. G., Misra, P., 1995. Characterization of microbial communities in anaerobic bioreactors using molecular probes. Antonie Van Leeuwenhoek 68, 297-308.

Rittmann, B. E., Whiteman, R., 1994. Bioaugmentation: a coming of age. Water Quality International 1, 12-16.

Sambrook, J., Russell, D. W., 2001. Molecular Cloning: A Laboratory Manual, third. Cold Spring Harbor Laboratory Press, Cold Springs, N.Y.

Saravanane, R., Murthy, D. V. S., Krishnaiah, K., 2001a. Bioaugmentation and anaerobic treatment of pharmaceutical effluent in fluidized bed reactor. Journal of Environmental Science and Health 36 (5), 779-791.

Saravanane, R., Murthy, D V. S., Krishnaiah, K., 2001b. Bioaugmentation and treatment of cephalexin drug-based pharmaceutical effluent in an upflow anaerobic fluidized bed system. Bioresource Technology 76, 279-281.

Satoh, H., Okabe, S., Yamaguchi, Y., Watanabe, Y., 2003. Evaluation of the impact of bioaugmentation and biostimulation by in situ hybridization and microelectrode. Water Research 37, 2206-2216.

Schloss, P. O., Handelsman, J., 2005. introducing DOTUR, a computer program for defining operational taxonomic units and estimating species richness. Applied and Environmental Microbiology 71 (3), 1501-1506.

Sekiguchi, Y., Kamagata, Y., Syutsubo, K., Ohashi, A., Harada, H., Nakamura, K., 1998. Phylogenetic diversity of mesophilic and thermophilic granular sludges determined by 16S rRNA gene analysis. Microbiology 144, 2655-2665.

Singer, A. C., van der Cast, C. }., Thompson, J. P., 2005. Perspectives and vision for strain selection in bioaugmentation. Trends in Biotechnology 23 (2), 74-77.

Stephenson, D., Stephenson, T., 1992. Bioaugmentation for enhancing biological wastewater treatment. Biotechnology Advances 10, 549-559.

Tartakovsky, 8., Levesque, M.-J., Dumortier, R., Beaudet, R, Guiot, S. R, 1999. Biodegradation of pentachlorophenol in a continuous anaerobic reactor augmented with *Desulfitobacterium frappieri* PCP-1. Applied and Environmental Microbiology 65 (10), 4357-4362.

Tawfiki Hajji, K., Lepine, F., Bisaillon, Beaudet, R, Hawari, J, Guiot, S. R, 2000. Effects of bioaugmentation strategies in VASB reactors with a methanogenic consortium for removal of phenolic compounds. Biotechnology and Bioengineering 67 (4), 417-423.

Tawfiki Hajji, K., Lepine, F., Bisaillon, j. G., Beaudet, R., 1999. Simultaneous removal of phenol, ortho- and para-cresol by mixed anaerobic consortia. Canadian Journal of Microbiology 45 (4), 318-325

Tepe, N., Yurtsever, D., Mehta, R. J., Bruno, c., Punzi, V. L., Duran, M 2008. Odor control during post-digestion processing of biosolids through bioaugmentation of anaerobic digestion. Water Science and Technology 57 (4), 589-594.

Van Limbergen, H., Top, E. M., Verstraete, W., 1998. Bioaugmentation in activated sludge: current features and future perspectives. Applied Microbiology and Biotechnology 50, 16-23.

Wittebolle, L., Marzorati, M., Clement, 1., BaUoi, A., Daffonchio, D., Heylen, K., De Vos, P., Verstraete, W., Boon, N., 2009. Initial community evenness favours functionality under selective stress. Nature 458, 623-626.

Example 2

Reference is made to Tale et al., "Bioaugmentation for Anaerobic Digester Recovery After Organic Overload," Water Environment Federation Technical Exposition and Conference (WEFTEC 2010), New Orleans, La., 14 pp), the content of which is incorporated herein by reference in its entirety.

Abstract

Anaerobic digester upset due to organic overload sometimes occurs and methods to reduce recovery time would be beneficial. One potential method is bioaugmentation, the addition of an external culture for performance improvement. A culture with an initial specific methanogenic activity (SMA) value of 10.65±0.36 mL $CH_4$/gVSS-hr was enriched by feeding 0.17 g propionate/L-day under various microaerobic conditions. Enriching a culture for 25 mg $O_2$/L day increased its SMA by 29.7% in comparison to an anaerobic control, but higher oxygen doses yielded lower SMA values. Bioaugmenting organically overloaded digesters with this enrichment culture reduced the time required for digester effluent to decrease below 1000 mg SCOD/L by 114 days (11.4 solids retention time [SRTs]) and the time required to reach 25 mL $CH_4$/day by 37 days (3.7 SRTs). Bioaugmented digesters consistently produced lower effluent SCOD and more methane than non-bioaugmented digesters. Bioaugmentation is a promising approach for speeding up recovery of organically overloaded digesters.

Introduction

During anaerobic digestion, complex substrates are first fermented to organic acids, including propionic acid. The acids are then converted to acetic acid and $H_2$. Finally, the methanogens convert acetic acid as well as $H_2$ and $CO_2$ to $CH_4$. Under standard conditions, the bioconversion of propionic acid to acetic acid and $H_2$ is energetically unfavorable; however, $H_2$-consuming reactions, such as the conversion of $H_2$ and $CO_2$ to $CH_4$, drive the bioconversion of propionic acid in the forward direction. For this reason, degradation of propionic acid stops when the $H_2$ concentration is above $10^{-4}$ atm (McCarty and Smith, 1986). Higher $H_2$ concentrations can result in increased concentrations of propionic acid and other carboxylic acids in the digester (McCarty and Smith, 1986). The increased acid concentration can cause the pH to decrease and inhibit or stop $CH_4$ production.

Propionic acid accumulation is an indicator of anaerobic digester organic overload or process imbalance and propionate-utilizing microbial consortia play an important role when anaerobic digesters are subjected to organic overload. Smith and McCarty (1990) studied the effect of substrate overloading in a continuous-stirred tank reactor (CSTR) fed propionate (i.e., propionic acid) and ethanol. When the reactor was overloaded with an increased pulse dose of ethanol, the effluent propionate concentration remained high for over 18 days (3.7 HRTs), whereas the ethanol concentration decreased to a low value after 4 days. Therefore, propionate concentrations can remain chronically elevated for a significant time after a process overload. Strategies to reduce propionate and SCOD concentrations in organically overloaded digesters would be helpful to consistently meet effluent SCOD requirements of full-scale applications.

One possible strategy to reduce propionate and SCOD concentrations is bioaugmentation, defined as the addition of specialized microorganisms to biological systems to improve process performance. Bioaugmentation has typically been considered to remediate hazardous waste sites and improve aerobic bioprocesses, such as nitrification (Rittmann and Whitemann, 1994). It has also been studied in anaerobic systems to degrade specific organics (Tawfiki et al., 2000; Guiot et al., 2002; Lenz et al., 2009) lipid-rich wastes, cellulose, and cellulosic material present in manure (Nielsen et al., 2007) and to reduce the recovery time of digesters exposed to toxicants (Schauer-Gimenez et al., 2010).

Oxygen toxicity tolerance of anaerobic cultures used for bioaugmentation is of interest due to difficulties involved in handling large volumes of anaerobic cultures. Contact with oxygen is almost inevitable if cultures have to be transported from one location to another. In the past, researchers have studied the effect of oxygen addition on methanogenic cultures. Zitomer and Shrout (1998) operated bench scale methanogenic CSTR digesters at volumetric $O_2$ loadings of 1 and 0.1 g $O_2$/L-day; conventional anaerobic and aerobic reactors were also operated in parallel.

Methane was detected in the headspace gas of all the CSTR digesters operated under $O_2$-limited conditions. Furthermore, the reactor fed with 1 g $O_2$/L-day showed a residual COD concentration of 1400 mg/L, whereas the aerobic CSTR showed a much higher residual COD concentration of 2400 mg/L. Also it was observed that reactor pH after a pH drop caused by a shock overload of COD returned to >7 in the 1 g $O_2$/L-day and 0.1 g $O_2$/L-day reactors after 34 and 28 days, respectively, whereas the strictly anaerobic reactor showed no pH recovery even after 52 days; this highlighted benefits of adding limited $O_2$ to methanogenic digesters.

The study presented herein was undertaken to evaluate the effectiveness of bioaugmenting organically overloaded digesters with cultures enriched to degrade propionate in the presence of various $O_2$ doses. The goal was to reduce the recovery time of organically overloaded digesters.

Methods

SMA Tests of Anaerobic Cultures Against Calcium Propionate. Maximum propionate utilization rates can be determined by conducting specific methanogenic activity (SMA) testing (Sorensen and Ahring, 1993; Speece, 2008; Zitomer et al., 2008). SMA of the biomass sample was analyzed using propionate as the substrate by a standard protocol (Sorensen and Ahring, 1993).

The assays were conducted in 160-mL glass serum bottles. All test and control assays were run in triplicate. Test and control assays were supplied with 25 mL of diluted biomass samples having less than 2 g volatile suspended solids (VSS)/L. Basal nutrient medium (see below) was used to dilute biomass. All test assays received 3 g/L of propionate in the form of calcium propionate, whereas control assays contained no exogenous substrate. This substrate concentration is typically employed for propionate utilization testing (Speece, 2008; Zitomer et al., 2008), is not toxic to anaerobic biomass and is significantly higher than the Monod half saturation constant values. Therefore, the systems were not substrate-limited during the initial testing period. Biogas generated by control assays accounted for endogenous methane production during the testing period. Headspace for all test and control assays was flushed by a $N_2$:$CO_2$ gas mixture (mixed in 7:3 ratio v/v) to ensure anaerobic conditions. Further, all assays were incubated at 35±2° C. and were continuously shaken at 150 rpm using a gyratory shaker incubator. Gas production from each assay was monitored using a syringe displacement method over a period of 30 days. Graphs of cumulative gas production versus time were plotted. At the end of the testing period, methane content of the biogas was measured by gas chromatography (Series 600, GLOW-MAC Instrument Co., Bethlehem, Mass.) using a thermal conductivity detector and a packed column (CTR I, Agilent Associates, Inc., Deerfield, Ill.). Helium was used as the carrier gas at a flow of 30±2 mL/min with the temperature of the injector and detector set at 120° C. and the temperature of the oven set at 38° C. VSS concentration of the diluted biomass was measured before and after the test using standard methods (APHA, 1998) and the average of initial and final VSS concentrations was used to calculate SMA. Cumulative methane production was calculated by subtracting the average methane produced by the control assays. The portion of the curve representing cumulative methane versus time that had the steepest slope was used to calculate SMA using linear regression. The activity (i.e., SMA) of each test assay was expressed as mL $CH_4$/hr-gVSS. Finally, the average and standard deviation of the SMA values were calculated.

Enrichment of Culture.

A biomass sample from an upflow anaerobic sludge blanket reactor treating brewery wastewater was obtained and had an initial propionate SMA value of 10.65±0.36 mL $CH_4$/gVSS-hr. This biomass was then enriched for propionate utilization under anaerobic and micro-aerobic conditions. Enrichments were accomplished in 750-mL serum bottles containing 150 mL of active volume and operated in semi-continuous CSTR mode. The serum bottles were initially sparged with a $N_2$:$CO_2$ gas mixture (mixed in 7:3 ratio v/v), then fed 0.17 g propionate/L-day (0.25 g COD/L-day) with basal nutrient medium (see below), and shaken continuously at 150 rpm and 35±2° C. at a 15-day SRT. Additionally, $O_2$ equivalent to 0%, 10%, 50% and 90% of the COD exerted by the daily propionate dose was supplied to the different serum bottles in the form of atmospheric air. The equivalent doses of air were 0, 14, 68 and 124 mL air @350 C/L-day. The resulting volumetric $O_2$ loading rates were 0, 0.025, 0.125 and 0.225 g $O_2$/L-day. SMA values of the enrichment cultures were measured after 580 days (36.6 SRT) of enrichment. The enrichment culture demonstrating the highest SMA value was subsequently used for bioaugmentation.

Bioaugmented Digesters.

The effectiveness of bioaugmentation was evaluated by organically overloading small-scale, non-fat-dry-milk-fed anaerobic digesters; one digester set was bioaugmented, whereas another set was not. In addition, some digesters were neither overloaded, nor bioaugmented. Each digester was a 160-mL serum bottle incubated at 35±2° C. containing 50 mL of active volume and seeded with biomass from a laboratory-scale digester fed non-fat dry milk. Digesters were initially sparged with a $N_2$:$CO_2$ gas mixture (mixed in 7:3 ratio v/v) and then operated at a 10-day SRT by daily wasting and feeding. Digesters received basal nutrient medium and non-fat dry milk (2.7 g COD/L-day). A shock overload of non-fat dry milk (32 g COD/L digester volume) was given for one day to all the digesters except the non-overloaded set. Following the organic overload, bioaugmented digesters were provided with 1.7 mL/day (70 mg VSS/L-day) of the enrichment culture, whereas non-bioaugmented digesters received 1.7 mL/day of an autoclaved, abiotic version of the enrichment culture substituted for 1.7 mL of basal medium.

Basal Nutrient Medium.

The basal nutrient medium contained the following [mg/L]: $NH_4Cl$ [400]; $MgSO_4 \cdot 6H_2O$ [250]; $KCl$ [400]; $CaCl_2 \cdot 2H_2O$ [120]; $(NH_4)_2HPO_4$ [80]; $FeCl_3 \cdot 6H_2O$ [55]; $CoCl_2 \cdot 6H_2O$ [10]; $KI$ [10]; the trace metal salts $MnCl_2 \cdot 4H_2O$, $NH_4VO_3$, $CuCl_2 \cdot 2H_2O$, $Zn(C_2H_3O_2)_2 \cdot 2H_2O$, $AlCl_3 \cdot 6H_2O$, $NaMoO_4 \cdot 2H_2O$, $H_3BO_3$, $NiCl_2 \cdot 6H_2O$, $NaWO_4 \cdot 2H_2O$, and $Na_2SeO_3$) [each at 0.5]; $NaHCO_3$ [5000]; and resazurin [1].

Analytical Methods. Soluble COD (SCOD) was measured by filtering the sample through a 0.45-μm filter and measuring the filtrate COD concentration using standard methods (APHA et al., 1998). The pH was measured using a bench-top pH meter and a general-purpose pH electrode. The volume of biogas produced was measured using a water-lubricated glass syringe via the plunger displacement method. Biogas $CH_4$ content concentrations were determined by gas chromatography. The VSS concentration was measured using standard methods (APHA et. al., 1998).

Results

Effect of Oxygen on Activity of an Enrichment Culture.

Figure 7:
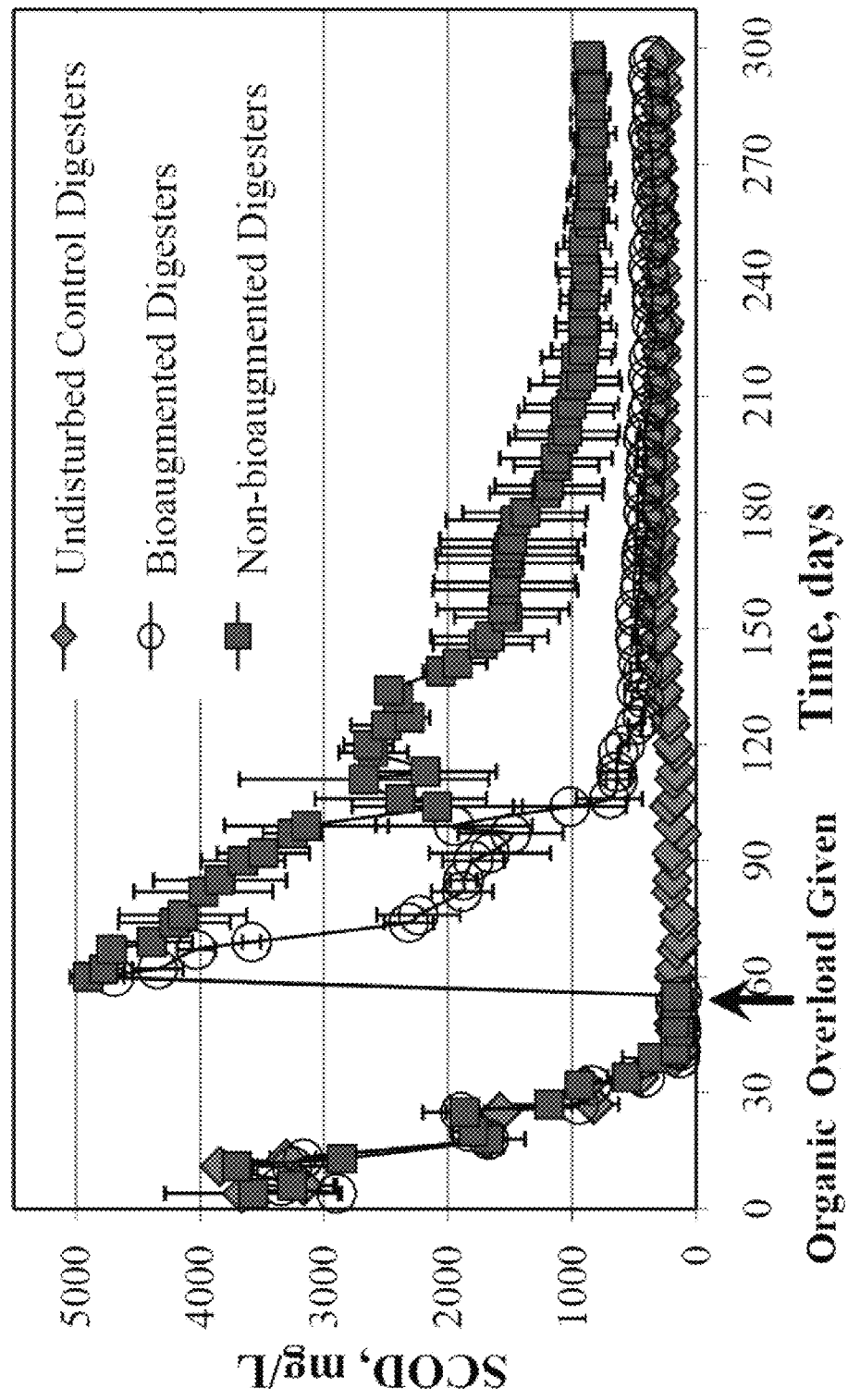
FIG. 7 illustrates the effluent SCOD of digesters. Error bars represent standard deviations among three (3) replicates.

As shown in FIG. 7, surprisingly, there was no increase in SMA after 580 days (38.6 SRTs) of enrichment for the 0 mg $O_2$/L-day dose, but addition of 25 mg $O_2$/L-day resulted in an increase in the average SMA by 29.7%; however, this increase in the activity was found to be statistically insignificant (p=0.23). The statistical insignificance may have been due to the low number (i.e., 3) of replicates used. Further increase in the oxygen dose had a negative effect on SMA. Addition of 225 mg $O_2$/L-day resulted in a decrease in the SMA by 90.3%; this decrease was found to be statistically significant (p=0.03).

Addition of 25 mg $O_2$/L-day to the enrichment culture may have increased its oxygen-tolerating capacity so that, when it was being transferred from the enrichment reactor to SMA assay bottles, it may have suffered minimal oxygen toxicity due to exposure to atmospheric air and, therefore retained its activity. The culture fed with no oxygen may have less capability to withstand any toxic effects due to air exposure. Excess doses of oxygen (>25 mg $O_2$/L-day) may have decreased SMA of the enrichment culture since higher doses of oxygen may have been toxic to anaerobic microorganisms.

Bioaugmentation Experiment. Since the enrichment culture fed with 25 mg $O_2$/L-day showed the highest activity, it was used for the subsequent bioaugmentation experiment.

The purpose of the bioaugmentation investigation was to determine if faster recovery occurred with addition of a bioaugmentation culture after a digester was subjected to a shock organic overload.

Effluent SCOD

Figure 8:
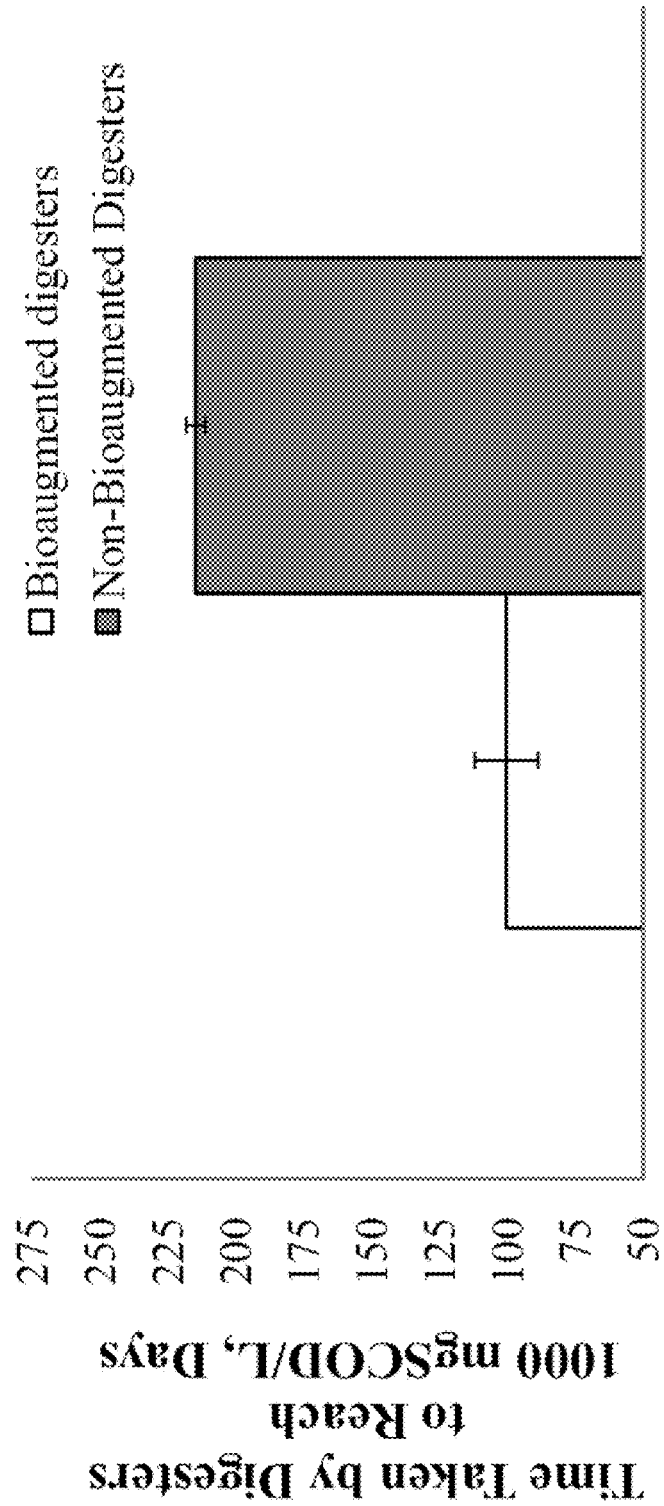
FIG. 8 illustrates the time required by bioaugmented and non-bioaugmented digesters to attain 1000 mg/L effluent SCOD concentration following the organic overload. Error bars represent standard deviations among three (3) replicates.

As shown in FIG. 8, all the digesters initially required about 40 days (4 SRT's) to attain an average quasi steady-state effluent SCOD concentration of 290±150 mg/L before the shock organic overload. The shock organic overload was administrated on day 57 as explained in the Methods section and shown in FIG. 8. The organic overload resulted in higher effluent SCOD concentrations for all the bioaugmented and non-bioaugmented digesters and the resulting effluent SCOD increased to 5000±750 mg/L (see FIG. 8). Following the organic overload, the effluent SCOD started to decrease due to dilution, biological reactions and bioaugmentation. After about 6 SRTs following the overload event, the effect of bioaugmentation started to become visible in terms of lower effluent SCOD concentration for the bioaugmented digesters as compared to non-bioaugmented digesters.

Before the organic overload, the average quasi-steady state pH of all the digesters was 6.9±0.2. After the organic overload, the average pH of the overloaded digesters dropped to 6.5±0.2. Moreover, the average pH of the overloaded digesters after 6 SRTs following the organic overload was found to be 7.1±0.3.

Figure 9:
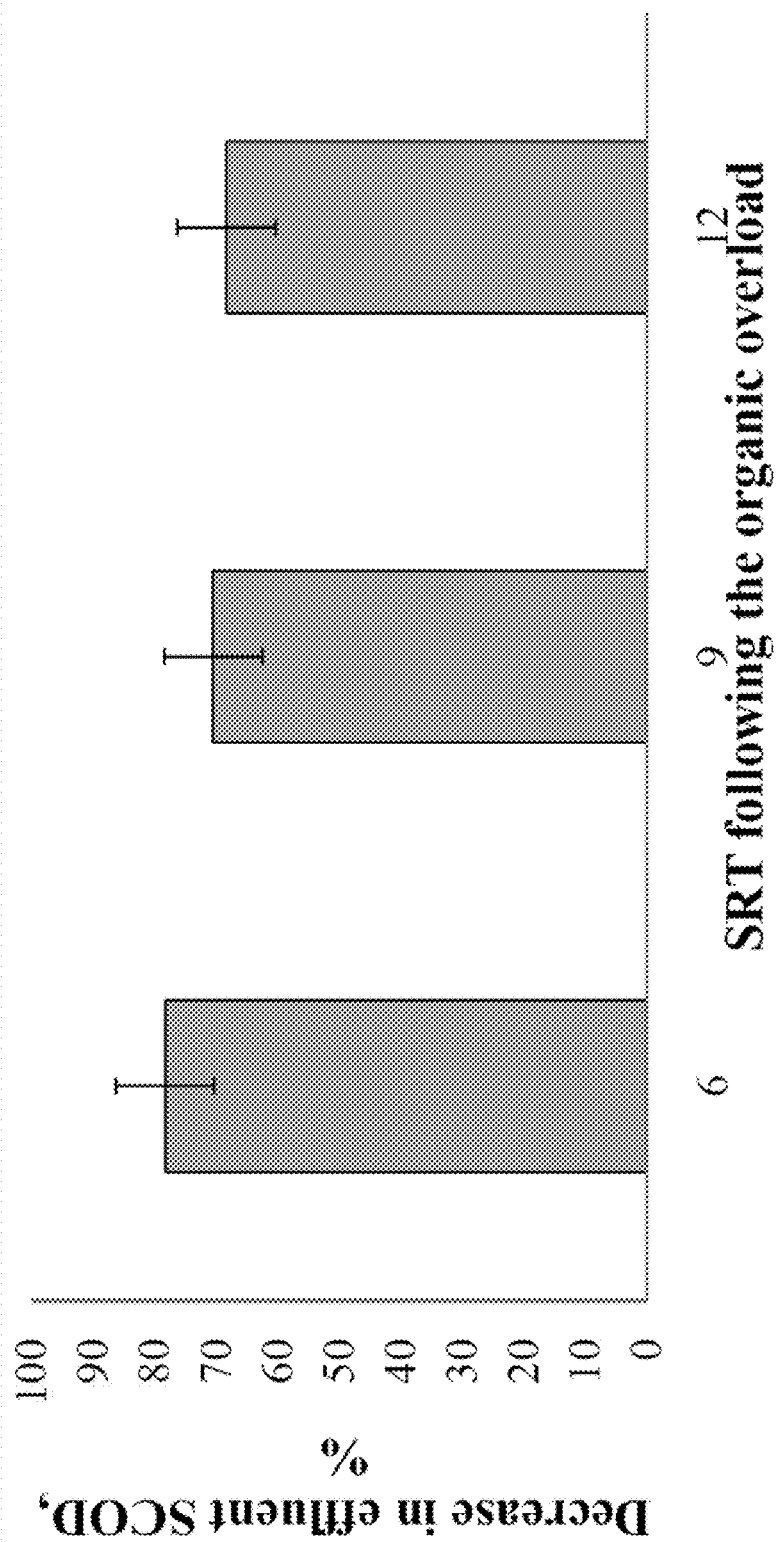
FIG. 9 illustrates the percent SCOD decrease of bioaugmented digesters. Error bars represent standard deviations among three (3) replicates.

The time required after organic overload for the effluent SCOD concentration to decrease below 1000 mg/L was used as a measure of recovery time. FIG. 9 shows the time required by bioaugmented and non-bioaugmented digesters to attain a 1000 mg/L effluent SCOD concentration.

Figure 10:
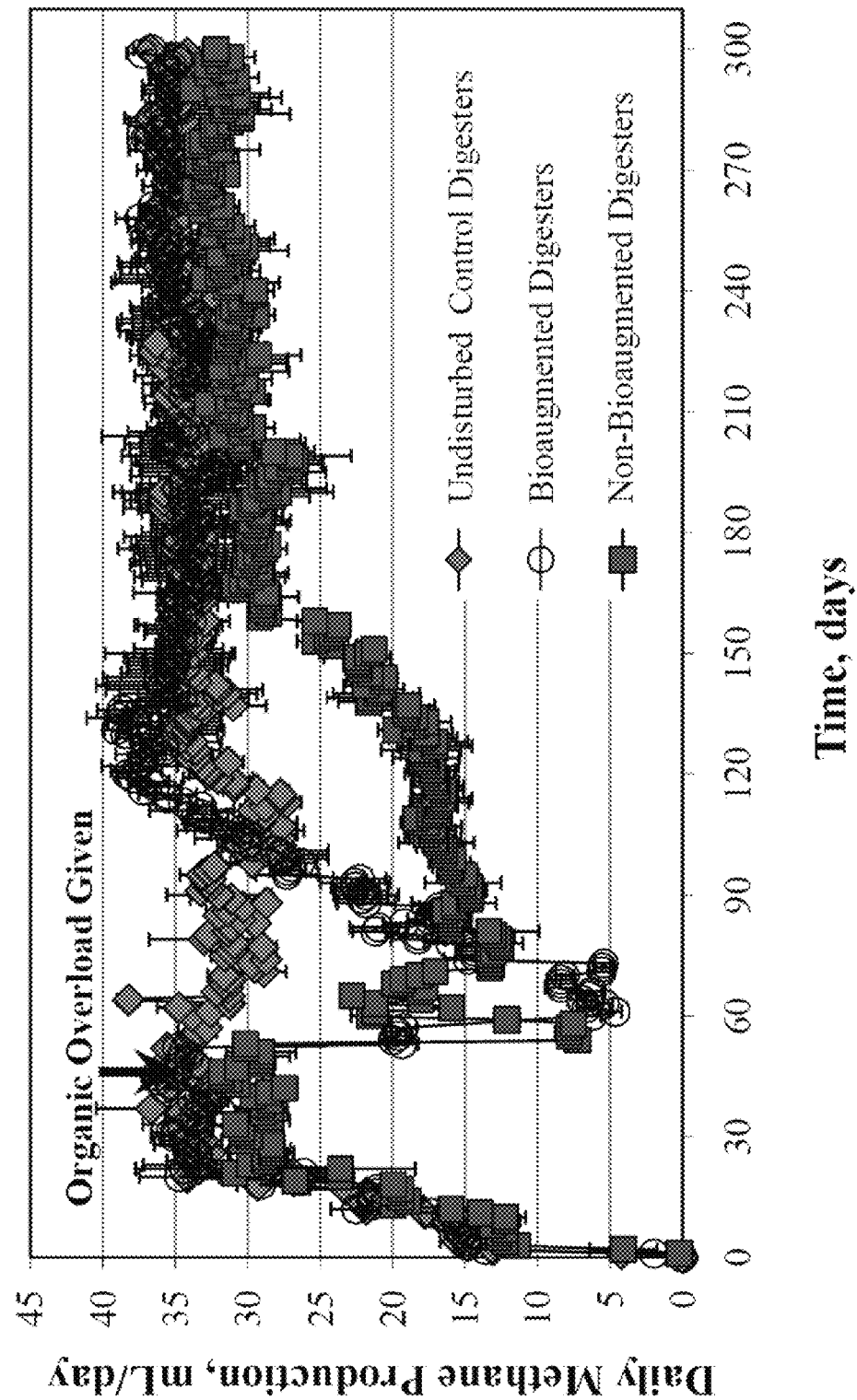
FIG. 10 illustrates the daily methane production from digesters. Error bars represent standard deviations among three (3) replicates.

The bioaugmented digesters took 114 days less to attain 1000 mg SCOD/L as compared to non-bioaugmented digesters (p<0.03). It is interesting to note that the bioaugmented digesters consistently produced lower average effluent SCOD as compared to their respective non-bioaugmented digesters, even after 6 SRTs following the shock overload. To demonstrate the same, the percent difference between the SCOD concentrations of the bioaugmented and the non-bioaugmented digesters after 6, 9 and 12 SRTs following the organic overload were evaluated (see FIG. 10). During the recovery period, bioaugmented digesters consistently demonstrated lowed effluent SCOD values. The beneficial effect of bioaugmentation was observed for a prolonged period following the shock overload. This is in contrast to the findings of other researchers (Lynch et al., 1987) who found that bioaugmenting with cultures enriched for propionate and butyrate following an organic overload did not speed up recovery of anaerobic filters for prolonged periods. The reason behind successful and prolonged recovery of shock-overloaded digesters may be because, in the current study, the bioaugmentation cultures were supplied on a daily basis, whereas the previous researchers (Lynch et al., 1987) supplied bioaugmentation culture only once leading to washout from the bioaugmented anaerobic filter.

Figure 11:
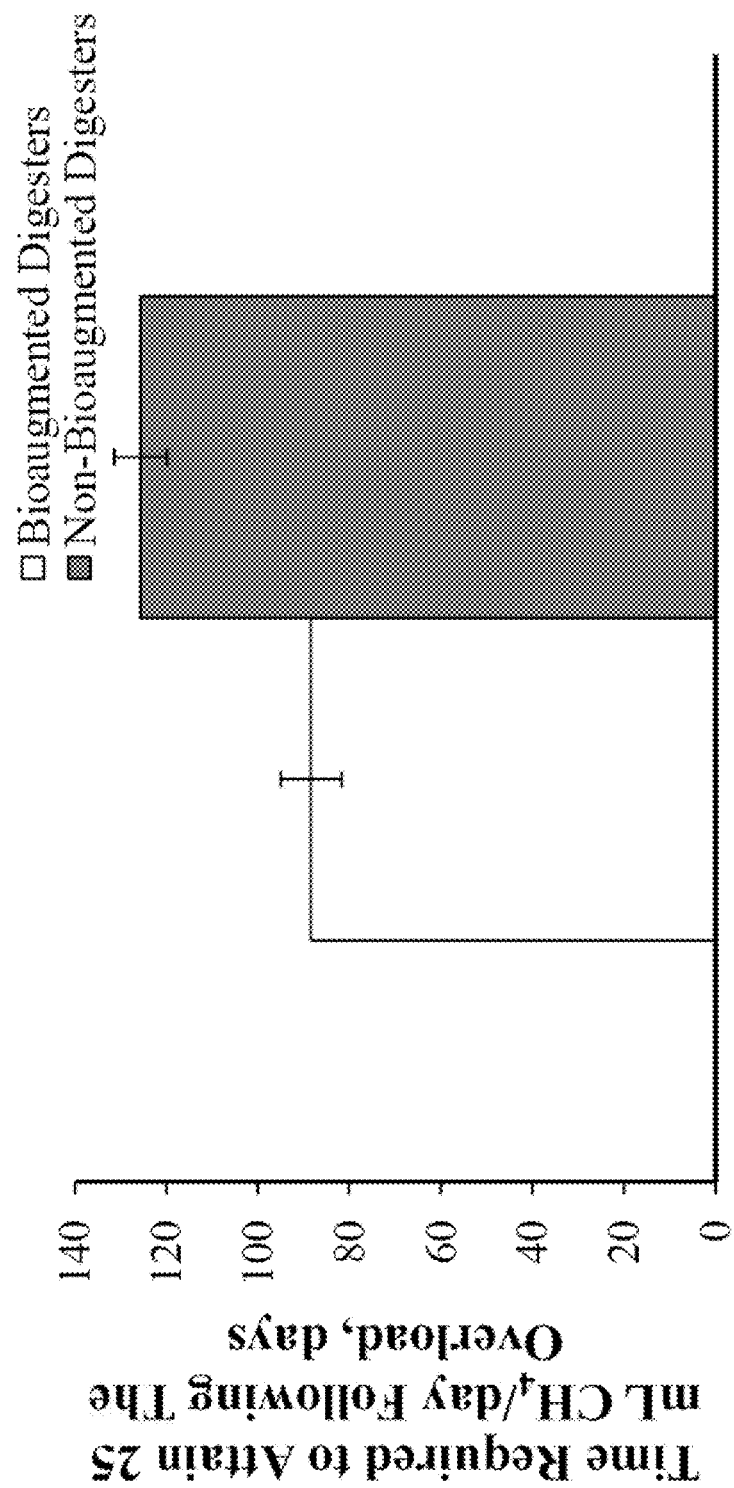
FIG. 11 illustrates the time required by bioaugmented and non-bioaugmented digesters to attain 25 mL $CH_4$/day following the organic overload. Error bars represent standard deviations among three (3) replicates.
Figure 12:
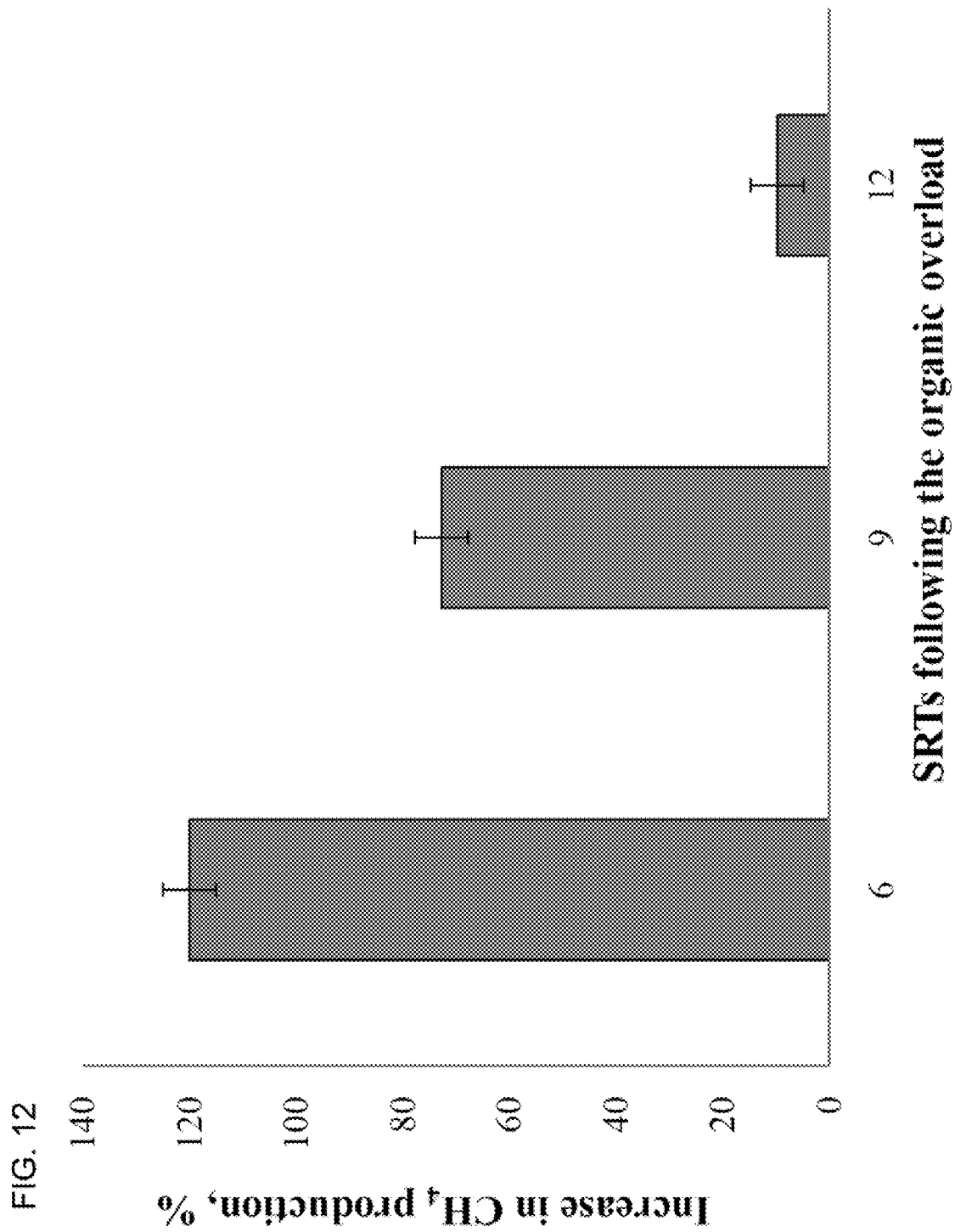
FIG. 12 illustrates the percent methane increase from bioaugmented digesters. Error bars represent standard deviations among three (3) replicates.

FIG. 11 shows the methane production from bioaugmentation digesters. Like effluent SCOD concentration, all the digesters required an initial period of about 40 days (4 SRTs) to reach an average quasi-steady-state of 32±4 mL $CH_4$/day methane production. During this period, average methane content in the biogas produced by all the digesters was 59±4% (v/v). The organic overload was given on day 57 and, following the organic overload, methane production from the digesters decreased to below 10 mL $CH_4$/day and the average methane content in biogas produced by all the digesters was 16±11% (v/v). The daily methane production started to recover and after about 180 days of operation (i.e. 12 SRTs after the organic overload). The times required to attain 25 mL $CH_4$/day (i.e., 78% of the pre-organic-overload value) following the organic overload were compared. FIG. 12 shows the time required by bioaugmented and non-bioaugmented digesters to attain 25 mL $CH_4$/day methane production following the organic overload.

The bioaugmented digesters required less time than the respective non-bioaugmented digesters to reach 25 mL $CH_4$/day (37 days less) (p<0.01). To evaluate the consistency of bioaugmentation on methane production during the recovery period, the percent increase in methane production after 6, 9 and 12 STRs following the organic overload was evaluated. FIG. 12 shows the percent increase in methane production after 6, 9 and 12 SRTs, which was calculated as the percent difference between daily methane production from bioaugmented and non-bioaugmented digesters.

Conclusions

Enrichment of an anaerobic culture for propionate degradation did not result in an increase in SMA even after 580 days of enrichment (38.6 SRTs) for a 0 mg $O_2$/L-day oxygen dose, whereas addition of 25 mg $O_2$/L-day oxygen (equivalent to 10% of the daily COD supplied) resulted in increased average SMA by 29.7%. Additional increases in oxygen dose resulted in lower SMA values.

Shock organic overloaded digesters were bioaugmented with a culture enriched to degrade propionate under microaerobic conditions. Digesters bioaugmented with cultures enriched for propionate and a small amount of oxygen resulted in lower effluent SCOD than non-bioaugmented digesters. The difference between effluent SCOD of the bioaugmented and non-bioaugmented digesters was apparent even after 12 SRTs following the shock overload. Bioaugmented digesters consistently showed lower effluent in SCOD and took 114 days less to reach 1000 mg SCOD/L effluent concentration. Higher SCOD reduction from the bioaugmented digesters may have been due to the high SMA value of the bioaugmentation culture used which may have led to more rapid metabolism of propionic acid. In conclusion, the recovery time of some anaerobic digesters subjected to organic overload can be reduced by bioaugmentation with cultures enriched to degrade propionate, and the beneficial influence of bioaugmentation can be apparent for a long period after process upset.

References for Example 2

American Public Health Association (APHA), American Water Works Association (AWWA), Water Environment Federation (WEF) (1998) *Standard Methods for the Examination of Water and Wastewater* (20th ed.). APHA et al.

Guiot, S. R., Tartakovsky, B., Lanthier, M., Levesque, M. J., Manuel, M. F., Beaudet, R., Greer, C. W., and Villemur, R. (2002) "Strategies for Augmenting the Pentachlorophenol Degradation Potential of UASB Anaerobic Granules." *Water Science and Technology*. 45.10: 35-41.

Lenz, M., Enright, A. M. O'Flaherty, V., van Aest, A. C., and Lens P. N. L. (2009) "Bioaugmentation of UASB Reactors with Immobilized *Sulfurospirillum barnesii* for Simultaneous Selenate and Nitrate Removal." *Applied Microbiology and Biotechnology*, 83.2: 377-388.

Lynch, N., Daniels L., and Parkin, G. F. (1987) "Bioaugmentation of Stressed Anaerobic Filters with Methanogenic Enrichment Cultures." *Proceedings of the 42nd Industrial Waste Conference.* (pp. 285-296). West Lafayette, Ind.: Purdue University.

McCarty, P. L. and Smith, D. P. (1986) "Anaerobic Wastewater Treatment." *Environmental Science and Technology.* 20.12: 1200-1206.

Nielsen, H. B., Mladenovska, Z., and Ahring, B. K. (2007) "Bioaugmentation of a Two-Stage Thermophilic (68° C./55° C.) Anaerobic Digestion Concept for Improvement of the Methane Yield from Cattle Manure." *Biotechnology and Bioengineering.* 97.6: 1638-1643.

Rittmann, B. E. and Whiteman, R. (1994) "Bioaugmentation: A Coming of Age." *Water Quality International.* 1: 12-16.

Schauer-Gimenez, A. E., Zitomer, D. H., Maki, J. S, and Struble, C. A. (2010) "Bioaugmentation for Improved Recovery of Anaerobic Digesters after Toxicant Exposure". *Water Research,* 44.12:3555-3564.

Sorensen, A. H. and Ahring, B. K. (1993) "Measurement of the Specific Methanogenic Activity of Anaerobic Digestor Biomass." *Applied Microbiology and Biotechnology,* 40: 427-431.

Smith, D. P., and McCarty, P. L. (1990) "Factors Governing Methane Fluctuations Following Shock Loading of Digesters." *Research Journal of the Water Pollution Control Federation.* 62.1: 58-64.

Speece, R. (2008) *Anaerobic Biotechnology and Odor/Corrosion Control for Municipalities and Industries.* Archae Press. Nashville, Tenn.

Tawfiki Hajji, K., Lepine, F., Bisaillon, J. G., Beaudet, R., Hawari, J., and Guiot, S. R. (2000) "Effects of Bioaugmentation Strategies in UASB Reactors with a Methanogenic Consortium for Removal of Phenolic Compounds." *Biotechnology and Bioengineering.* 67.4: 417-423.

Zitomer, D. H, Johnson, C. C. and Speece R. E. (2008) "Metal Stimulation and Municipal Digester Thermophilic/Mesophilic Activity." *Journal of Environmental Engineering.* 134.1:42-47.

Zitomer, D. H. and Shrout, J. D. (1998) "Feasibility and Benefits of Methanogenesis Under Oxygen-Limited Conditions." *Waste Management.* 18: 107-116.

Example 3

Reference is made to Tale et al., "Bioaugmentation Can Improve Anaerobic Digester Performance after Organic Overload," (2010) in proceedings of International Water Association (IWA) 12th. World Congress on Anaerobic Digestion, Guadalajara, Mexico, October 31st-November 4th, 5 pp; the content of which is incorporated herein by reference in its entirety.

Abstract

Acids can accumulate in anaerobic digesters after an organic overload and acid build-up can inhibit or stop $CH_4$ production. Therefore, methods to reduce acid concentrations would be helpful. One potential method to improve recovery involves bioaugmentation, addition of specific microorganisms to improve performance. In this study, we bioaugmented transiently overloaded digesters with a propionate-degrading enrichment culture in an effort to decrease recovery time. Biomass samples from 14 different, full-scale anaerobic digesters were screened for specific methanogenic activity (SMA) against propionate; the microbial communities were also compared. SMA values spanned two orders of magnitude. Principle component analysis of DGGE banding patterns for a functional gene (mcrA) suggested an underlying relationship between community structure and SMA; presence of hydrogenotrophic methanogens closely related to *Methanospirillum hungalei* and *Methanobacterium beijingense* increased SMA. The biomass sample demonstrating the highest SMA was enriched for propionate degradation and used to bioaugment overloaded digesters. Bioaugmented digesters recovered more rapidly following the organic overload, requiring approximately 25 days (2.5 SRTs) less to recover as compared to non-bioaugmented digesters. Benefits of bioaugmentation continued for more than 12 SRTs after organic overload. Bioaugmentation is a promising approach to decrease recovery time after organic overload and improve long-term reactor performance.

Introduction

Under standard conditions, the bioconversion of propionate to acetate and $H_2$ is energetically unfavorable; however, $H_2$-consuming reactions, such as the conversion of $H_2$ and $CO_2$ to $CH_4$, drive the bioconversion of propionate in the forward direction. For this reason, degradation of propionate stops when the $H_2$ concentration is above $10^{-4}$ atm (McCarty and Smith, 1986). Higher $H_2$ concentrations can result in increased propionic acid and other carboxylic acids in the digester (McCarty and Smith, 1936). The increased acid concentration can cause the pH to decrease and inhibits or stops $CH_4$ production.

Propionate accumulation is an indicator of anaerobic digester organic overload or process imbalance and propionate-utilizing microbial consortia play an important role when anaerobic digesters are subjected to organic overload. Smith and McCarty (1990) studied the effect of substrate overloading in a continuous-stirred tank reactor (CSTR) fed propionate and ethanol. When the reactor was overloaded with an increased pulse dose of ethanol, the effluent propionate concentration remained high for over 18 days (3.7 HRTs), whereas the ethanol concentration decreased to a low value after 4 days. Therefore, propionate concentrations can remain chronically elevated for a significant time after a process overload. Strategies to reduce propionate and SCOD concentrations in organically overloaded digesters would be helpful to consistently meet effluent SCOD requirements of full-scale applications.

One possible strategy to reduce propionate and SCOD concentrations is bioaugmentation, defined as the addition of specialized microorganisms to biological systems to improve process performance. Bioaugmentation has typically been considered to remediate hazardous waste sites and improve aerobic bioprocesses, such as nitrification (Rittmann and Whitemann, 1994). It has also been studied in anaerobic systems to degrade specific organics (Tawfiki et al., 2000; Guiot et al., 2002; Lenz et al., 2009) lipid-rich wastes, cellulose, and cellulosic material present in manure (Nielsen et al., 2007) and to reduce the recovery time of digesters exposed to toxicants (Schauer-Gimenez et al., 2010).

In this study, we screened biomass samples from various full-scale anaerobic reactors by measuring propionate utilization rates. The most rapid propionate-utilizing biomass was enriched and used to bioaugment organically overloaded digesters in an effort to decrease the recovery time, decrease effluent SCOD and increase methane production.

Methodology

SMA Tests of Anaerobic Cultures Against Calcium Propionate.

Specific methanogenic activity (SMA) values of biomass samples from full-scale anaerobic reactors were determined using propionate as the substrate by a standard protocol (Owen et al., 1979). All biomass samples were diluted to <2 g volatile suspended solids (VSS)/L using basal medium with calcium propionate (3.8 g/L). Granular biomass was disrupted before testing by crushing the granules by hand. Gas generation was monitored for 30 days and $CH_4$ concentration was measured as described below. The maximum $CH_4$ production rate was determined by linear regression using the initial points on a graph of cumulative $CH_4$ production volume versus time.

Methanogenic Community Analysis.

Methyl coenzyme-M reductase (MCR) is the terminal enzyme complex in the biological methane generation pathway and catalyzes the reduction of the methyl group bound to coenzyme-M, with the concomitant release of methane (Woese and Fox, 1977). This enzyme complex is thought to be unique to and ubiquitous in methanogens (Thauer, 1998), making it a suitable tool for the detection of methanogens. Further studies have highlighted the use of the mcrA gene as a target for the detection of methanogens in a wide range of environments including rice paddies (Lueders et al., 2001), peat bogs (Hales et al., 1996; Lloyd et al., 1998; Nercessian et al., 1999; Juottonen et al., 2006), termite gut (Ohkuma et al., 1995), anaerobic digesters (Rastogi et al., 2008), polluted water (Ufnar et al., 2007), hypereutrophic lakes (Earl et al., 2003), hydrothermal sediments (Dhillon et al., 2005), subsurfaces of tidal flats (Wilms et al., 2007) and marine environments (Bidle et al., 1999).

Methanogenic communities in biomass samples were characterized using primers that amplify the mcrA gene which codes for the MCR enzyme (Luton et al., 2002). DNA was extracted from the samples using the PowerSoil™ DNA Isolation Sample Kit (MoBio Laboratories, Inc., Carlsbad, Calif.). DNA was amplified by conducting PCR for GCmcrAlf (5'-GCclamp-GGTGGTGTMGGATTCACACAR-TAYGCWACAGC-3' (SEQ ID NO:11)) and mcrA500r (5'-TTCATTGCRTAGTTWGGRTAGTT-3' (SEQ ID NO:12)) primers (Luton et al., 2002). The PCR conditions were as follows: initial denaturation at 95° C. (5 min), 35 cycles of 95° C. (1 min), 58° C. (1 min), and 72° C. (3 min), and a final extension of 10 minutes at 72° C. The program included a slow ramp in temperature (0.1° C. s$^{-1}$) between the annealing and extension steps of the first 5 cycles of the protocol to assist in the initial formation of product due to the degenerate nature of the primers, as recommended (Luton et al., 2002).

The size of the expected PCR products was confirmed using a 1% (w/v, Tris-acetate-EDTA buffer, Sambrook and Russell, 2001) agarose gel and a λ (Hind III digest) φX174 (Hae III digest) DNA ladder stained with ethidium bromide (0.01%, v/v). Gels were visualized using a UVP Model M-20 UV transilluminator (UVP, Upland, Calif.).

The amplified products were separated using denaturing gradient gel electrophoresis (DGGE). For a general review of DGGE, refer to Muyzer et al. (1999). The DGGE technique has been extensively used in the field of microbial ecology to compare microbial communities and use of DGGE with mcrA as a target gene have been reported (Wilms et al., 2007; Galand et al., 2002). A polyacrylamide gel with a linear gradient (40 to 70% v/v denaturant concentration from top to bottom of gel) was used. Forty uL of the amplified DNA product (equivalent to approximately 75 ng of DNA) was added to each lane of the polyacrylamide gel. Amplified products separated on the gel were stained using SYBR® Green (Invitrogen, CA. USA) dye and the gel image was analyzed using Lab Works software (v. 4.6.00.0). Densitometric data obtained from the image were used to perform principle component analysis (PCA) using the MATLAB (v.7.6 (R2008a)) software package. Clustering on the PCA plot was performed using the farthest neighbor algorithm.

Three DGGE bands having most significant effect on clustering pattern were excised and cloned using the TOPO TA Cloning® Kit according to the manufacturer's instructions (Invitrogen, Carlsbad, Calif.). Transformants containing plasmids with amplified product were screened via blue/white selection (Sambrook and Russell, 2001). Twelve light-colored colonies were picked per DGGE band and a PCR, with PucF (5'-GGAATTGTG AGCGGATAACA-3' (SEQ ID NO:9)) and PueR (5'-GGCGATTAAGTTGGGTAACG-3' (SEQ ID NO:10)) primers was run on each colony to amplify the DNA. The PCR conditions for the PUC primers were as follows: denaturing temperature of 94° C. (1 min), annealing temperature of 55° C. (1 min), and elongation temperature of 72° C. (1 min), and a final extension of 10 minutes at 72° C. The size of the PUC-amplified PCR products were confirmed as described above. The amplified DNA was cleaned using the UltraClean™ PCR Clean-Up™ Kit (MoBio Laboratories, Carlsbad, Calif.) according to manufacturer's protocol. The amplified products were sequenced at the University of Chicago Cancer Research Center's DNA sequencing facility using a capillary automated DNA sequencer (Applied Biosystems 3730XL, Foster City, Calif.). Contiguous sequences were assembled for each clone using forward and reverse sequences. Vector segments from the contiguous sequences were removed using, a tailor-made computer program which utilized the UniVec database of the National Center for Biotechnology Information (NCBI) (http://www.ncbi.nlm.nih.gov/VecScreen/UniVec.html) using the Basic Local Alignment Search Tool (BLAST) (Altschul et al., 1997) for cloning vectors. Further, the clones were submitted for BLASTn (Altschul et al., 1997) query on NCBI database (http://www.ncbi.nlm.nih.gov) for identifying them.

Enrichment of Most Rapid Propionate-Utilizing Culture.

The biomass sample demonstrating the highest SMA value was enriched for propionate utilization. Enrichment was accomplished in a 750-mL serum bottle containing 150 mL of active volume and operated in batch CSTR mode. The serum bottle was initially sparged with a $N_2$:$CO_2$ gas mixture (mixed in 7:3 ratio v/v), then fed 0.17 g propionate/L-day (0.25 gCOD/L-day) with basal nutrient medium (see below), and shaken continuously at 150 rpm and 35±2° C. at a 15-day SRT. The SMA of the enrichment culture was measured at the start of enrichment and again after 580 days (38.6 HRTs).

Bioaugmented Digesters.

The effectiveness of bioaugmentation was evaluated by organically overloading small-scale, non-fat-dry-milk-fed anaerobic digesters; one digester set was bioaugmented, whereas another set was not. In addition, some digesters were neither overloaded, nor bioaugmented. Each digester was a 160-mL serum bottle incubated at 35±2° C. containing 50 mL of active volume and seeded with biomass from a laboratory-scale digester fed non-fat dry milk. Digesters were initially sparged with a $N_2$:$CO_2$ gas mixture (mixed in 7:3 ratio v/v) and then operated at a 10-day SRT by daily wasting and feeding. Digesters received basal nutrient medium and non-fit dry milk (2.7 g COD/L-day). A shock overload of non-fat dry milk (32 g COD/L digester volume) was given for one day to all the digesters except the non-overloaded set. Following the organic overload, bioaugmented digesters were provided with 1.7 mL/day (70 mg VSS/L-day) of the enrichment culture whereas non-bioaugmented digesters received 1.7 mL/day of an autoclaved, abiotic version of the enrichment culture substituted for 1.7 mL of basal medium.

Basal Nutrient Medium.

The basal nutrient medium contained the following [mg/L]: $NH_4Cl$ [400]; $MgSO_4 \cdot 6H_2O$ [250]; KCl [400]; $CaCl_2 \cdot 2H_2O$ [120]; $(NH_4)_2HPO_4$ [80]; $FeCl_3 \cdot 6H_2O$ [55]; $CoCl_2 \cdot 6H_2O$ [10]; KI [10]; the trace metal salts $MnCl_2 \cdot 4H_2O$, $NH_4VO_3$, $CuCl_2 \cdot 2H_2O$, $Zn(C_2H_3O_2)_2 \cdot 2H_2O$, $AlCl_3 \cdot 6H_2O$, $NaMoO_4 \cdot 2H_2O$, $H_3BO_3$, $NiCl_2 \cdot 6H_2O$, $NaWO_4 \cdot 2H_2O$, and $Na_2SeO_3$) [each at 0.5], $NaHCO_3$ [5000]; and resazurin [1].

Analytical Methods.

Soluble COD (SCOD) was measured by filtering the sample through a 0.45-μm filter and measuring the filtrate COD concentration using standard methods (APHA et al., 1998). The pH was measured using a bench-top pH meter and a general-purpose pH electrode. The volume of biogas produced was measured using a water-lubricated glass syringe via the plunger displacement method. Biogas $CH_4$ content concentrations were determined by gas chromatography. VSS concentration was measured using standard methods (APHA et al., 1998).

Results and Discussion

SMA of Biomass for Various Anaerobic Reactors.

Figure 13:
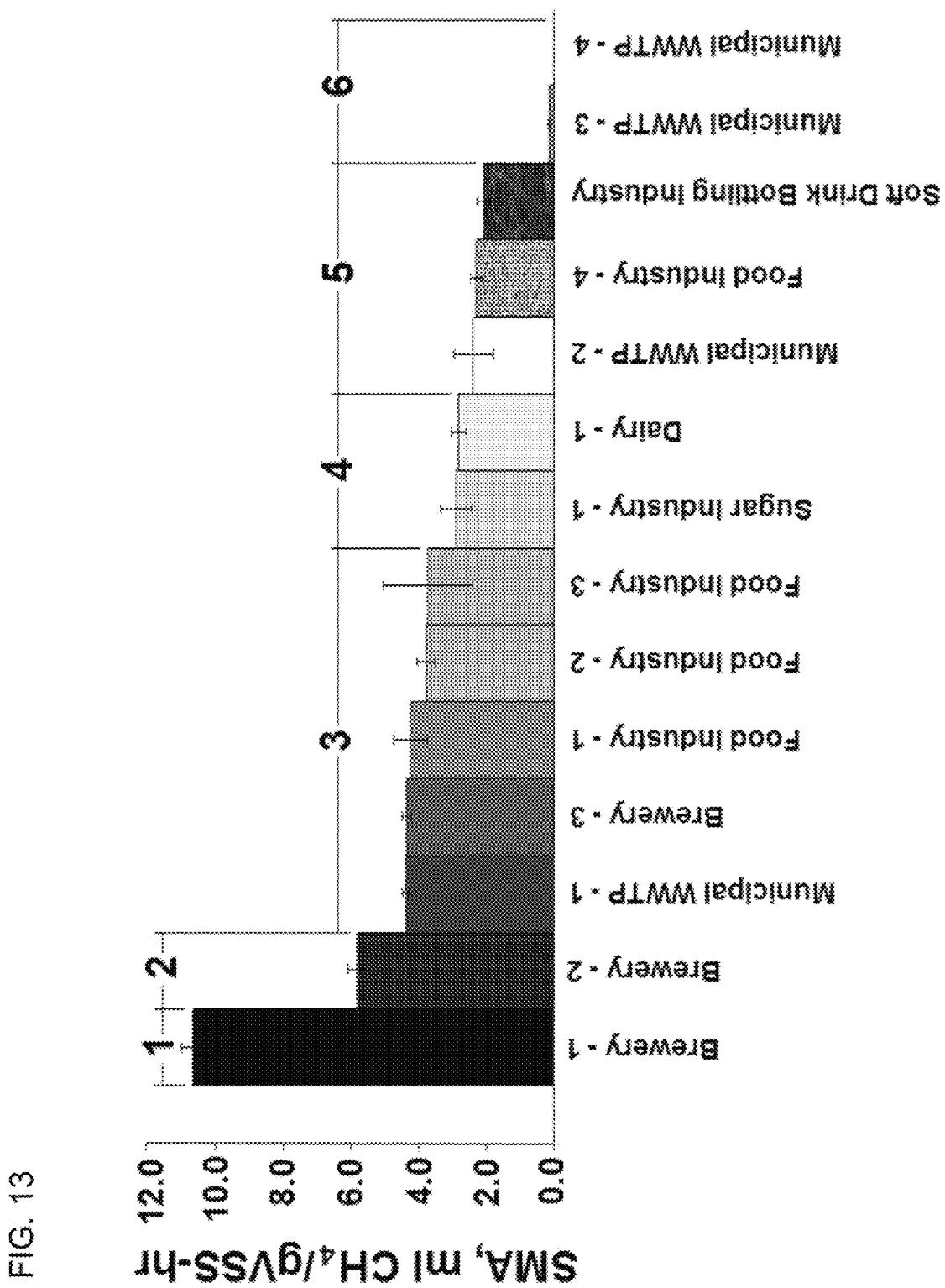
FIG. 13 shows the SMA results for the anaerobic biomass samples from full-scale anaerobic reactors arranged in descending order.

Average SMA values varied over two orders of magnitude. The SMA values were grouped using farthest neighbor algorithm and Student's t statistic for unequal population variances. A probability threshold of 0.05 (95% confidence interval) clustered the biomass samples into six statistically distinct groups, as shown in FIG. 13.

Figure 14:
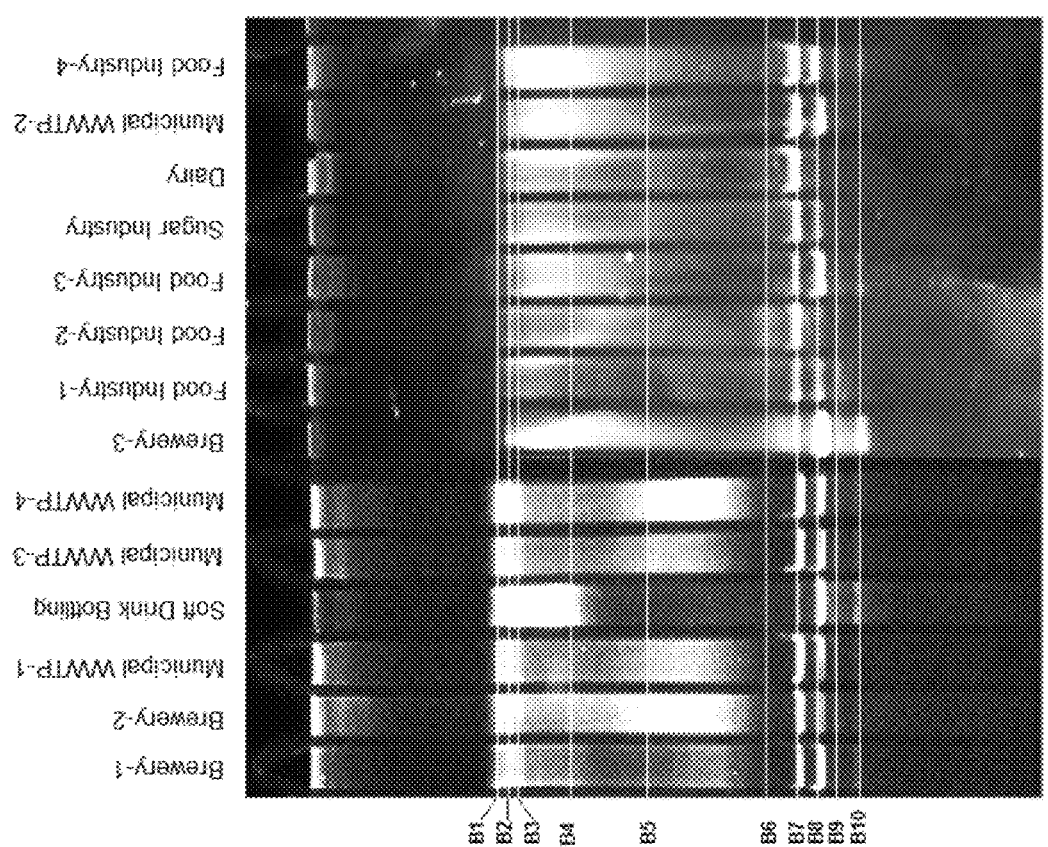
FIG. 14 illustrates the DGGE banding pattern obtained for mcrA gene analysis. B1-B10 represent different DGGE bands.

DGGE provides a genetic fingerprint of the microbial diversity based on the physical separation of unique nucleic acid sequences (Muyzer et al., 1999). DGGE banding patterns for the mcrA gene were generated for biomass samples and compared to SMA results using PCA. FIG. 14 shows the mcrA gene banding pattern obtained for DGGE analysis.

Figure 15:
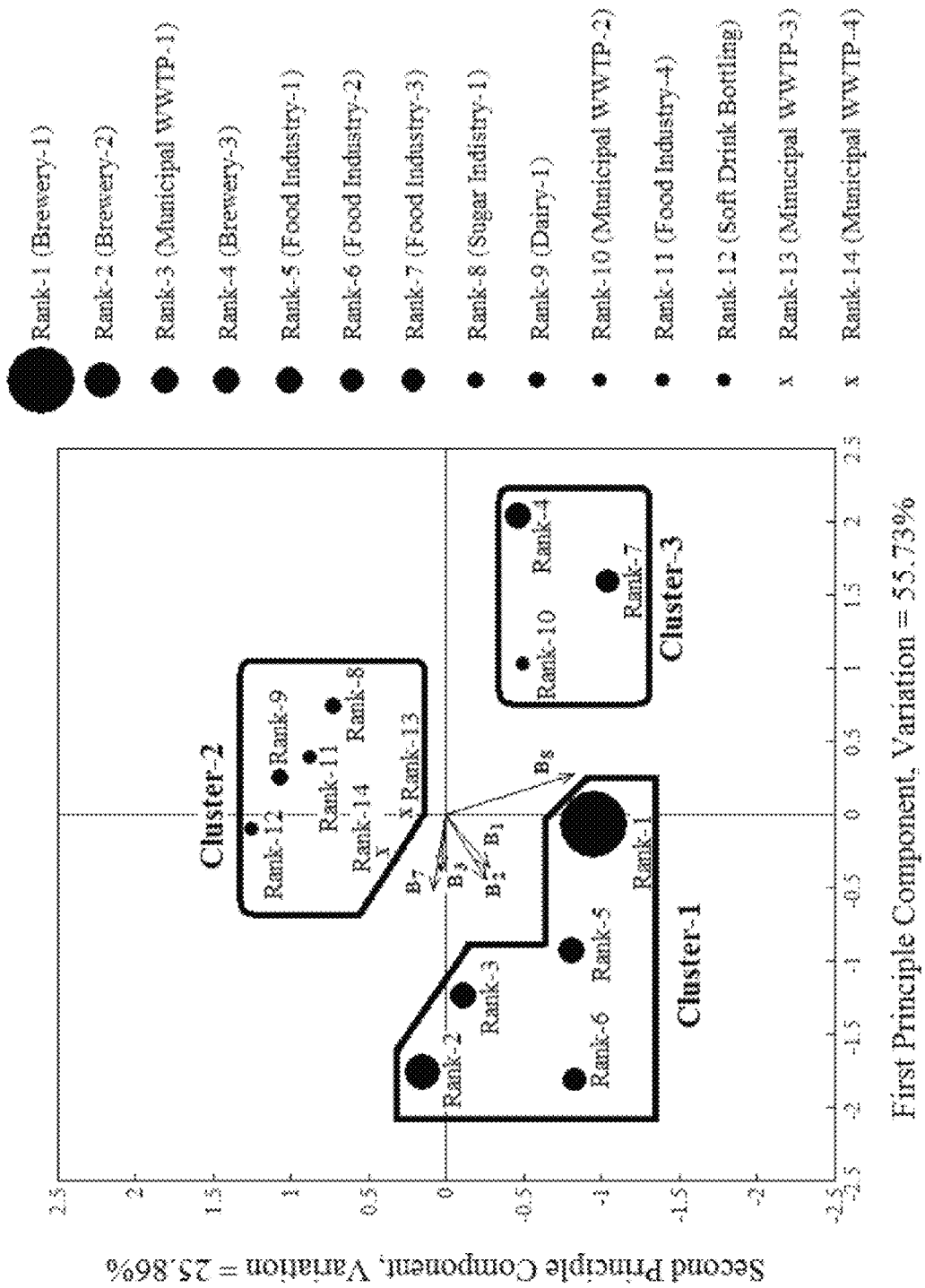
FIG. 15 illustrates the principle component analysis using DGGE band intensities.

The first two principle components based on banding patterns were employed as x- and y-coordinates, respectively, and explained 81.6% of the total densitometric data variation of banding patterns (see FIG. 15). In FIG. 15, SMA results were superimposed by representing biomass samples with higher SMA with larger diameter circles. Two samples were represented by 'x' symbols because of their negligible SMA.

PCA indicated a possible underlying relationship between SMA and DGGE banding patterns. Biomass samples clustered in three groups based on principle component coordinates (see FIG. 15). Clusters 1 and 2 tended to encompass biomass having high and low SMA ranks, respectively. Therefore, the banding patterns generally related to SMA ranks. Projections of the five bands with the highest contribution to DGGE data variability ($B_1$, $B_2$, $B_3$, $B_7$ and $B_8$) are also shown in FIG. 15. Bands $B_1$ and $B_2$ contributed to the high-SMA cluster (Cluster 1). Organisms represented by these bands may have an important metabolic function leading to higher SMA values. Clones extracted from these bands revealed that band B1 consisted of organisms that shared 88-89% sequence similarity with *Methanospirillum hungatei* (GenBank accession no. AF313805), band B2 consisted of organisms that shared 93-98% sequence similarity with *Methanobacierium bijingense* (GenBank accession no. EF465106). In the past, researchers have found average sequence similarities for mcrA genes within a genus and family were 88.9 and 79% respectively (Steinberg and Regan, 2008). It is important to note that both the bands that contributed to high-SMA cluster represented methanogens that have hydrogenotrophic metabolism. This finding underlines the fact that hydrogenotrophic methanogens play a very important role in anaerobic metabolism of propionate (McCarty and Smith, 1986).

Biomass from an upflow anaerobic sludge blanket (UASB) reactor treating brewery wastewater (Brewery-1) demonstrated the most rapid specific propionate conversion to $CH_4$ (10.65±0.36 mL $CH_4$/gVSS-hr). This culture was enriched for propionate utilization and demonstrated an SMA value of 10.65±3.3 mL $CH_4$/gVSS-hr after 580 days of enrichment. This culture was used in the subsequent bioaugmentation investigation.

Recovery of Organically Overloaded Digesters.

Figure 16:
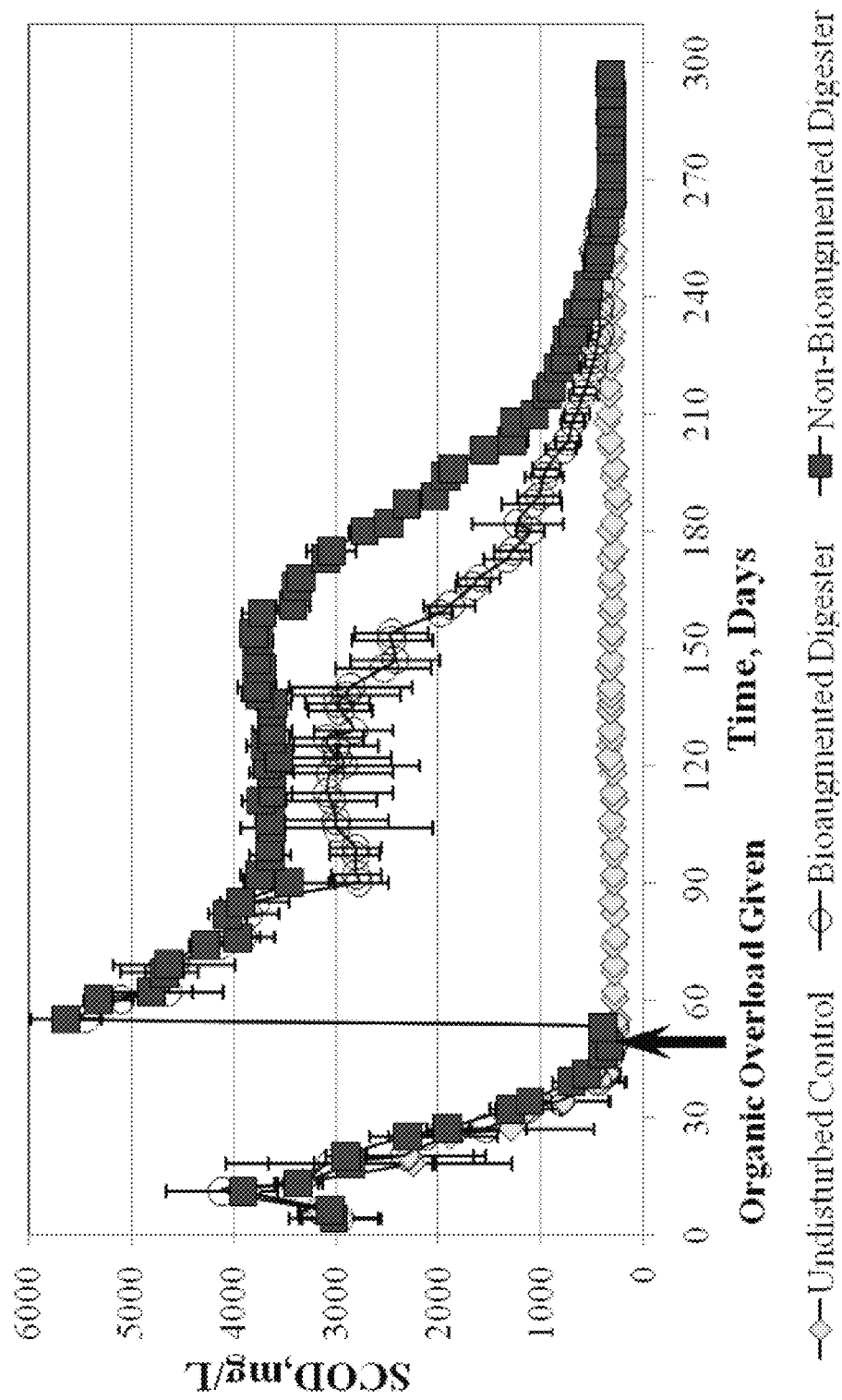
FIG. 16 illustrates the effluent SCOD of digesters. Error bars represent standard deviation among four replicates. Most error bars are small and not visible.

Before the organic overload, all digesters required about 40 days (4 SRTs) to attain an average quasi steady-state effluent SCOD concentration of 290±150 mg/L (see FIG. 16). The shock organic overload was administrated on Day 57 and resulted in an increase in effluent SCOD concentrations to 5000±750 mg/L for all overloaded digesters, as shown in FIG. 16. Following the organic overload, the effluent SCOD started to decrease. Approximately 6 SRTs after the overload, the influence of bioaugmentation was apparent in terms of the lower effluent SCOD concentration of bioaugmented digesters as compared to non-bioaugmented digesters (see FIG. 16). The time required for organically overloaded digester effluent SCOD to decrease below 1000 mg/L was used as one measure of recovery time. Bioaugmented digesters required 25 days less to attain 1000 mg SCOD/L as compared to non-bioaugmented digesters (p<0.03).

Figure 17:
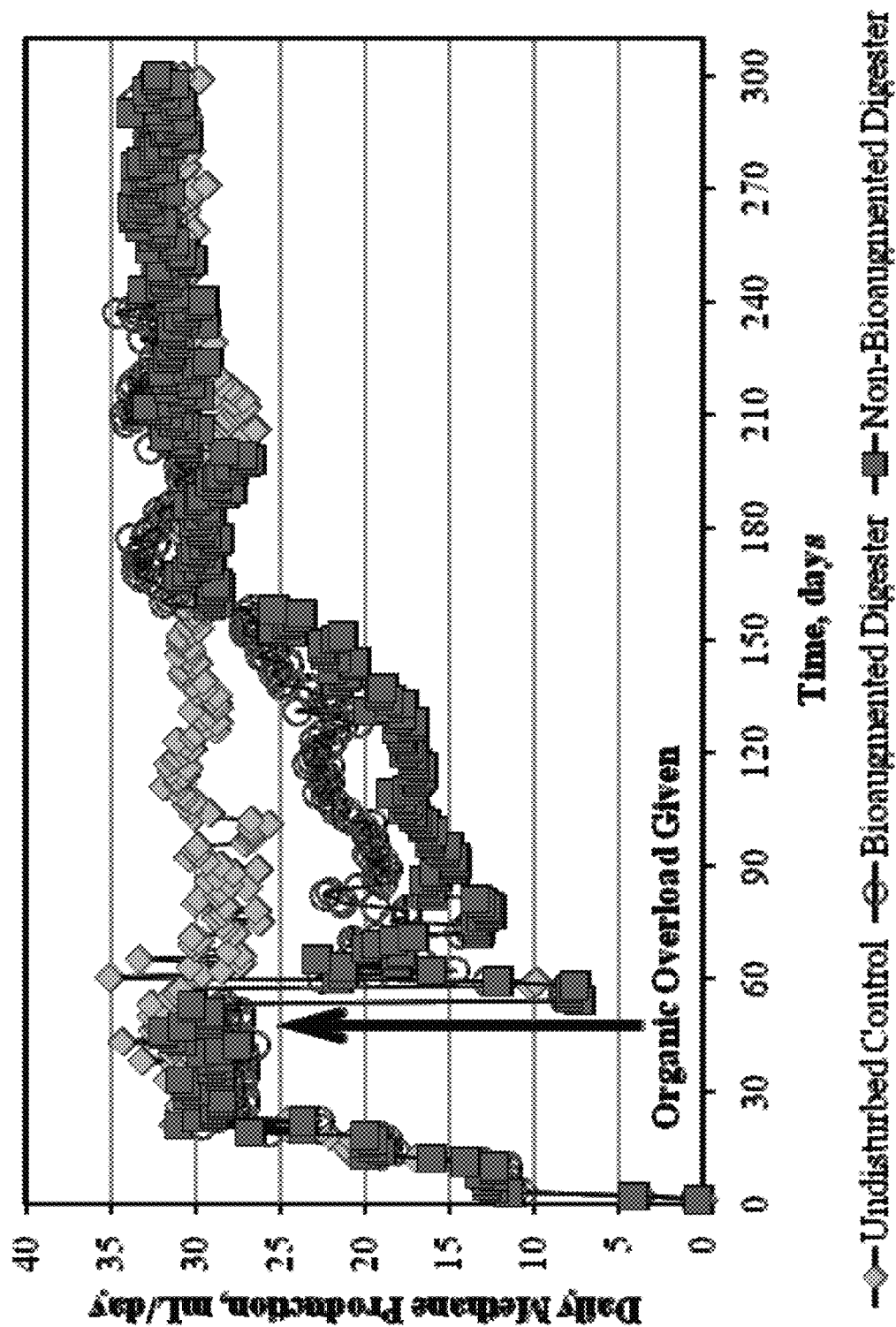
FIG. 17 illustrates the average daily $CH_4$ production from digesters. Error bars not shown for visual clarity.

Before organic overload, all digesters reached an average quasi steady-state $CH_4$ production rate of 32±4 mL $CH_4$/day after 40 days (4 SRTs). Following the organic overload on Day 57, $CH_4$ production from the overloaded digesters decreased to 18±13 mL $CH_4$/day (see FIG. 17). Daily $CH_4$ production began to recover after the organic overload. The time required to attain a $CH_4$ production rate of 25 mL $CH_4$/day was arbitrarily chosen to define the $CH_4$ production recovery period. The bioaugmented digesters required 28 days less to achieve 25 mL $CH_4$/d after overload as compared to non-bioaugmented digesters (p<0.01).

Figure 18:
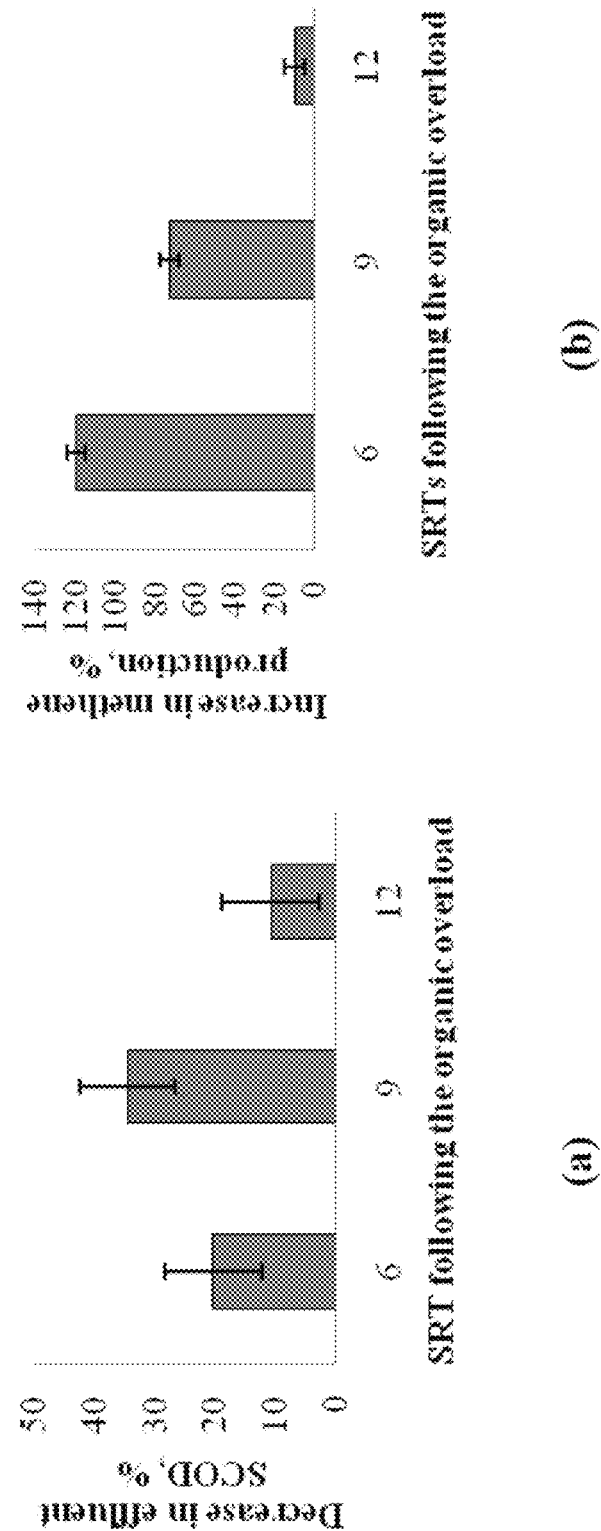
FIG. 18 illustrates (a) decrease in effluent SCOD concentration from bioaugmented digesters as compared to non-bioaugmented digesters; and (b) increase in $CH_4$ production rate from bioaugmented digesters as compared to non-bioaugmented digesters. Error bars represent standard error among replicates.

The percent difference between bioaugmented and non-bioaugmented digester effluent SCOD concentrations was evaluated at 6, 9 and 12 SRTs following the organic overload (see FIG. 18(a)). The influence of bioaugmentation persisted for more than 15 SRTs following the shock overload. For example, the effluent SCOD of bioaugmented digesters was still lower than that of controls after Day 210. This observation is in contrast to the findings of others that bioaugmenting an anaerobic filter with methanogenic cultures enriched for propionate and butyrate did not speed up the recovery following an organic overload (Lynch et al., 1987). The reason for the difference may be because our bioaugmentation culture was supplied on a daily basis throughout the recovery period, whereas the previous researchers (Lynch et al., 1987) supplied the bioaugmentation culture only once, possibly leading to washout.

The percent difference between bioaugmented and non-bioaugmented digester $CH_4$ production rates was evaluated at 6, 9 and 12 SRTs following the organic overload (see FIG. 18(b)). Bioaugmented digesters consistently demonstrated higher average $CH_4$ production rates than non-bioaugmented digesters, even after 12 SRTs following the organic overload.

Conclusions

The SMA values of biomass samples from various full-scale anaerobic reactors can differ greatly. The SMA values against propionate for biomass samples tested herein varied over two orders of magnitude. Therefore, seed biomass for new reactors should be chosen carefully, and activity testing is recommended when selecting seed biomass.

Comparison of DGGE banding patterns for the mcrA gene with SMA values for 14 biomass samples indicate an underlying relation between methanogenic community structure and activity. Presence of hydrogenotrophic methanogens closely related to *Methanospirillum hungatei* and *Methanobacterium beijingense* increased SMA of an anaerobic culture against propionic acid. However, more research is required to establish a true structure-activity relationship (SAR). In the future, SARs or quantitative SARs (QSARs) may be developed, and more highly-defined microbial communities may be employed to improve specific aspects of anaerobic digester performance.

Bioaugmentation is a promising approach to improve digester operations after transient upsets, but more work is required to determine conditions under which bioaugmentation will result in successful application. Under the conditions studied, bioaugmentation with a propionate-utilizing enrichment was successful, and decreased the recovery time of digesters following an organic overload. Biogas and $CH_4$ production rates and effluent SCOD values returned to pre-upset values more quickly when bioaugmentation was implemented. In addition, the benefits of bioaugmentation (lower effluent SCOD, higher $CH_4$ production) were evident for an unexpectedly long time after upset (i.e., >12 SRTs). Therefore, bioaugmentaiton improves long-term performance. Future research should address the changes in microbial community structure and long-term system performance that may occur in anaerobic systems when bioaugmentation is practiced.

References for Example 3

Altschul, S. F., Madden, T. L., Schaffer, A. A., Zhang, J., Zhang, Z., Miller, W., and Lipman, D. J. (1997) "Gapped BLAST and PSI-BLAST: A New Generation of Protein Database Search Programs." *Nucleic Acids Res*. 25: 3389-3402.

American Public Health Association (APHA), American Water Works Association (AWWA), Water Environment Federation (WEF) (1998) *Standard Methods for the Examination of Water and Wastewater* (20th ed.). APHA et al.

Bidle, K. A., Kastner, M., and Bartlett, D. H. (1999) "A Phlylogenetic Analysis of Microbial Communities Associated With Methane Hydrate Containing Marine Fluids and Sediments in the Cascadia Margin (ODP site 829B)." *FMES Microbiology Letters*. 177.1:101-108.

Dhillon, A., Lever, M., Lloyd, K. G., Albert, D. B., Sogin, M. L., and Teske, A. (2005) "Methanogen Diversity Evidenced by Molecular Characterization of Methyl Coenzyme M Reductase A (mcrA) Genes in Hydrothermal Sediments of the Guaymas Basin." *Applied Environmental Microbiology*. 71.8:4592-4601.

Earl, J., Hall, G., Pickup, R. W., Ritchie, D. A., and Edwards, C (2003) "Analysis of Methanogen Diversity in a Hypereutrophic Lake Using PCR-RFLP Analysis of mcr Sequences." *Microbial Ecology*. 46.2:270-278.

Galand, P. E., Saarnio, S., Fritze, H., Yrjald, K. (2002) "Depth Related Diversity of Methanogen Archaea in Finnish Oligotrophic Fen". *FEMS Microbial Ecol*. 42.3: 441-449.

Guiot, S. R., Tartakovsky, B., Lanthier, M., Levesque, M. J., Manuel, M. F., Beaudet, R., Greer, C. W., and Villemur, R. (2002) Strategies for Augmenting the Pentachlorophenol Degradation Potential of UASB Anaerobic Granules. *Water Science and Technology*. 45.10: 35-41.

Hales, B. A., Edwards, C., Ritchie, D. A., Hall, G., Pickup, R. W. and Saunders, J. R. (1996) "Isolation and Identification of Methanogen-Specific DNA from Blanket Bog Peat by PCR Amplification and Sequence Analysis." *Applied Environmental Microbiology*. 62.2:668-675.

Juottonen, H., Galand, P. E., and Yrjala, K. (2006) "Detection of Methenogenic Archaea in Peat: Comparison of PCR Primers Targeting the mcrA Gene." *Research in Microbiology*. 157.10:914-921.

Lenz, M., Enright, A. M., O'Flaherty, V., van Aest, A. C., and Lens P. N. L. (2009) Bioaugmentation of UASB Reactors with Immobilized *Sulfurospirillum barnesii* for Simultaneous Selenate and Nitrate Removal. *Applied Microbiology and Biotechnology*, 83.2: 377-388.

Lloyd, D., Thomas; K. L., Hayes, A., Hill, B., Hales, B. A., Edwards, C., Saunders, J. R., Ritchie, D. A., and Upton, M. (1998) "Micro-Ecology of Peat: Minimally Invasive Analysis Using Confocal Laser Scanning Microscopy, Membrane Inlet Mass Spectrometry and PCR Amplification of Methanogen-Specific Gene Sequences." FMES *Microbiology Ecology*. 25.2:179-188.

Lueders, T., Chin, K. J., Conrad, R., and Friedrich, M (2001) "Molecular Analysis of Methyl-Coenzyme M Reductase α-Subunit (mcrA) Gene in Rice Field Soil and Enrichment Cultures Reveal the Methanogenic Phenotype of a Novel Archaeal Lineage." *Environmental Microbiology*. 3.3:194-204.

Luton, P. E., Wayne, J. M., Sharp, R. J., and Riley, P. W. (2002) The mcrA Gene as an Alternative to 16S rRNA in the Phylogenetic Analysis of Methanogen Populations in Landfill. *Microbiology*. 148: 3521-3530.

Lynch, N., Daniels L., and Parkin, G. F. (1987) Bioaugmentation of Stressed Anaerobic Filters with Methanogenic Enrichment Cultures. *Proceedings of the 42nd Industrial Waste Conference*. (pp. 285-296). West Lafayette, Ind.: Purdue University.

McCarty, P I. and Smith, D. P. (1986) Anaerobic Wastewater Treatment. *Environmental Science and Technology*. 20.12: 1200-1206.

Muyzer, G. (1999) DGGE/TGGE a Method for Identifying Genes from Natural Ecosystems. *Current Opinion in Microbiology*. 2: 317-322.

Nercessian, D., Upton, M., Lloyd, D., and Edwards, C. (1999) "Phylogenetic Analysis of Peat Bog Methanogen Population." *FMES Microbiology Letters*. 173.2:425-429.

Nielsen, H. B., Mladenovska, Z., and Ahring, B. K. (2007) Bioaugmentation of a Two-Stage Thermophilic (68° C./55° C.) Anaerobic Digestion Concept for Improvement of the Methane Yield from Cattle Manure. *Biotechnology and Bioengineering*. 97.6: 1638-1643.

Ohkuma, M., Noda, S., Horikoshi, K. and Kudo, T., (1995) "Phylogeny of Symbiotic Methanogens in the Gut of the Termite *Reticulitermes speratur*." *FMES Microbiology Letters*. 134.1:45-50.

Owen, W. F., Stuckey, D. C., Healy, Jr., J. B., Young, L. Y., and McCarty P. L. (1979) Bioassay for Monitoring Biochemical Methane Potential and Anaerobic Toxicity. *Water Research*. 13: 485-492.

Rastogi, G., Ranade, D. R., Yeole, T. Y., Patole, M. S, and Shouche, Y. S. (2008) "Investigation of Methanogen Population Structure in Biogas Reactor by Molecular Characterization of Methyl-Coenzyme M Reductase A (mcrA) Genes". *Bioresource Technology* 99.13:5317-5326.

Rittmann, B. E. and Whiteman, R. (1994) Bioaugmentation: A Corning of Age. *Water Quality International*. 1: 12-16.

Sambrook, J. and Russell, D. W. (2001) *Molecular Cloning: A Laboratory Manual*. 3rd ed. Cold Spring Harbor Laboratory Press. Cold Spring Harbor, N.Y.

Schauer-Gimenez, A. E., Zitomer, D. H., Maki, J. S, and Struble, C. A. (2010) *Bioaugmentation for Improved Recovery of Anaerobic Digesters after Toxicant Exposure. Water Research,* 44.12:3555-3564.

Smith, D. P., and McCarty, P. L. (1990) Factors Governing Methane Fluctuations Following Shock Loading of Digesters. *Research Journal of the Water Pollution control Federation.* 62.1: 58-64.

Steinberg, L. M, and Regan, J. M. (2008) "Phylogenetic Comparison of the Methanogenic Communities from an Acidic, Oligotrophic Fen and an Anaerobic Digester Treating Municipal Wastewater Sludge." *Applied and Environmental Microbiology,* 74.21:6663-6671.

Tawfiki Hajji, K., Lepine, F., Bisaillon, J. G., Beaudet, R., Hawari, J., and Guiot, S. R. (2000) Effects of Bioaugmentation Strategies in UASB Reactors with a Methanogenic Consortium for Removal of Phenolic Compounds. *Biotechnology and Bioengineering.* 67.4: 417-423.

Thauer, R. K. (1998) "Biochemistry of Methanogenesis: A Tribute to Marjory Stephenson." *Microbiology.* 144:2377-2406.

Ufnar, J. A., Ufnar, D. F., Wang, S. Y., and Ellender, R. D. (2007) "Development of a Swine-Specific Fecal Pollution Marker Based on Host Differences in Methanogen mcrA Genes." *Applied and Environmental Microbiology,* 73.6: 5209-5217.

Wilms, R., Sass, H., Köpke, B., Cypionka, H., and Engelen, B. (2007). "Methane and Sulfate Profiles Within the Subsurface of a Tidal Flat are Reflected by the Distribution of Sulfate-Reducing Bacteria and Methanogenic Archaea." *FMES Microbiology Ecology.* 59.3:611-621.

Woese, C. R. and Fox, G. E. (1977) "Phylogenetic Structure of the Prokaryotic Domain: the Primary Kingdoms." *Proceedings of the National Academy of Sciences of the United States of America.* 74.11: 5088-5090.

Example 4

Reference is made to Bhattad, U. H., Maki, J. S., Struble, C. A, Schauer-Gimenez, A. E., and Zitomer, D. H., "Culture Conditions and Cryoprotectant Addition Influences Methanogenic Activity After Freeze-Drying in Air," in proceedings of International Water Association (IWA) 12th. World Congress on Anaerobic Digestion, Guadalajara, Mexico, October 31st-November 4th, 5 pp, the content of which is incorporated herein by reference in its entirety.

Abstract

Practitioners often rely on undefined microbial communities, that predominate in an anaerobic system. In the near future, however, more methanogenic communities may be customized to fit different applications. Therefore, practical methods to preserve and store customized methanogenic cultures would be helpful. In this study, freeze-drying in air to preserve methanogenic cultures was studied. All cultures were enriched for over one year and received $H_2/CO_2$; one also received air (40 mg $O_2$/L-day), and another received glucose (40 mg/L-day). All cultures maintained 30 to 79% of their original $H_2$-utilizing activity after being freeze dried in air. The culture receiving air during enrichment consistently exhibited higher activity before freeze-drying, after freeze-drying and after being held under conditions simulating 20 years of storage subsequent to freeze-drying. Archaeal clone libraries for each were constructed. The micro-aerobic culture clone library contained a high relative abundance of unstudied phylotypes that could only be classified as archaea; some may represent unique methanogens that are more tolerant of drying and storage in an air atmosphere. Cryoprotectant addition (10% glucose) also resulted in higher activities after freeze drying as well as storage.

Introduction

Methanogenesis requires the presence of specific microbial communities composed of different trophic groups in syntrophic relationships (Speece, 2008). The different communities present in various bioreactors are complex and relatively difficult to define. Therefore, the typical, current engineering approach is to pump waste into a digester and rely on the microorganisms that predominate. However, molecular tools are now being used to identify the organisms involved and understand the link between microbial community structure and digester function or activity (Kolukirik et al., 2004). It is possible that, in the near future, methanogenic microbial communities will be customized for different applications.

In general, methanogens are slow-growing organisms and require significant time to reproduce. Therefore, it would be beneficial if various defined methanogenic cultures could be easily preserved for research and practical applications. Preserved methanogenic cultures could be developed for the following: (1) future research or easy shipment to other laboratories, (2) dissemination and use for standardized tests, such as biochemical methane potential and anaerobic toxicity assays, (3) seeding or re-seeding of laboratory and full-scale reactors, and (4) bioaugmentation of full-scale digesters to increase biogas production and process stability. Bioaugmentation may be an especially beneficial approach to improve anaerobic bioprocesses. Bioaugmentation has been applied to improve the anaerobic degradation rate of difficult-to-degrade compounds such as phenols, cresols, tetrachloroethylene, fat, oil and grease, cattle manure, cellulose and hemicellulose (Schauer-Gimenez et al., 2010). Bioaugmentation has also been used to reduce odor (Duran et al., 2006), shorten the start-up time of new digesters, and decrease the recovery time of organically overloaded reactors (Saravanane et al., 2001), and digesters exposed to a toxicant (Schauer-Gimenez et al., 2010).

The use of wet cultures may be incompatible with some commercial needs. Drying reduces the mass and facilitates less expensive shipping and handling (Aguilera and Karel, 1997). Freezing followed by drying (i.e., freeze-drying) is a preferred technique for preserving and storing microbial cultures in the laboratory as well as in full-scale bio-industries, but "it appears to still be a science based on empirical testing rather than facts and tested theories. The methodologies could be different for different species" (Morgan et al., 2006). Malik (1990) describes several microbial cultures that are sensitive to freezing or freeze-drying including various anaerobes. Major losses in cell viability may occur during each of the three stages of preservation: freezing, drying, and storage.

Culture Freezing.

The process of freezing and, especially, the rate of freezing influence the viability of cells. Freezing can be done either slowly or rapidly. Extra-cellular ice crystal formation, long-term exposure to high solute concentrations, and excessive cell dehydration in slow freezing can contribute to extensive cell damage (Aguilera and Karel, 1997). As Simione and Brown (1991) have written, "[i]n rapid freezing, cell damage may be reduced, and intracellular ice formation is the major contributing factor to cell injury. Rapid freezing in liquid nitrogen is considered to result in less cell damage, but can result in more difficulty during the subsequent drying process." Staab and Ely (1987) employed a shell-freezing method using liquid nitrogen to freeze sensitive anaerobic bacteria including 15 species from the genera *Clostridium, Propionicbacterium, Bifidobacterium, Eubacterium, Bactericides, Fusobacterium, Peptococcus*, and *Peptostreptococcus*. For this method, the culture was swirled in a flask, immersed in liquid nitrogen and the material frozen as a thin shell on the inner surface of the flask. Results showed >50% cell viability after freeze-drying.

Culture Drying.

Drying is used to create stable dried cultures with low residual moisture content (RMC) by removing the moisture from frozen or wet cultures. Low RMC values typically increase survival during storage. Below 10% moisture content, metabolic processes slow or become non-measureable. The lowest practically achievable RMC in the laboratory is between 4 and 7% using freeze-drying (Aguilera and Karel, 1997). Minimum RMC values observed in the laboratory may be impractical on an industrial scale due to scale-up factors and tradeoffs between product yield, stability and cost (Kadam, 1991).

The freeze-drying cycle proceeds in two stages: primary drying and secondary drying. In primary drying, the frozen water is removed by sublimation of ice crystals to water vapor. The major fraction of water is removed during primary drying, but some bound water remains in the dried product. Bound water is trapped within the solid matrix and can take a long time to remove. The bound water is removed during secondary drying at low pressure and low condenser temperature. Secondary drying reduces the RMC and increases the stability of final products (Simione and Brown, 1991). Ideally, the end-point of secondary drying is determined by analysis of the RMC within the freeze-dried products (Morgan et al., 2006). Often, secondary drying is performed for the same length of time as primary drying if the resulting RMC is found to be acceptable (Kadam, 1991).

Culture Storage.

The shelf-life of a freeze-dried culture is highly dependent on the storage temperature and moisture content. Morgan et al., (2006), discussed that storage temperatures of −20° C. and 20° C. cause increased loss of cell viability as compared to 4° C. Sakane and Kuroshima (1997) demonstrated that accelerated storage of liquid-dried bacterial cultures for 2 weeks at 37° C. can simulate 20 years of storage at 5° C. under vacuum.

Cryoprotectants.

The viability of freeze-dried culture can be improved by adding sugars and other carbohydrates as protective agents prior to freezing or drying. The cryoprotectants are viscous and form a glassy state within and around the cell to protect against membrane damage which occurs due to formation of ice crystals during freezing and increases in liquid water solute concentration during freezing and drying (Morgan et al., 2006). An increase in cell viability after freezing and drying depends on the type of protective agent used, and its selection is crucial since some cryoprotectants are toxic to different microbes (Hubalek, 2003).

Preservation of anaerobes using freeze-drying was reported under strict anaerobic conditions, but very limited information regarding methanogenic culture preservation in air exists, possibly due to their high sensitivity to oxygen. The preservation of methanogenic cultures in air would make the process more convenient and economical, but is challenging, and effective preservation and storage methods are needed. In this study, we investigated freeze-drying in an air atmosphere as a method of preservation for three methanogenic cultures. Activity was measured after drying as well as after drying and simulated long-term storage. The effectiveness of enriched culture conditions and cryoprotectant addition was determined.

Materials and Methods

Enrichment Cultures.

Three methanogenic enrichment cultures were developed as described elsewhere (Schauer-Gimenez et al., 2010). Briefly, reactors were seeded with 2 L of anaerobic municipal sludge and operated in daily feed-and-draw mode over two years at 35° C. and a 15-day retention time. All cultures (Culture 1, 2 and 3) received basal nutrient medium (see below) and $H_2$:$CO_2$ (1:1, v/v ratio) in the headspace every day. In addition, Culture 2 received glucose (40 mg/L-day), whereas Culture 3 received air (40 mg $O_2$/L-day). The mass of $O_2$ theoretically satisfied less than 6% of the oxygen demand. Therefore, the culture dissolved $O_2$ concentration was expected to be negligible. Basal nutrient medium contained the following [mg/L]: $NH_4Cl$ [400]; $MgSO_4.6H_2O$ [250]; KCl [400]; $CaCl_2.2H_2O$ [120]; $(NH_4)_2HPO_4$ [80]; $FeCl_3.6H_2O$ [55]; $CoCl_2.6H_2O$ [10]; KI [10]; yeast extract [100]; the trace metal salts $MnCl_2.4H_2O$, $NH_4VO_3$, $CuCl_2.2H_2O$, $Zn(C_2H_3O_2)_2.2H_2O$, $AlCl_3.6H_2O$, $NaMoO_4.2H_2O$, $H_3BO_3$, $NiCl_2.6H_2O$, $NaWO_4.2H_2O$, and $Na_2SeO_3$) [each at 0.5]; $NaHCO_3$ [5000]; and resazurin [1].

Freezing and Drying.

Waste biomass was collected from all reactors over three days, stored at 4° C. in glass bottles sparged with $N_2$:$CO_2$ gas (7:3 v/v), then thickened by centrifugation at 4500 rpm for 10 minutes with and without 10% glucose as a cryoprotectant (Colleran et al., 1992). Thickened biomass was transferred to 75 mL freeze-drying flasks (Millrock Technology, Kingston, N.Y., USA) and shell frozen by immersion in liquid nitrogen for approximately 10 minutes (Staab and Ely, 1987). Frozen biomass was then dried using a bench-top freeze dryer (3GenMP Opti-Dry, Millrock Technology, Kingston, N.Y., USA) at a condenser temperature of −45° C. and vacuum of 13.33 pascal (Kadam, 1991). The primary drying time was determined by monitoring flask temperature using a thermocouple (800024, Sper Scientific Ltd., Scottsdale, Ariz., USA). Primary drying was assumed to be complete when the flask temperature increased to the ambient value. Secondary drying was maintained for a time equal to that of primary drying, as recommended elsewhere (Kadam, 1991).

Short-term and accelerated long-term culture storage. After drying, cultures were analyzed for residual moisture content (RMC) by measuring the total solid (TS), and volatile solids (VS) by standard methods (APHA et al., 1998). Dried cultures were stored in a desiccator containing a $CaCO_3$ dessicant (Drierite®, W. A Hammond Co., Xenia, Ohio, USA) with an air atmosphere at room temperature for two days before activity testing. Long-term storage was simulated by holding cultures in a similar desiccator with air at an elevated temperature of 35° C. for 15 days, as described by others (Sakane and Kuroshima, 1997); this has been shown to produce activity loss similar to storage for 20 years at 5° C. for many microorganisms.

Specific Methanogenic Activity (SMA) Testing Against $H_2$.

Aliquots of dried cultures were rehydrated in 300 mL of nutrient medium containing L-cysteine hydrochloride (500 mg/L) as a reducing agent. The culture activity against $H_2$ for wet cultures, freeze-dried cultures after drying, and freeze-dried cultures after accelerated storage was determined using the SMA protocol described by Coates et al. (1996) implemented. Serum bottles (160 mL) were charged with 25 mL of biomass suspension (<300 mg/L VSS), sparged with a $H_2$:$CO_2$ gas mix (4:1 v/v) and sealed with black balch-type rubber septa and aluminum seals. Bottles were pressurized by injecting 100 mL of the $H_2:CO_2$ gas mix (4:1 v/v) and incubated at 35° C. and 150 rpm in an incubator-shaker (model C25KC, New Brunswick Scientific, Edison, N.J., USA). The volume of gas remaining was measured over time with a glass syringe and water-lubricated glass plunger. After measurement, gas was re-injected into the serum bottle.

The gas volume decrease was calculated from the initial gas volume in test bottles (100 mL) less the gas volume remaining at a given time. The $H_2:CO_2$ gas utilized was calculated as the gas volume decrease less the endogenous control bottle gas volume produced. Methane production was calculated as the volume of $H_2:CO_2$ gas utilized divided by the stoichiometric ratio 4 (i.e., 4 moles of $H_2$ and 1 mole of $CO_2$ produce 1 mole of $CH_4$). Maximum methane production rate (mL $CH_4$/h) was determined by linear regression using the initial points on a graph of cumulative methane produced versus time. SMA (mL $CH_4$/g of VSS-h) was calculated by dividing the maximum methane production rate by the system VSS mass measured by standard methods (APHA et al., 1998). SMA testing, endogenous controls and abiotic controls were run in triplicate. Gas leakage in abiotic controls was negligible throughout the analyses. A one sided Student's West with unequal population variance was used to compare activity data.

Archaeal Community Analysis.

Archaeal communities were analyzed by building clone libraries for a fragment of the 16S rRNA gene using ArchF (5'-TTCCGGTTGATCCYGCCGGA-3' (SEQ ID NO:7)) and ArchR (5'-YCCGGCGTTGAMTCCAATT-3' (SEQ ID NO:8)) primers as described elsewhere (Schauer-Gimenez et al., 2010). DNA was extracted using the PowerSoil DNA Isolation Sample Kit (MoBio Laboratories, Inc., Carlsbad, Calif., USA) and PCR amplified using EconoTaq® PLUS 2× Master Mix (Lucigen Corp., Middleton, Wis., USA). PCR products were cloned using a TOPO TA Cloning® Kit (Invitrogen, Carlsbad, Calif., USA). Transformants were selected by blue-white screening, and direct colony PCR was performed on white colonies. PCR products were cleaned, concentrated, and processed using an UltraClean™ Clean-Up Kit (MoBio Laboratories, Carlsbad, Calif., USA) prior to sequencing at an outside facility (University of Chicago Cancer Research Center). Consensus sequences were assembled, and vector sequences as well as chimeras were removed as described elsewhere (Schauer-Gimenez et al., 2010). The Basic Local Alignment Search Tool (BLAST) was used to identify similar sequences. The SeqMatch program on the Ribosomal Database Project (RDP) website was used to identify taxonomic classifications (Cole et al., 2007).

Results and Discussion

Figure 19:
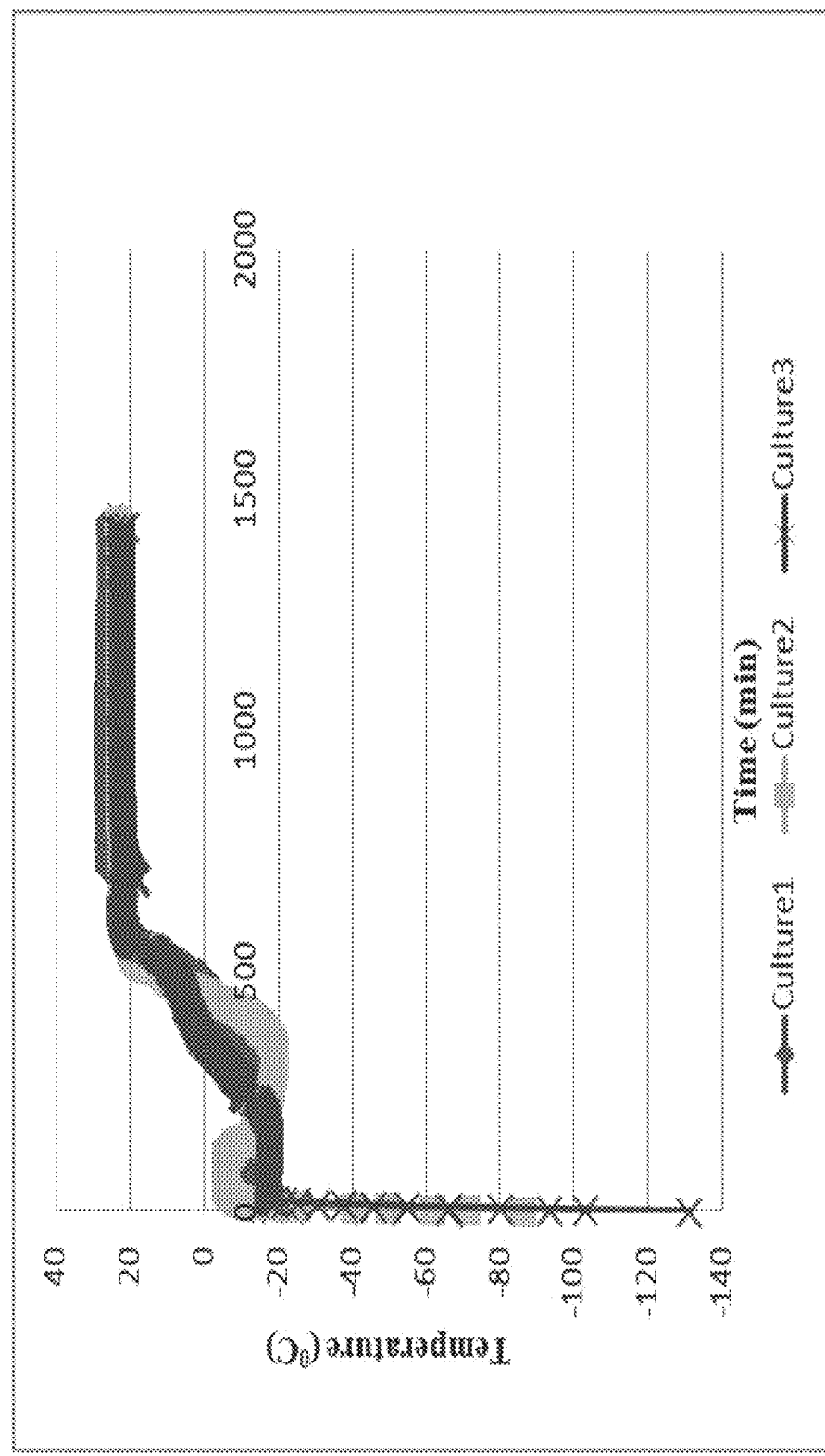
FIG. 19 illustrates freeze-drying behavior of methanogenic cultures.

All three methanogenic cultures maintained $H_2$-utilizing activity after being freeze dried and stored in an air atmosphere. The drying behaviors of all cultures were similar. After 12 h, the drying flask reached the ambient temperature and primary drying was completed (See FIG. 19). Secondary drying was then continued for an additional 12 h to remove bound water and obtain a stable product. The RMC of freeze-dried cultures was between 9 and 13% by mass.

Culture conditions influenced the microbial community structure as well as activities observed before freeze drying, after freeze drying, and after storage. Cultures 1 and 3 consistently demonstrated significantly higher activity (p<0.005) as compared to Culture 2 (See FIGS. 20 and 21). The glucose addition to Culture 2 may have increased the VSS mass associated with fermentative bacteria and acetoclastic methanogens, thus decreasing the $H_2$-utilizing fraction of the total VSS. Therefore, the hydrogenotrophic methanogens may have comprised a lower fraction of the total biomass in Culture 2 and the activity against $H_2$ was lower. This is supported by archaeal community analysis. The relative abundance of sequences related to known hydrogenotrophic methanogens was lower in Culture 2, whereas the relative abundance of sequences related to known acetoclastic methanogens was higher in Culture 2 (See FIG. 22).

Figure 20:
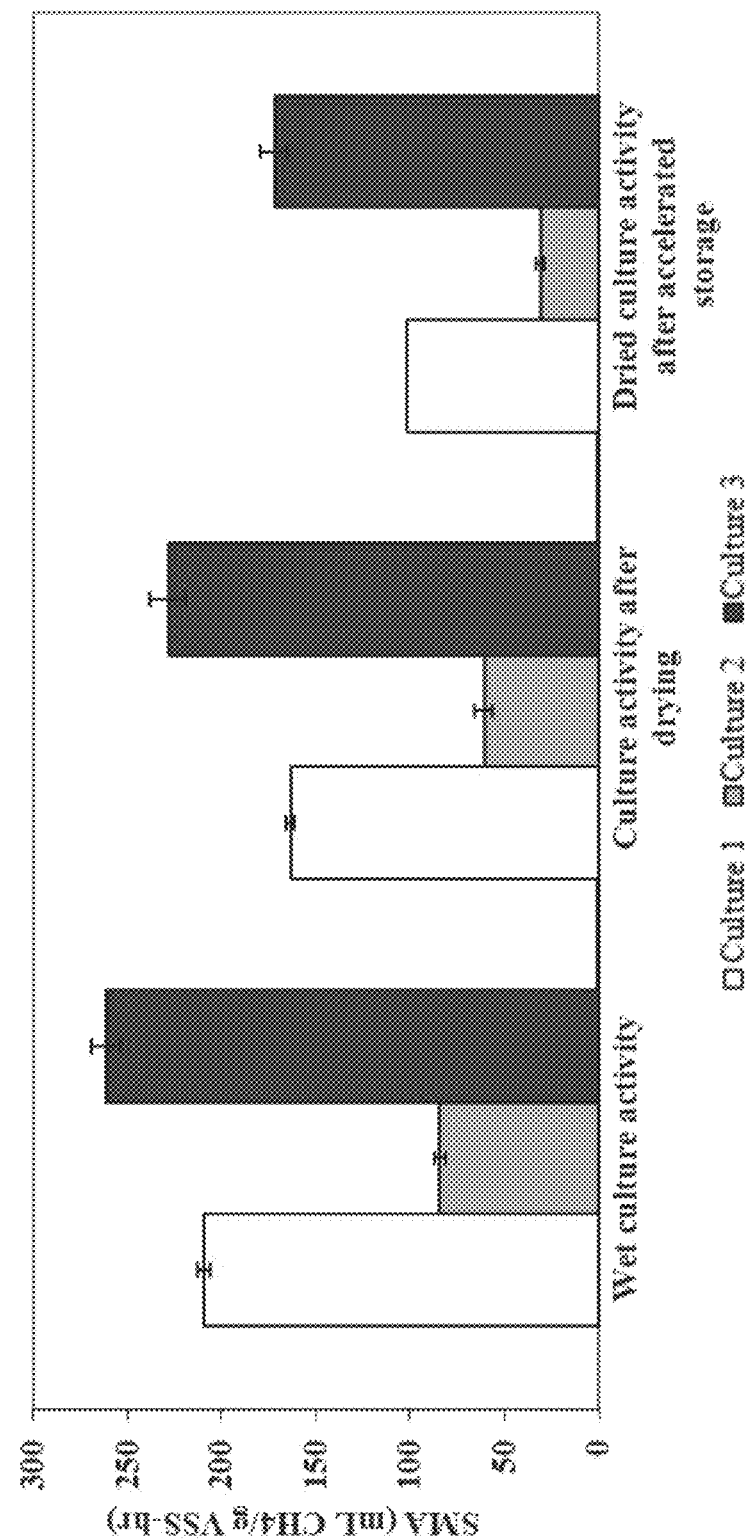
FIG. 20. illustrates methanogenic activity of cultures with cryoprotectant. Error bars represent standard deviation among three replicates.
Figure 21:
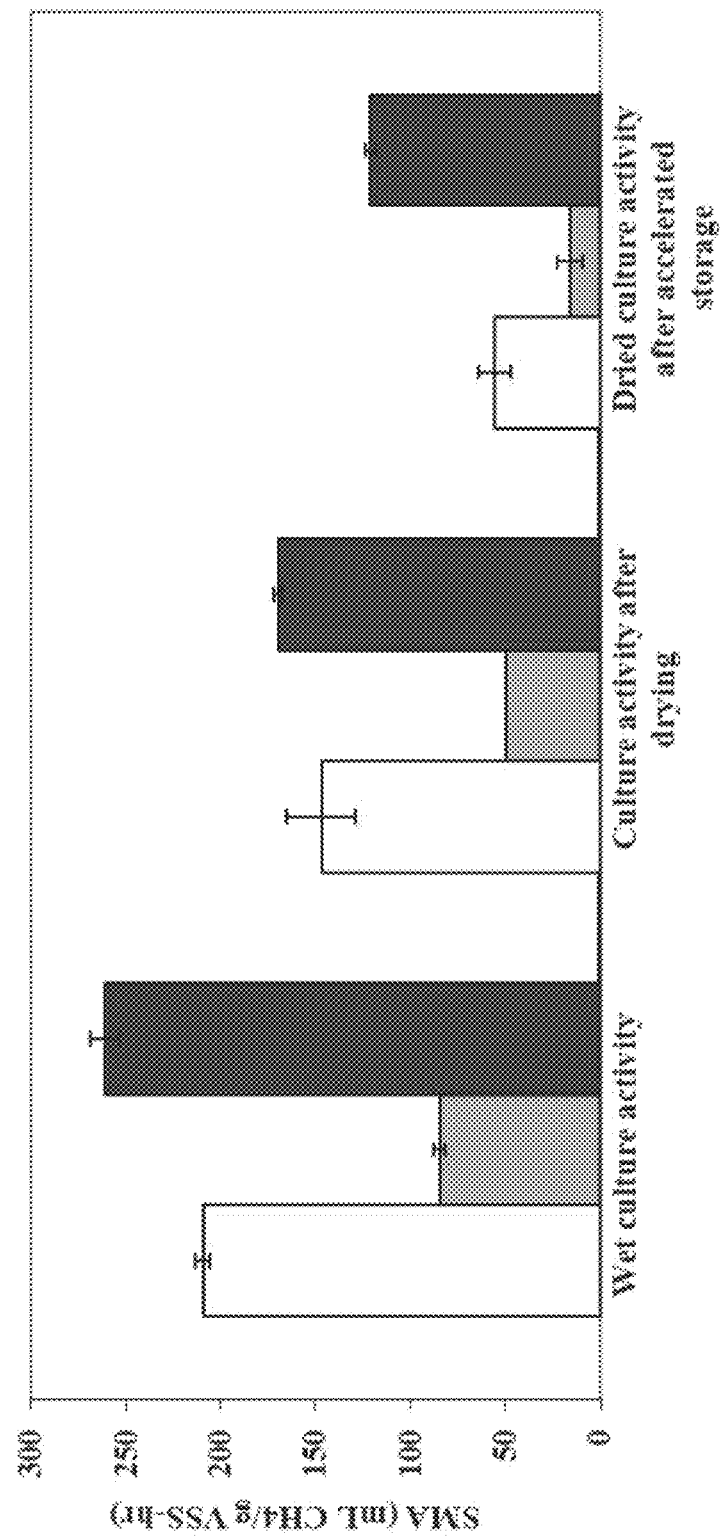
FIG. 21. illustrates methanogenic activity of cultures without cryoprotectant. Error bars represent standard deviation among three replicates.
Figure 22:
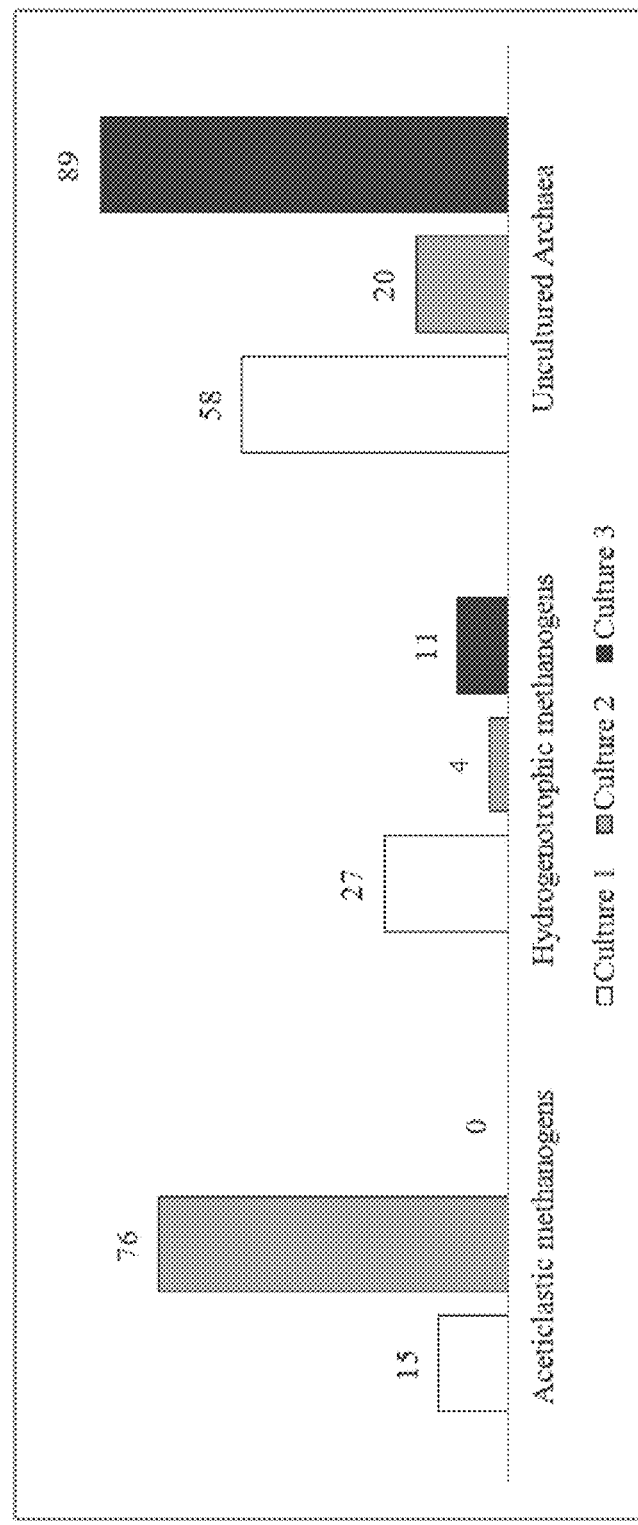
FIG. 22. illustrates percent Archaeal population based on total sequences

The culture 3 which was enriched with a low daily dose of air (i.e., $O_2$) consistantely exhibited higher activity before freeze-drying, after freeze-drying, and after storage following freeze-drying (See FIGS. 20 and 21). Addition of small amount of air shifted the archeal community, causing a higher relative abundance of archaeal phylotypes of unknown phyla (See FIG. 22). The unstudied archaeal phylotypes may be more tolerant of drying and storage in an air atmosphere and may be methanogens. Air addition also resulted in a decrease in the relative abundance of phylotypes closely related to known aceticlastic methanogens (See FIG. 22).

Figure 23:
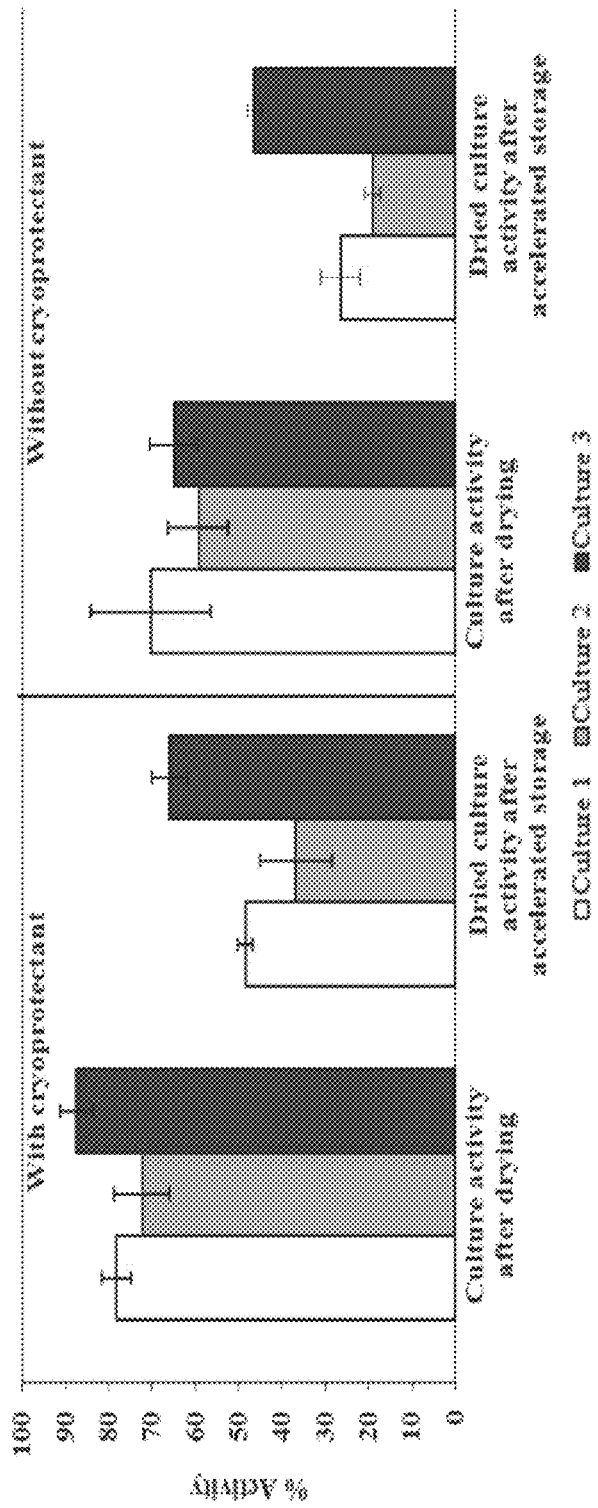
FIG. 23. illustrates percent activity of freeze-dried cultures with and without addition of cryoprotectant with respect to wet cultures. Error bars represent standard deviation among three replicates.

Cryoprotectant addition resulted in higher methanogenic activity after both freeze-drying and storage. The beneficial influence of cryoprotectant addition was more pronounced after accelerated storage than it was after drying (See FIG. 23). The percent activity preserved was calculated as the activity value after freeze-drying or storage divided by the activity value before freeze drying multiplied by 100. The average percent activity preserved after freeze-drying for all cultures was 79% with cryoprotectant and 65% without cryoprotectant, whereas the average percent activity preserved after freeze-drying and subsequent accelerated storage was 50% with cryoprotectant and 30% without cryoprotectant respectively (See FIG. 23). Similar results were discussed by Colleran et al. (1992) for cultures dried and stored under anaerobic conditions. They showed that addition of 10% glucose during freeze-drying resulted in 32% higher activity of granular anaerobic sludge immediately after drying and 48.5% after freeze-drying with seven months of subsequent storage under anaerobic conditions. Berner and Viernstein (2006) demonstrated that 40% of the original viability of a freeze-dried *Lactococcus lactis* strain cultivated under anaerobic conditions at 30° C. was preserved when 15% sucrose was used as a cryoprotectant, but no colony forming units (CFUs) were detected when the cryoprotectant was not added.

Conclusions

Methanogenic activity can be preserved after freeze-drying and storage of active cultures in an air atmosphere. Growth conditions before freeze-drying influenced the hydrogenotrophic activity after freeze-drying. In this regard, methanogenic cultures grown in the presence of air maintained more methanogenic activity after freeze-drying in air as compared to strictly anaerobic cultures. Clone libraries constructed from micro-aerobic methanogenic cultures contained unstudied phylotypes that could only be classified under the domain Archaea (i.e, they could not be resolved to the phylum level). Some of these unstudied archaea may have been unique methanogens that were more tolerant of drying and storage in an air atmosphere; however, additional research is required to confirm this hypothesis. Adding 10% glucose as a cryoprotectant resulted in increased methanogenic activity after freeze drying and after storage of the freeze-dried product. In addition, micro-aerobic culture conditions and glucose addition as a cryoprotectant are practical methods to increase hydrogenotrophic methanogenic activity after freeze-drying in air.

References for Example 4

Aguilera J., Karel M. (1997). Preservation of biological materials under desiccation. *Crit Rev Food Sci Nutr.* 37(3), 287-309.

APHA (American Public Health Association), AWWA (American Waterworks Association), and WEF (Water Environment Federation) (1998). *Standard Methods for the Examination of Water and Wastewater*, 20$^{th}$ edition.

Berner D., Viernstein H. (2006). Effect of protective agents on the viability of *Lactococcus* lactis subjected to freeze-thawing and freeze-drying. *Scientia Pharmaceutica (Sci. Pharm)*. 74, 137-149.

Coates J. D., Coughlan M. F. and Colleran E. (1996). Simple method for the measurement of the hydrogenotrophic methanogenic activity of anaerobic sludges. *J. Microbiol Methods*. 26(3), 237-246.

Cole J., Chai B., Farris R., Wang Q., Kulam S., McGarrell D., Garrity G. and Tiedje J. (2005). The Ribosomal Database Project (RDP-II): sequences and tools for high-throughput rRNA analysis. *Nucleic Acids Res.* 33(Database Issue), D294.

Colleran E., Concannon F., Golden T., Geoghegan F., Crumlish B., Killilea E., Henry M. and Coates J. (1992). Use of methanogenic activity tests to characterize anaerobic sludges, screen for anaerobic biodegradability and determine toxicity thresholds against individual anaerobic trophic groups and species. *Water Science & Technology*, 25(7).

Duran M., Tepe N., Yurtsever D., Punzi V. L., Bruno C. and Mehta R. J. (2006). Bioaugmenting anaerobic digestion of biosolids with selected strains of *Bacillus, Pseudomonas*, and Actinomycetes species for increased methanogenesis and odor control. *Appl Microbiol Blotechnol*. 73(4), 960-966.

Hubalek Z. (2003). Protectants used in the cryopreservation of microorganisms* 1. *Cryobiology*. 46(3), 205-229.

Kadam K. L. (1990). Granulation technology for bioproducts. Informa Healthcare., Dated, May 14, 2010.

Kolukirik M., Ince O. and Ince B. (2004). Changes in acetoclastic methanogenic activity and archaeal composition in a full-scale UASB reactor treating an alcohol distillery effluent, 53-58.

Lange and Ahring (2001). A comprehensive study into the molecular methodology and molecular biology of methanogenic Archaea." *FEMS Microbiology Reviews*. 25: 553-571.

Malik K. A. (1990). A simplified liquid-drying method for the preservation of microorganisms sensitive to freezing and freeze-drying. *J Microbiol Methods*. 12(2), 125-132.

Morgan C., Herman N., White P. and Vesey G. (2006). Preservation of micro-organisms by drying; A review. *J Microbiol Methods*. 66(2), 183-193.

Sakane T., Kuroshima K. (1997). Viabilities of dried cultures of various bacteria after preservation for over 20 years and their prediction by the accelerated storage test. *Microbiol. Cult. Coll*. 13, 1-7.

Saravanane R., Murthy D. and Krishnaiah K. (2001). Bioaugmentation and treatment of cephalexin drug-based pharmaceutical effluent in an upflow anaerobic fluidized bed system. *Bioresour Technol*. 76(3), 279-281.

Schauer-Gimenez A. E., Zitomer D. H., Maki J. S, and Struble C. A. (2010). Bioaugmentation for Improved Recovery of Anaerobic Digesters After Toxicant Exposure. *Water Res.*

Simione F. P., Brown E. M. (1991). ATCC preservation methods: freezing and freeze-drying. American Type Culture Collection, Dated, May 14, 2010.

Spcecc R. E. (2008). *Anaerobic Biotechnology and Odor/Corrosion Control for Municipalities and Industries*. Archae Press, Nashville Tenn.

Staab J. A., Ely J. K. (1987). Viability of lyophilized anaerobes in two media. *Cryobiology*. 24(2), 174-178.

Example 5

The following example relates to air-drying of methanogenic enrichment cultures at elevated temperatures.

Materials and Methods

Enrichment Cultures.

Two methanogenic enrichment cultures were used as described elsewhere (Schauer-Gimenez et al., 2010) to perform air drying. The culture 1 was enriched with $H_2/CO_2$ (1:1 v/v) under strict anaerobic conditions whereas culture 2 was enriched with $H_2/CO_2$ (1:1 v/v) and low dose of $O_2$ in the form of air.

Air-Drying of Cultures.

Waste biomass was collected from these reactors over three days, stored at 4° C. in glass bottles sparged with $N_2$:$CO_2$ gas (7:3 v/v), then thickened by centrifugation at 4500 rpm for 10 minutes with and without 10% glucose as a cryoprotectant (Colleran et al., 1992). The thickened biomass suspension (20 mL) was transferred to a 25-mL ceramic crucible. The biomass was air-dried by placing a crucible in a 104° C. oven for 10 to 12 hrs.

Short-Term and Simulated Long-Term Culture Storage.

After drying, cultures were analyzed for residual moisture content (RMC) by measuring the total solid (TS), and volatile solids (VS) by standard methods (APHA et al., 1998). Dried cultures were stored in a desiccator in air at room temperature for two days before activity testing. Long-term storage was simulated by holding cultures in a similar desiccator in air at an elevated temperature of 35° C. for 15 days, as described by others (Sakane and Kuroshima, 1997); this has been shown to produce activity loss similar to storage for 20 years at 5° C. under vacuum for many microorganisms.

Specific Methanogenic Activity (SMA) Testing Against $H_2$.

The activity of cultures against $H_2$, after air drying as well, as air drying and simulated storage was determined using the SMA protocol described by Coates et al. (1996) and the results were compared with wet cultures (controls). Briefly, aliquots of dried cultures were rehydrated in 300 mL of nutrient medium containing L-cysteine hydrochloride (500 mg/L) as a reducing agent. The activity test was performed in 160-mL serum bottles by injecting 100 mL pressurized gas mixture of $H_2$:$CO_2$ (4:1 v/v) in 25-mL biomass suspension (<300 mg/L VSS), incubated at 35° C. and 150 rpm. SMA (mL $CH_4$/g of VSS-h) was calculated by dividing the maximum methane production rate by the system volatile suspended solids (VSS) mass measured by standard methods (APHA et al., 1998).

Results

Figure 24:
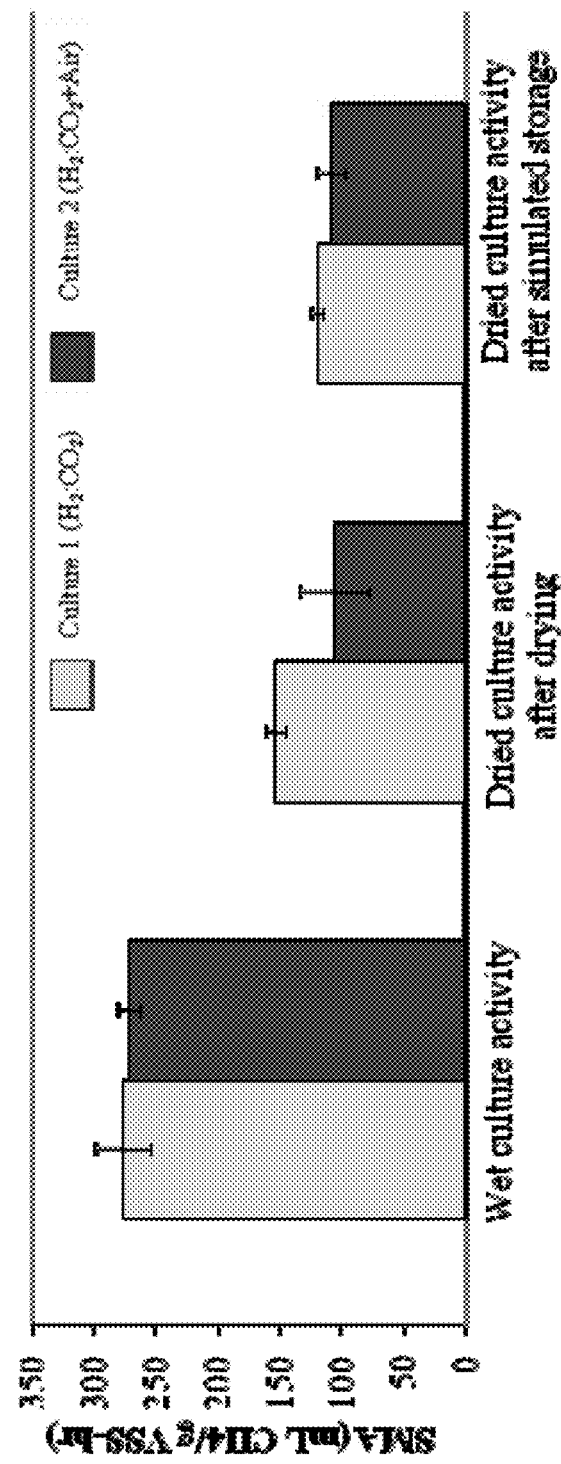
FIG. 24. illustrates methanogenic activity of cultures with protective agent. Error bars represent standard deviation among three replicates.
Figure 25:
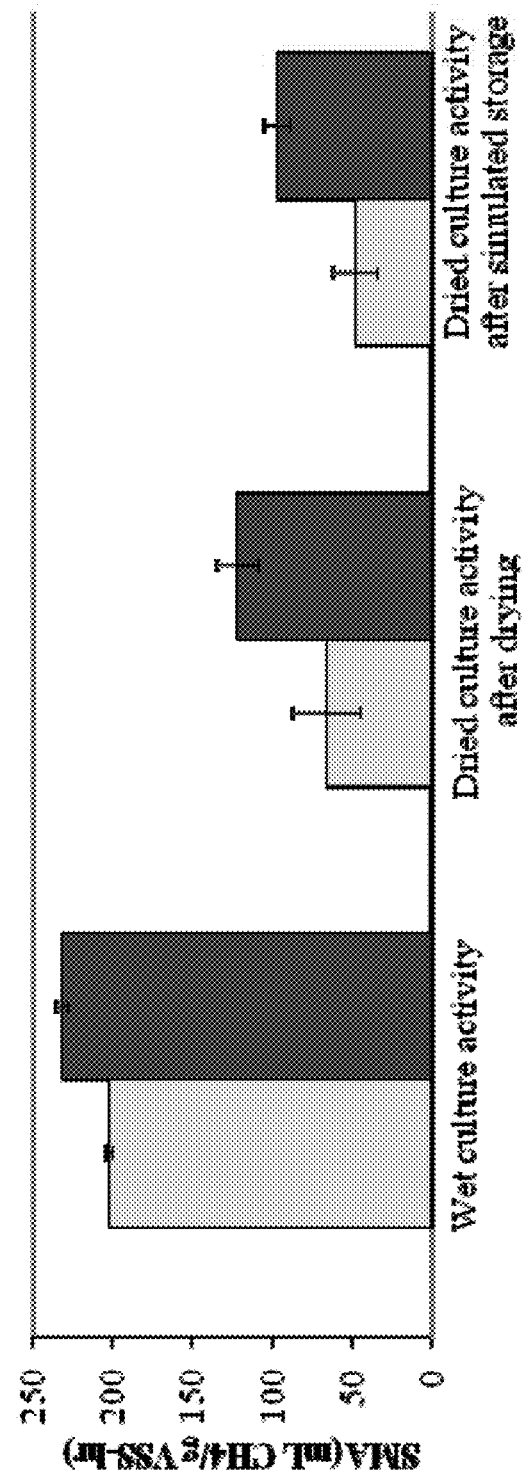
FIG. 25. illustrates methanogenic activity of cultures without protective agent. Error bars represent standard deviation among three replicates.
Figure 26:
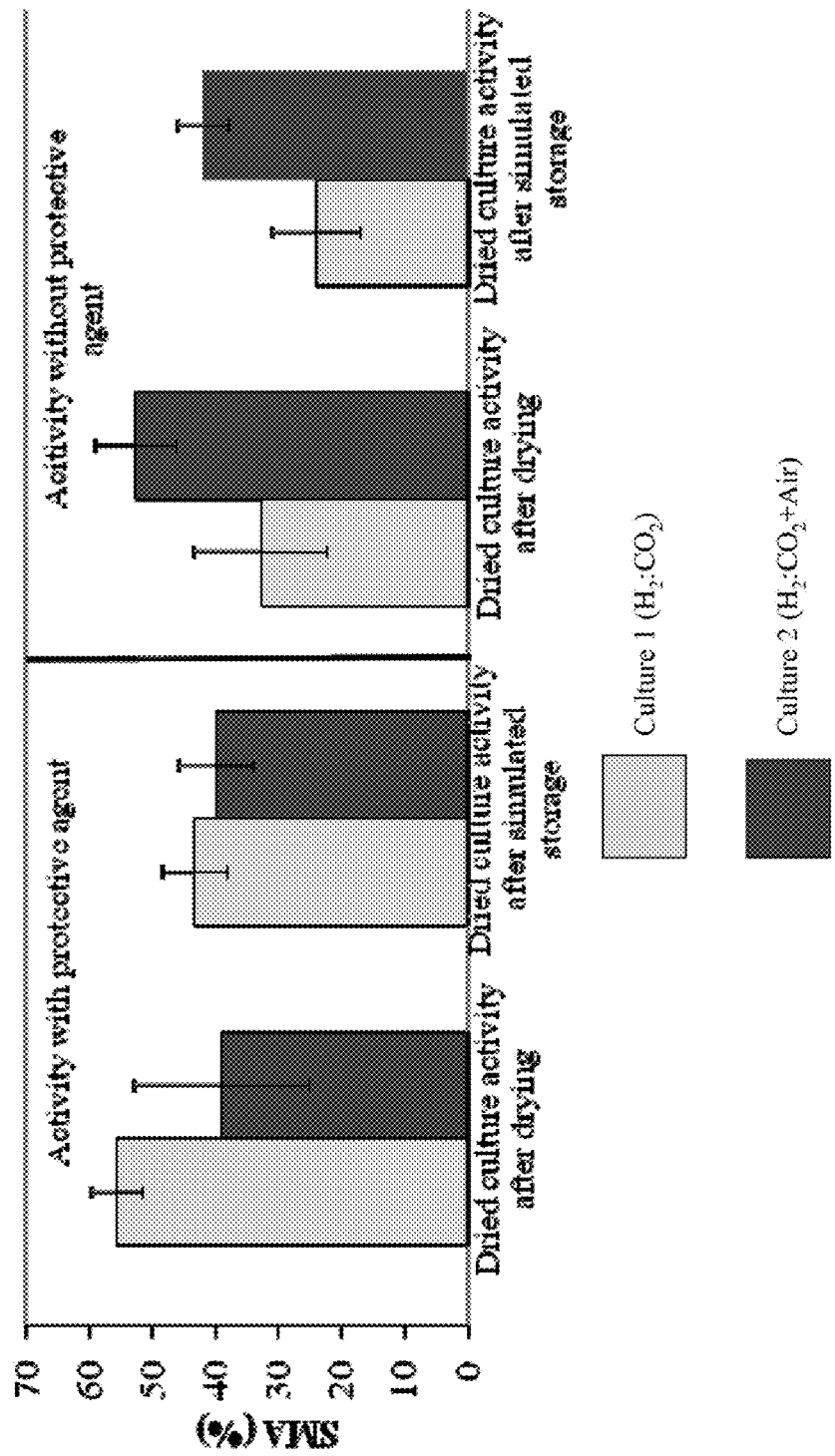
FIG. 26. illustrates percent activity of air-dried cultures with and without addition of cryoprotectant with respect to wet cultures. Error bars represent standard deviation among three replicates.

As indicated in FIGS. 24-26, the cultures retained 30 to 50% of their original methane production activity after air drying at the elevated temperature.

References for Example 5

APHA (American Public Health Association), AWWA (American Waterworks Association), and WEF (Water Environment Federation) (1998). *Standard Methods for the Examination of Water and Wastewater*, 20th edition.

Coates J. D., Coughlan M. F. and Colleran E. (1996). Simple method for the measurement of the hydrogenotrophic methanogenic activity of anaerobic sludges. *J Microbiol Methods.* 26(3), 237-246.

Colleran E., Concannon F., Golden T., Geoghegan F., Crumlish B., Killilea E., Henry M. and Coates J. (1992). Use of methanogenic activity tests to characterize anaerobic sludges, screen for anaerobic biodegradability and determine toxicity thresholds against individual anaerobic trophic groups and species. *Water Science & Technology,* 25(7).

Sakane T., Kuroshima K. (1997). Viabilities of dried cultures of various bacteria after preservation for over 20 years and their prediction by the accelerated storage test. *Microbiol. Cult. Coll.* 13, 1-7.

Schauer-Gimenez A. E., Zitomer D. H., Maki J. S, and Struble C. A. (2010). Bioaugmentation for Improved Recovery of Anaerobic Digesters After Toxicant Exposure. *Water Res.*

---

I claim:

1. A method of increasing methane production and reducing recovery time in an anaerobic digester system after the anaerobic digester system has experienced organic overload, the method comprising:
   (a) adding a culture comprising a mixture of methanogens to the anaerobic digester system, wherein the mixture comprises *Methanospirillum hungatei*, or a related hydrogenotrophic methanogen, and wherein prior to being added to the anaerobic digester system the culture was grown in the presence of oxygen given at a daily dose of 2.5 mg/L-day to 25 mg/L-day and the culture has a specific methanogenic activity that is higher than a culture not grown in the presence of oxygen, and wherein prior to being added to the anaerobic digester system the culture was enriched for methanogens that degrade an organic acid or a salt thereof; and
   (b) producing methane in the anaerobic digester system wherein the anaerobic digester system produces an increased amount of methane and has a reduced recovery time after the culture is added to the anaerobic digester system.

2. A method of increasing methane production and reducing recovery time in an anaerobic digester system after the anaerobic digester system has experienced organic overload, the method comprising:
   (a) adding a culture comprising a mixture of methanogens to the anaerobic digester system, wherein:
      the mixture comprises *Methanospirillum hungatei*, or a related hydrogenotrophic methanogen; and
      *Methanospirillum hungatei* and the related hydrogenotrophic methanogen represent at least 50% of hydrogenotrophic methanogens belonging to the order Methanomicrobiales in the culture, and wherein prior to being added to the anaerobic digester system the culture was grown in the presence of oxygen given at a daily dose of 2.5 mg/L-day to 25 mg/L-day and the culture has a specific methanogenic activity that is higher than a culture not grown in the presence of oxygen, and wherein prior to being added to the anaerobic digester system the culture was enriched for methanogens that degrade an organic acid or a salt thereof; and
   (b) producing methane in the anaerobic digester system wherein the anaerobic digester system produces an increased amount of methane and has a reduced recovery time after the culture is added to the anaerobic digester system.

3. The method of claim 1, wherein the culture is a dried culture.

4. The method of claim 2, wherein prior to being added to the anaerobic digester system the culture was grown in the presence of oxygen given at a daily dose of 2.5 mg/L-day to 25 mg/L-day.

5. The method of claim 2, wherein the culture is a dried culture.

6. A method of increasing methane production and reducing recovery time in an anaerobic digester system after the anaerobic digester system has experienced organic overload, the method comprising:
(a) adding a culture comprising a mixture of methanogens to the anaerobic digester system, wherein prior to being added to the anaerobic digester system the culture was grown in the presence of oxygen given at a daily dose of 2.5 mg/L-day to 25 mg/L-day and the culture has a specific methanogenic activity that is higher than a culture not grown in the presence of oxygen, and wherein prior to being added to the anaerobic digester system the culture was enriched for methanogens that degrade an organic acid or a salt thereof; and
(b) producing methane in the anaerobic digester system wherein the anaerobic digester system produces an increased amount of methane and has a reduced recovery time after the culture is added to the anaerobic digester system.

7. The method of claim 6, wherein the culture is a dried culture.

8. The method of claim 6, wherein the culture comprises wastewater sludge.

9. The method of claim 6, wherein the organic acid is a straight chain or branched carboxylic acid having at least three carbon atoms.

10. The method of claim 9, wherein the organic acid is propionic acid.

11. The method of claim 6, wherein the culture is added to the anaerobic digester system at a rate of at least 10 mg volatile suspended solids (VSS)/L-day.

12. The method of claim 6, wherein prior to adding the culture, partial pressure of hydrogen in the anaerobic digester system is at least $10^{-6}$ atm.

13. The method of claim 12, wherein the culture is added to the anaerobic digester system for a period of time that is sufficient to reduce the partial pressure of hydrogen in the anaerobic digester system to less than $10^{-4}$ atm.

14. The method of claim 6, wherein the culture is added to the anaerobic digester system for a period of time that is sufficient to raise the pH above 6.6.

15. The method of claim 6, wherein prior to adding the culture, the anaerobic digester system has a propionic acid concentration of at least 500 mg/L.

16. The method of claim 15, wherein the culture is added to the anaerobic digester system for a period of time that is sufficient to reduce propionic acid concentration below 500 mg/L.

17. The method of claim 1, wherein the organic acid is a straight chain or branched carboxylic acid having at least three carbon atoms.

18. The method of claim 17, wherein the organic acid is propionic acid.

19. The method of claim 2, wherein the organic acid is a straight chain or branched carboxylic acid having at least three carbon atoms.

20. The method of claim 19, wherein the organic acid is propionic acid.

* * * * *

SEQUENCE LISTING

```
<160> NUMBER OF SEQ ID NOS: 12

<210> SEQ ID NO 1
<211> LENGTH: 1466
<212> TYPE: DNA
<213> ORGANISM: Methanospirillum hungatei
<220> FEATURE:
<221> NAME/KEY: misc_feature
<222> LOCATION: (7)..(7)
<223> OTHER INFORMATION: n is a, c, g, or t

<400> SEQUENCE: 1
attctgnttg atcctgccag aggccactgc tatcggggtt tgactaagcc atgcgagtcg      60
agaggtgcaa gacctcggcg tactgctcag taacacgtgg acaatctgcc ctgaagagga     120
ggataatccc gggaaactgg gggtaatact ccatagttcg tgctgactgg aatgttatgc     180
gaacgaaaga tccgtcgctt caggatgagt ctgcggccga ttaggtagtt gttggggtaa     240
cggcccaaca agcctgtcat cggtacgggt tgtgggagca agagcccgga gatggattct     300
gagacacgaa tccaggccct acggggcgca gcaggcgcga aaactttacc atgcgggcaa     360
ccgtgataag gaaacccccga gtgccagcac aggctggctg tccaccagtg taaataactg     420
gtgaagaaag ggccgggcaa gaccggtgcc agccgccgcg gtaataccgg cggctcgagt     480
ggtggccgct attactgggc ttaaagggtc cgtagctgga tatacaagtc ccttgagaaa     540
tccgccggct taaccggtgg gcgttcaggg gaaactgtat ttctagggac cgggagaggt     600
gagaggtact gccggggtag gagtgaaatc ctgtaatccc ggtgggacca cctatggcga     660
aggcatctca ccagaacggg tccgacagtg agggacgaaa gctgggggag caaaccggat     720
tagatacccg ggtagtccca gctgtaaacg atgcgcgtta ggtgtgtcag tgaccacgtg     780
tcactgaggt gccgaaggga aaccgtgaaa cgcgccgcct ggggagtacg gtcgcaaggc     840
tgaaacttaa aggaattggc gggggagcac cacaacgggt ggagcctgcg gtttaatcgg     900
actcaacgcc ggaaatctca ccggataaga cagctgaatg atagtcggga tgaagactct     960
acttgactag ctgagaggag gtgcatggcc gtcgtcagtt cgtactgtga agcatcctgt    1020
ttagtcaggc aacgagcgag acccacgcga gcagttgcca gcttgacctt cgggttgatg    1080
gggacactgc tcggaccgcc tctgctaaag gggaggaagg aatgggcaac ggtaggtcag    1140
catgccccga attatccggg ctacacgcgg gctacaatgg acaggacaat gggtttcgac    1200
accgagaggt gaggataatc tcctaaacct gtccgaagtt cggattgcgg gttgtaactc    1260
acccgcatga agctggaatc cgtagtaatc gcgtttcaac atagcgcggt gaatatgtcc    1320
ctgctccttg cacacaccgc ccgtcaaacc acccgagtga ggtcttgatg aggatgtatc    1380
attgatatgt tcgaatctgg gttttgcaag gggggttaag tcgtaacaag gtagccgtag    1440
gggaatctgc ggctggatca cctcct                                         1466
```

<210> SEQ ID NO 2
<211> LENGTH: 743
<212> TYPE: DNA
<213> ORGANISM: Methanospirillum hungatei

<400> SEQUENCE: 2

```
cttcattacc gcataccgca tgtgtgccgg agaagcagca gtcgctgacc tgtcctttgc      60
agcaaagcac gctggtgtta tccagatggc aagtcacctc ccggcccgtc gtgcccgtgg     120
tccaaatgaa ccaggaggta tcatgttcgg acactttgct gacatgatcc aggcaaaccg     180
gaagtacccg aatgacccag caaaggcatc acttgaggtt gtcggtgcag gttgtatgct     240
cttcgaccag atctggctcg gttcctacat gtctggtggt gtcggattta cccagtatgc     300
aaccgcagca tacaccgaca acatcctcga tgagttcacc tactatggta tggactacat     360
caaggacaag tacaaagtcg actggaagaa cccaagcccg aaagacaagg tcaagccaac     420
ccaggagatc gtcaacgaca ttgccggaga ggtcaccctc aatgcaatgg agcagtacga     480
acagttccca accatgatgg aagaccactt tggtggttcc cagcgtgcag gagttatcgc     540
agcagcatcc ggtctgtctg tcggtgtcgc aacagcaaac tccaacgcag gtctgaacgg     600
atggtacctc tccatgctca tgcacaagga aggctggtca cgtctcggat tcttcggata     660
cgacctgcag gaccagtgtg gttccaccaa ctcactctct gtcagacctg acgagggttg     720
tatcggtgaa taccgtggtc cta                                             743
```

<210> SEQ ID NO 3
<211> LENGTH: 1433
<212> TYPE: DNA
<213> ORGANISM: Methanolinea tarda

<400> SEQUENCE: 3

```
ttccggttga tcctgccgga ggccactgct atcggggttc gattaagcca tgcgagtcga      60
gaggtgcaag acctcggcgc actgctcagt aacacgtgga taacctaccc tcaggtgggg     120
gataaccccg ggaaactggg gataataccc catagaccag ggacgctgga atgccccctg     180
atcgaaaggt ccgccgcctg aggatgggtc tgcggccgat taggttgttg ttggggtaac     240
ggcccaacaa gcctttgatc ggtacgggtt gtgagagcaa gagcccggag atggattctg     300
agacacaaat ccaggcccta cggggcgcag caggcgcgaa aactttacaa tgcgagaaat     360
cgtgataagg gaaccccgag tgcccgtaaa ttcgggctgt ccatcagcgt aaaaaactgg     420
tgaagaaagg gccgggcaag accggtgcca gccgccgcgg taataccggc ggctcgagtg     480
gtggccacta ttactgggct taaagcgtcc gtagctggat tgttaagtct cttgggaaat     540
ccgccggctt aaccggcggg cgttcaggag aaactgccaa tctagggacc gggagaggtg     600
agaggtactc caggggtagg agtgaaatcc tgtaatcctt ggggaccac ctgtggcgaa     660
ggcgtctcac tagaacggct ccgacagtga gggacgaaag ctgggggagc aaaccggatt     720
agataccсcgg gtagtcccag ctgtaaacga tgcgcgttag gtgtatcggt gaccacgagt     780
catcgaggtg ccgaagggaa accgtgaaac gtgccgcctg gaagtacgg tcgcaaggct     840
gaaacttaaa ggaattggcg ggggagcacc acaacggggtg gagcctgcgg tttaattgga     900
ctcaacgccg ggaagctcac cggataagac agctggatga tagccgggct gaagactctg     960
cttgactagc tgagaggagg tgcatggccg tcgtcagttc gtactgtgaa gcatcctgtt    1020
aagtcaggca acgagcgaga cccacgccaa cagttgccag cgtatcctcc gggatgacgg    1080
```

```
ggacactgtt gggaccgcct ctgctaaaga ggaggaagga atgggcaacg gtaggtcagc    1140
atgccccgaa ttatccgggc tacacgcggg ctacaatggt caggacaatg ggtatcgaca    1200
ccgagaggtg aaggcaatct cctaaacctg atcgtagttc ggattgtggg ctgcaactcg    1260
cccacatgaa gctggaatcc gtagtaatcg cgtttcaaaa tagcgcggtg aatatgtccc    1320
tgctccttgc acacaccgcc cgtcaaacca cccgagtggg gtcttgatga ggctgcggtt    1380
gccgccgtgg tcgaatctag gttccgcaag gggggttaag tcgtaacaag gta           1433
```

<210> SEQ ID NO 4
<211> LENGTH: 763
<212> TYPE: DNA
<213> ORGANISM: Methanolinea tarda

<400> SEQUENCE: 4

```
gccatgcaga ttggtatgtc cttcatcggt gcctaccgca tgtgcgccgg tgaggcggcg     60
accgctgacc ttgcattcgc agcaaagcac gccggtgtca tccagatggg tgagatcctg    120
cctgcacgcc gtgcccgtgg cccgaacgag cccggtggca tcaagttcgg acactttgcc    180
gacatggtcc agacggacag gaagtacccg aacgaccccg cacgcgcctc cctcgaggtc    240
gtgggtgcag ggacgatgct ctttgaccag atctggctcg ggtcctacat gtccggcggt    300
gtcgggttca cgcagtacgc aactgccgcc tacaccgaca acatcctcga tgactatacc    360
tactacggta tggactacat caagcagaaa tacaaagtcg actggcagaa cccgaacgag    420
aaggacaagg tcaagccgac ccaggacatc gtcaacgaca tcgcaacgga ggtcaccctc    480
tacggcatgg agcagtacga gcacttcccg actgcactcg aggaccactt cggcggttcc    540
cagcgtgcgt cggtccttgc tgctgcatcc ggtctcacga ccgcaattgc cacagggaac    600
tccaatgccg gactgaacgg ctggtacctg tccatgctcc tgcacaagga gggctggtca    660
cggctcggct tctacggata cgacctgcag gaccagtgcg gttccgcaaa caccgagtcc    720
atccgtgcag acgagggttg tgtcggagag ctccgcgggc cca                      763
```

<210> SEQ ID NO 5
<211> LENGTH: 1349
<212> TYPE: DNA
<213> ORGANISM: Methanobacterium beijingense

<400> SEQUENCE: 5

```
ttccggttga tcctgccgga ggccactgct attggggtcc gattaagcca tgcaagtcga     60
acgttcttcg gaacgtggca acggctcag taacacgtgg ataacctacc cttaggaccg    120
ggataaccct gggaaactgg ggataatacc ggatatatgg agatacctgg aatggttctc    180
cacttaaagc tccggcgcct aaggatggat ctgcggcaga ttaggtcgtt ggtggggtaa    240
tggcccacca agcctttgat ctgtacgggt tgtgagagca agagcccgga gatggaacct    300
gagacaaggt tccaggccct acggggcgca gcaggcgcga acctccgca atgcgagcaa    360 tcgcgacggg gggaccccaa gtgccactct aacggggtg gcttttctta agtgtaaaaa    420
gcttttggaa taagggctgg gcaagaccgg tgccagccgc cgcggtaaca ccggcagccc    480
aagtggtggc catttttatt gggcctaaag cgttcgtagc cggcctgata agtctctggt    540
gaaatcccgc agcttaactg tgggaattgc tggagatact atcaggcttg aggtcgggag    600
aggttagagg tactcccagg gtaggggtga atcctataa tcctgggagg accacctgtg    660
gcgaaggcgt ctaactggaa cgaacctgac ggtgagtaac gaaagccagg ggcgcgaacc    720
ggattagata cccgggtagt cctggccgta aacgatgtgg acttggtgtt gggatggcct    780
```

```
cgagctgccc cagtgccgaa gggaagctgt taagtccacc gcctgggaag tacggtcgca    840
agactgaaac ttaaaggaat tggcgggga gcaccacaac gcgtggagcc tgcggtttaa     900
atggattcaa cgccggacat ctcaccaggg gcgacagcag gatgatggcc agattgacga    960
tcttgcttga caagctgaga ggaggtgcat ggccgccgtc agctcgtacc gtgaggcgtc   1020
ctgttaagtc aggcaacgag cgagacccac gcccttagtt accagcggat ccttacagga   1080
tgccgggcac actaaggga ccgccagtga taaactggag gaaggagtgg acgacggtag    1140
gtccgtatgc cccgaatccc ctgggctaca cgcgggctac aatggctagg acaatgggtt   1200
ccaacactga aaagtgaagg taatctccta aacctagtct tagttcggat tgagggctgt   1260
aactcgccct catgaagctg gaatgcgtag taatcgcgtg tcataatcgc gcggtgaata   1320
cgtccctgct ccttgcacac accgcccgt                                    1349

<210> SEQ ID NO 6
<211> LENGTH: 493
<212> TYPE: DNA
<213> ORGANISM: Methanobacterium beijingense

<400> SEQUENCE: 6
atgatcagat ttggctaggt tcatacatgt ctggcggtgt aggattcacc cagtacgcaa     60
ccgcagcata caccgacaac atactggacg acttcaccta ctttggtaaa gagtacgtag    120
aagacaaata cggtataacc gaagcaccta acaccatgga caccgttctg gatgttgctt    180
cagaagtcac tttctacgga ctggaacagt acgaagaata cccatcacta cttgaagatc    240
agttcggagg atcacagaga gcagcagtaa ccgctgcagc atctgcatgt tccactggat    300
ttgcaactgg aaacgcccaa actgctttaa gtggatggta tctctctatg tacctgcaca    360
aagaacagca cagccgactt ggattctacg gttacgacct tcaggaccag tgtggtgcat    420
ctaacgtatt ctcaattaga ggagatgaag gattaccact ggaattgaga ggagctaact    480
atccaaacta cgc                                                     493

<210> SEQ ID NO 7
<211> LENGTH: 20
<212> TYPE: DNA
<213> ORGANISM: Artificial
<220> FEATURE:
<223> OTHER INFORMATION: Forward primer for amplifying 16S rRNA gene of
      Archaeal communities

<400> SEQUENCE: 7
ttccggttga tccygccgga                                                20

<210> SEQ ID NO 8
<211> LENGTH: 19
<212> TYPE: DNA
<213> ORGANISM: Artificial
<220> FEATURE:
<223> OTHER INFORMATION: Reverse primer for amplifying 16S rRNA gene of
      Archael communities

<400> SEQUENCE: 8
yccggcgttg amtccaatt                                                 19

<210> SEQ ID NO 9
<211> LENGTH: 20
<212> TYPE: DNA
<213> ORGANISM: Artificial
<220> FEATURE:
```

```
<223> OTHER INFORMATION: Forward primer for amplifying pUC plasmid

<400> SEQUENCE: 9
ggaattgtga gcggataaca                                               20

<210> SEQ ID NO 10
<211> LENGTH: 20
<212> TYPE: DNA
<213> ORGANISM: Artificial
<220> FEATURE:
<223> OTHER INFORMATION: Reverse primer for amplifying pUC plasmid

<400> SEQUENCE: 10
ggcgattaag ttgggtaacg                                               20

<210> SEQ ID NO 11
<211> LENGTH: 32
<212> TYPE: DNA
<213> ORGANISM: Artificial
<220> FEATURE:
<223> OTHER INFORMATION: Forward primer for amplifying mcrA gene of
      methanogenic communities

<400> SEQUENCE: 11
ggtggtgtmg gattcacaca rtaygcwaca gc                                 32

<210> SEQ ID NO 12
<211> LENGTH: 23
<212> TYPE: DNA
<213> ORGANISM: Artificial
<220> FEATURE:
<223> OTHER INFORMATION: Reverse primer for amplifying mcrA gene of
      methanogenic communities

<400> SEQUENCE: 12
ttcattgcrt agttwggrta gtt                                           23
```